US007976852B2

(12) United States Patent
Rossignol et al.

(10) Patent No.: US 7,976,852 B2
(45) Date of Patent: Jul. 12, 2011

(54) COMPOSITIONS AND METHODS FOR CANCER IMMUNOTHERAPY

(75) Inventors: Daniel P. Rossignol, Ridgefield Park, NJ (US); Sally T. Ishizaka, Weston, MA (US); Lynn D. Hawkins, Concord, MA (US); Scott Z. Fields, Towaco, NJ (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/411,332

(22) Filed: Apr. 26, 2006

(65) Prior Publication Data
US 2007/0020232 A1    Jan. 25, 2007

Related U.S. Application Data

(60) Provisional application No. 60/674,680, filed on Apr. 26, 2005.

(51) Int. Cl.
*A61K 31/395* (2006.01)

(52) U.S. Cl. ............... 424/277.1; 424/178.1; 514/263.3; 514/183; 514/269

(58) Field of Classification Search ............... 424/178.1, 424/277.1; 514/263.3, 183, 269
See application file for complete search history.

(56) References Cited

U.S. PATENT DOCUMENTS

| | | | |
|---|---|---|---|
| 5,484,911 A | 1/1996 | Hong et al. | |
| 5,635,188 A | 6/1997 | Bystryn | |
| 5,681,824 A | 10/1997 | Christ et al. | |
| 5,895,653 A | 4/1999 | Eibl et al. | |
| 5,904,925 A | 5/1999 | Exner | |
| 5,961,970 A | 10/1999 | Lowell et al. | |
| 5,985,284 A | 11/1999 | Lowell | |
| 6,136,797 A | 10/2000 | Zilch et al. | |
| 6,146,632 A | 11/2000 | Momin et al. | |
| 6,146,659 A | 11/2000 | Rahman | |
| 6,165,502 A | 12/2000 | Oleske et al. | |
| 6,172,049 B1 | 1/2001 | Dwyer et al. | |
| 6,180,111 B1 | 1/2001 | Stein et al. | |
| 6,290,973 B1 | 9/2001 | Hawkins et al. | |
| 6,306,404 B1 | 10/2001 | LaPosta et al. | |
| 6,355,257 B1 | 3/2002 | Johnson et al. | |
| 6,437,165 B1 | 8/2002 | Mandala et al. | |
| 6,521,776 B2 | 2/2003 | Hawkins et al. | |
| 6,551,600 B2 | 4/2003 | Hawkins et al. | |
| 6,630,161 B1 | 10/2003 | Leesman | |
| 6,835,721 B2 | 12/2004 | Hawkins et al. | |
| 7,416,726 B2 * | 8/2008 | Ravetch ..................... | 424/133.1 |
| 7,560,584 B2 | 7/2009 | Hawkins et al. | |
| 2002/0049314 A1 | 4/2002 | Hawkins et al. | |
| 2002/0176861 A1 | 11/2002 | Hawkins et al. | |
| 2003/0153532 A1 | 8/2003 | Hawkins et al. | |
| 2004/0006242 A1 | 1/2004 | Hawkins et al. | |
| 2005/0123566 A1 | 6/2005 | Hawkins et al. | |
| 2005/0164988 A1 | 7/2005 | Hawkins et al. | |
| 2007/0020232 A1 | 1/2007 | Rossignol et al. | |
| 2007/0027111 A1 | 2/2007 | Hawkins et al. | |
| 2007/0292418 A1 * | 12/2007 | Fields et al. ............... | 424/133.1 |

FOREIGN PATENT DOCUMENTS

| | | |
|---|---|---|
| EP | 0 390 216 A2 | 3/1990 |
| JP | 02-261866 | 10/1990 |
| WO | WO 93/04672 A1 | 3/1993 |
| WO | WO 95/11700 A1 | 5/1995 |
| WO | WO 98/57659 A1 | 12/1998 |
| WO | WO 00/44758 A1 | 8/2000 |
| WO | WO 00/73263 A1 | 12/2000 |
| WO | WO 01/46127 A1 | 6/2001 |
| WO | WO 01/90129 A2 | 11/2001 |
| WO | WO 02/09752 A2 | 2/2002 |
| WO | WO 03/003985 A2 | 1/2003 |
| WO | WO 03/011223 A2 | 2/2003 |
| WO | WO 03099195 A2 | 12/2003 |

OTHER PUBLICATIONS

Seaver (1994) Genetic Engineering vol. 14(14):pp. 10 and 21.*
Chatterjee et al. Cancer Immunol. Imunother. (1994).*
Dermer, Biotechnology 12: 320 (1994).*
Gura et al (Science 278:1041-1042 (1997).*
Voskoglou-Nomikos (Clin. Can. Res. 9:4227-4239 (2003)).*
Jain (Scientific American Jul. 1994:58-64).*
Esai Research Inst. product datasheet for E6020 or ER-804057 (pp. 1-5; Mar. 1999).*
Baselga et al., Cancer Res. 58:2825 (1998).*
Cragg et al., Blood 103:2738 (2004).*
Overholser et al., Cancer 89:74 (2000).*
Clynes et al., Nature Med. 6:443 (2000).*
Zhang et al., J. Clin. Oncol. 25:3712 (2007.*
Baldridge et al., Exp. Opin. Biol. Ther. 4:1129 (2004).*
Jiang et al., Curr. Med. Chem. 10:1423 (2003).*
Dalpke et al., Biodrugs 16:419 (2002).*
Cooper et al., J. Clin. Immunol. 24:693 (2004).*
Skinner, Dermatol. Clint 21:291 (2003).*
Coelho et al. (British J. Can. 90:2032-2041 (2004)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Lederman et al (Molecular Immunology 28:1171-1181, 1991).*
Li et al (Proc. Natl. Acad. Sci. USA 77:3211-3214, 1980).*
Berenbaum Clin. Exp. Immunol. 28:1-18 (1977).*
Berenbaum Pharmacol. Rev. 41:93-141 (1989)).*
Tallarida "Drug Synergism and Dose Effect Analysis" Ed. Chapman & Hall (2000), pp. 1-8, 10-13 and 57-71.*

(Continued)

*Primary Examiner* — Lynn Bristol

(74) *Attorney, Agent, or Firm* — Myers Bigel Sibley & Sajovec P.A.

(57) ABSTRACT

The invention relates to immunotherapeutic compounds and to methods for stimulating an immune response in a subject individual at risk for developing cancer, diagnosed with a cancer, in treatment for cancer, or in post-therapy recovery from cancer or the compounds of the invention can be administered as a prophylactic to a subject individual to prevent or delay the development of cancer.

27 Claims, 4 Drawing Sheets

OTHER PUBLICATIONS

Mitchell M S. Immunotherapy as part of combinations for the treatment of cancer. International Immunopharmacology (2003), vol. 3, pp. 1051-1059.
Schuster M et al. Cancer immunotherapy. Biotechnol. J. (2006), vol. 1, pp. 138-147.
Search Report and Written Opinion for PCT/US06/15688, mailed Jul. 31, 2008.
Hawkins LD et al. Inhibition of endotoxin response by synthetic TLR4 antagonists. Current Topics in Medicinal Chemistry (2004), vol. 4, No. 11, pp. 1147-1171.
Hawkins LD et al. A novel class of endotoxin receptor agonists with simplified structure, toll-like receptor 4-dependent immunostimulatory action, and adjuvant activity. The Journal of Pharmacology and Experimental Therapeutics (2002), vol. 300, No. 2, pp. 655-661.
Rossignol DP and Lynn M. TLR4 antagonists for endotoxemia and beyond. Current Opinion in Investigational Drugs (2005), vol. 6, No. 5, pp. 495-502.
Berzoksky and Berkower, "Chapter 8: Immunogenicity and Antigen Structure," *Fundamental Immunology*, William E. Paul, ed., Raven Press NY, p. 242 (1993).
Bhattacharya et al., "Synthesis and Vesicle Formation from Novel Pseudoglyceryl Dimeric Lipids. Evidence of Formation of Widely Different Membrane Organizations with Exceptional Thermotropic Properties," *Chem. Commun.* 23:2287-2288 (1997).
Cespedes of al., "Mouse Models in Oncogenesis and Cancer Therapy," *Clin. Transl. Oncol.* 8(5):318-329 (2006).
Cheung and Paterson, "American Chemical Society—226$^{th}$ National Meeting: New Drug Highlights," *IDrugs* 6(10):939-942 (2003).
Defoort et al., "Macromolecular Assemblage in the Design of a Synthetic AIDS Vaccine," *Proc. Natl. Acad. Sci. USA* 89:3879-3883 (1992).
Dennis, "Off by a Whisker," *Cancer News Feature* 442:739-741 (2006).
Dullenkopf et al, "Synthesis of a Structurally Defined Antigen-Immunostimulant Combination for Use in Cancer Vaccines," *Chem. Euro. J.* 5(8):2432-2438 (1999).
Duralski et al., "Synthesis of Isotopically Labelled Cardiolipins," *Tetrahedron Lett.* 1607-1610 (1998).
Eustache et al., "New Acyclic Analogues of Lipid A: Synthesis of 4-Phosphonoxybutyl and 3-Phosphonoxypropyl Glycosides of 2-Amino-2-Deoxy-D-Glucose," *Carbohydrate Res.* 251:251-267 (1994).
Gokhale et al., "An improved method of encapsulation of doxorubicin in liposomes: pharmacological, toxicological, and therapeutic evaluation," *Br. J. Cancer* 74:43-48 (1996).
Gregoriadis et al., "Liposomes as Immunological Adjuvants and Vaccine Carriers," *J. Controlled Release* 41(Jan. 2002):49-56 (1996).
Hawkins et al., "Inhibition of endotoxins response by synthetic TLR4 antagonists," *Curr. Topics Med. Chem.* 4:1147-71 (2004).
Hoffmann et al., "Induction of Tumor Cytotoxicity in Murine Bone Marrow-Derived Macrophages by Two Synthetic Lipopeptide Analogues," *Biol. Chem.* 370:575-582 (1989).
Homma et al., "Structural Requirements of Lipid A Responsible for the Functions: A Study with Chemically Synthesized Lipid A and its Analogues," *J. Biochem.* 98:395-406 (1985).
Inoue and Nojima, "Immunochemical Studies of Phospholipids. I. Reactivity of Various Synthetic Cardiolipin Derivatives with Wassermann Antibody," *Chem. Phys. Lipids* 1(4):360-367 (1967).
Inoue and Nojima, "Immunochemical Studies of Phospholipids. II, Syntheses of Cardiolipin and its Analogues," *Chem. Pharm. Bull.* 16(1):76-81 (1968).
Inoue and Nojima, "Immunochemical Studies of Phospholipids IV: The Reactivities of Antisera Against Natural Cardiolipin and Synthetic Cardiolipin Analogues-Containing Antigens," *Chem. Phys. Lipids*(*CPLIA4*) 3(1):70-77 (1969).
Jain et al., "Effect of the Structure of Phospholipid on the Kinetics of Intravesicle Scooting of Phospholipase $A_2$," *Biochimica Biophysica Acta* 860(3):462-474 (1986).
Jiang and Koganty, "Synthetic Vaccines: The Role of Adjuvants in Immune Targeting," *Curr. Med. Chem.* 10:1423-1439 (2003).

Kamitakahara et al., "A Lysoganglioside/poly-L-glutamic Acid Conjugate as a Picomolar Inhibitor of Influenza Hemagglutinin," *Angew. Chem. Int. Ed.* 37(11):1524-1528 (1998).
Lien et al., "A Novel Synthetic Acyclic Lipid A-Like Agonist Activates Cells Via the Lipopolysaccharide/Toll-Like Receptor 4 Signaling Pathway," *J. Biol. Chem.* 276(3):1873-1880 (2001).
Matsuura et al., "Activity of Monosaccharide Lipid A Analogues in Human Monocytic Cells as Agonists or Antagonists of Bacterial Lipopolysaccharide," *Infect. Immun.* 67(12):6286-6292 (1999).
Merriam-Webster's Collegiate Dictionary, 10th edition, published 1998 by Merriam-Webster, Inc., p. 924.
Przetak et al., "Novel Synthetic LPS Receptor Agonists Boost Systemic and Mucosal Antibody Responses in Mice," *Vaccine* 21:961-970 (2003).
Reichel et al., "Synthetic Carbohydrate-Based Vaccine: Synthesis of an L-Glycero-D-Manno-Heptose Antigen-T-Epitope-Lipopeptide Conjugate," *Chem. Commun.* pp. 2087-2088 (1997).
Roitt et al., "Adjuvants," *Immunology* 8.9 Gower Medical Publishing, London (1985).
Rossignol and Lynn, "TLR4 antagonists for endotoxemia and beyond," *Curr. Opin. Invest. Drugs* 6:295-502 (2005).
Seydel et al., "The Generalized Endotoxic Principle," *Eur. J. Immunol.* 33:1586-1592 (2003).
The Merck Manual of Diagnosis and Therapy, 17th Edition, 1999, published by Merck Research Laboratories pp. 397-398, 948-949, 1916, and 1979-1981.
The Merck Manual of Diagnosis and Therapy, 17th Edition, 1999, published by Merck Research Laboratories , pp. 1420-1421.
The Oxford Textbook of Oncology, 1995, published by Oxford University Press, pp. 447-453.
Toyokuni et al., "Synthetic Vaccines: Synthesis of a Dimeric Tn Antigen-Lipopeptide Conjugate that Elicits Immune Responses Against Tn-Expressing Glycoproteins," *J. Am. Chem. Soc.* 116:395-396 (1994).
Vogel, "Immunologic Adjuvants for Modern Vaccine Formulations," *Ann. NY Acad. Sci.* 754:153-160 (1995).
Weissig et al., "Functionalized Liposomes with Immunological Adjuvant Effects," *Wiss Z. Martin Luther Univ. Halle-Wittenberg, Math. Naturwiss. Reihe* 39(6):101-109 (1990) (German Language Only).
Wiesmuller et al., "Novel Low-Molecular-Weight Synthetic Vaccine Against Foot-and-Mouth Disease Containing a Potent B-Cell and Macrophage Activator," *Vaccine* 7:29-33 (1989).
Wiesmuller et al., "Solid Phase Peptide Synthesis of Lipopeptide Vaccines Eliciting Epitope-Specific B-, T-Helper and T-Killer Cell Response," *Int. J. Peptide Protein Res.* 40:255-260 (1992).
Wikipedia, online encyclopedia. "Toll-Like Receptor" Definition from Wikipedia.org, (http://en.wikipedia.org/wiki/Toll_Like_Receptor) Accessed Jul. 12, 2006 (5 pages).
U.S. Appl. No. 10/157,791; Filed: May 28, 2002; Office Action Mailed: Sep. 9, 2004.
U.S. Appl. No. 10/157,791; Filed: May 28, 2002; Office Action Mailed: Jun. 16, 2005.
U.S. Appl. No. 11/077,344; Filed: Mar. 9, 2005; Office Action Mailed: Oct. 4, 2007.
U.S. Appl. No. 11/077,344; Filed: Mar. 9, 2005; Office Action Mailed: Jul. 3, 2008.
U.S. Appl. No. 11/411,564; Filed: Apr. 26, 2006; Office Action Mailed: Oct. 2, 2008.
U.S. Appl. No. 11/024,328; Filed: Dec. 28, 2004; Office Action Mailed: Sep. 17, 2007.
U.S. Appl. No. 11/024,328; Filed: Dec. 28, 2004; Office Action Mailed: Mar. 6, 2008.
U.S. Appl. No. 11/605,557; Filed: Nov. 28, 2006; Office Action Mailed: Jun. 26, 2008.
Belimezi et al., "Growth inhibiton of breast cancer cell lines overexpressing Her2/neu by a novel internalized fully human Fab antibody fragment," *Cancer Immunol. Immunother.* 55:1091-1099 (2006).
Ross et al., "The Her-2/*neu* Gene and Protein in Breast Cancer 2003: Biomarker and Target of Therapy," *Oncologist* 8:307-325 (2003).
Schuster et al., "Cancer Immunotherapy," *Biotechnol. J.* 1:138-147 (2006).

U.S. Appl. No. 11/605,557; Filed: Nov. 28, 2006; Office Action Mailed: Feb. 26, 2009.

U.S. Appl. No. 11/411,564; Filed: Apr. 26, 2006; Office Action Mailed: May 12, 2009.

U.S. Appl. No. 11/077,344; Filed Mar. 9, 2005; Office Action Mailed: Jun. 30, 2009.

U.S. Appl. No. 11/411,564; Filed Apr. 26, 2006; Office Action Mailed: Oct. 7, 2009.

U.S. Appl. No. 11/605,557; Filed Nov. 28, 2006; Office Action Mailed: Sep. 4, 2009.

Braga et al., "Making crystals from crystals: a green route to crystal engineering and polymorphism," Chem. Commun. pp. 3635-3645 (2005).

Vippagunta et al., "Crystalline Solids," Adv. Drug Deliv. Rev. 48:3-26 (2001).

Jain et al., "Polymorphism in Pharmacy," Indian Drugs 23:315-329 (1986).

Pharmaceutical Dosage Forms: Tablets, vol. 2, Published 1990 by Marcel Dekker, Inc., ed. By Lieberman, Lachman, and Schwartz, pp. 462-472 (1990).

U.S. Appl. No. 11/605,557; Filed Nov. 28, 2006; Office Action Mailed: Jan. 22, 2010.

U.S. Appl. No. 11/411,564; Filed Apr. 26, 2006; Office Action Mailed: Mar. 18, 2010.

U.S. Appl. No. 11/077,344; Filed Mar. 9, 2005; Office Action Mailed: Jan. 14, 2010.

* cited by examiner

Intraperitoneal (i.p.)TLR agonists enhance therapeutic efficacy of B16-GM-CSF vaccine

COMPOSITIONS AND METHODS FOR CANCER IMMUNOTHERAPY

FIELD OF THE INVENTION

The invention provides compositions and methods for cancer immunotherapy.

1. BACKGROUND OF THE INVENTION

Cancer immunotherapy involves the use of compositions and methods to elicit and enhance an individual's own immune system against cancerous cells, or infections that predispose to cancer. Cancer vaccines function by triggering the immune system to mount a response to an antigen (e.g., typically a protein, peptide, or carbohydrate) that is introduced into the body in a non-carcinogenic form and triggers the body to confer immunity or obtain a long-lived "memory" immune response. See, e.g., Kast, *Peptide-Based Cancer Vaccines*, Landes Bioscience (2000); Stem et al, *Cancer Vaccines and Immunotherapy*, Cambridge University Press (2000). Once the immune system response is established, exposure of the immune system to this antigen (e.g., in the form of a cancerous tumor) results in a rapid and robust immune response.

It is often necessary to enhance the immune response to the antigens present in a vaccine in order to stimulate the immune system to a sufficient extent to make a vaccine effective, i.e., to confer immunity. Many protein, peptide and carbohydrate antigens, administered alone, do not generate a sufficient response to confer immunity. The reasons for this may be that the antigens recognized by cancer reactive immune responses originate from proteins that are expressed in normal tissue of the same histological type as the cancer, such that immunologic tolerance may prevent effective immune responses to the antigens. Such antigens need to be presented to the immune system in such a way that they will generate an immune response. To this end, adjuvants have been devised which immobilize antigens and enhance the immune response. The best known adjuvant, Freund's complete adjuvant, consists of a mixture of mycobacteria in an oil/water emulsion. Freund's adjuvant works (i) by enhancing cell and humoral-mediated immunity and (ii) by blocking rapid dispersal of the antigen challenge (the depot effect). Freund's adjuvant is used primarily with experimental therapies to help stimulate the immune system in animals, and in humans the mycobacterial preparation Bacille Calmette-Guérin (BCG), is an immunotherapy approved as a treatment for bladder cancer.

Another molecule that has been shown to have immunostimulatory or adjuvant activity is endotoxin, also known as lipopolysaccharide (LPS). LPS is also a model adjuvant that can overcome tolerance to self antigens. Waldner, et al., *J. Clin. Invest.,* (2004); 113 990-997. While LPS is too toxic to be a viable adjuvant, molecules that are structurally related to endotoxin, such as monophosphoryl lipid A ("MPL"), are being tested as adjuvants in clinical trials. The only FDA-approved adjuvant for use in humans are aluminum salts, alum.

There is a need in the art for safe and effective compositions that can stimulate the immune system as a cancer immunotherapeutic. The invention is directed to this, as well as other, important ends.

2. SUMMARY OF THE INVENTION

The present invention relates to a composition having (i) at least one immunotherapeutic agent which may be one or more cancer antigens, one or more antigens derived from a virus associated with cancer, one or more anti-cancer antibodies; and an anti-idiotypic antibody to an anti-cancer antibody; and, (ii) one or more compounds of formulae (I), (II), (III), (IV), and (V) and/or a pharmaceutically acceptable salt, hydrate, solvate, stereoisomer, amorphous solid thereof, or any combination thereof.

The compounds of the invention can administered to a subject invidual at risk for developing cancer, diagnosed with a cancer, in treatment for cancer, or in post-therapy recovery from cancer or the compounds of the invention can be administered as a prophylactic to a subject individual to prevent or delay the development of cancer.

The invention further relates to methods for stimulating an immune response in an subject individual by (a) administering to the individual at least one immunotherapeutic agent selected from one or more cancer antigens; one or more viral derived antigen associated with cancer; one or more anti-cancer antibodies; and one or more anti-idiotypic antibodies to an anti-cancer antibody; and (b) administering to the individual one or more compound selected from formulae (I), (II), (III), (IV) and (V) and/or a pharmaceutically acceptable salt, hydrate, solvate, stereoisomer, amorphous solid thereof, or any combination thereof.

These and other aspects of the invention are described in more detail herein.

3. FIGURES

4. DETAILED DESCRIPTION OF THE INVENTION

Figure 1:
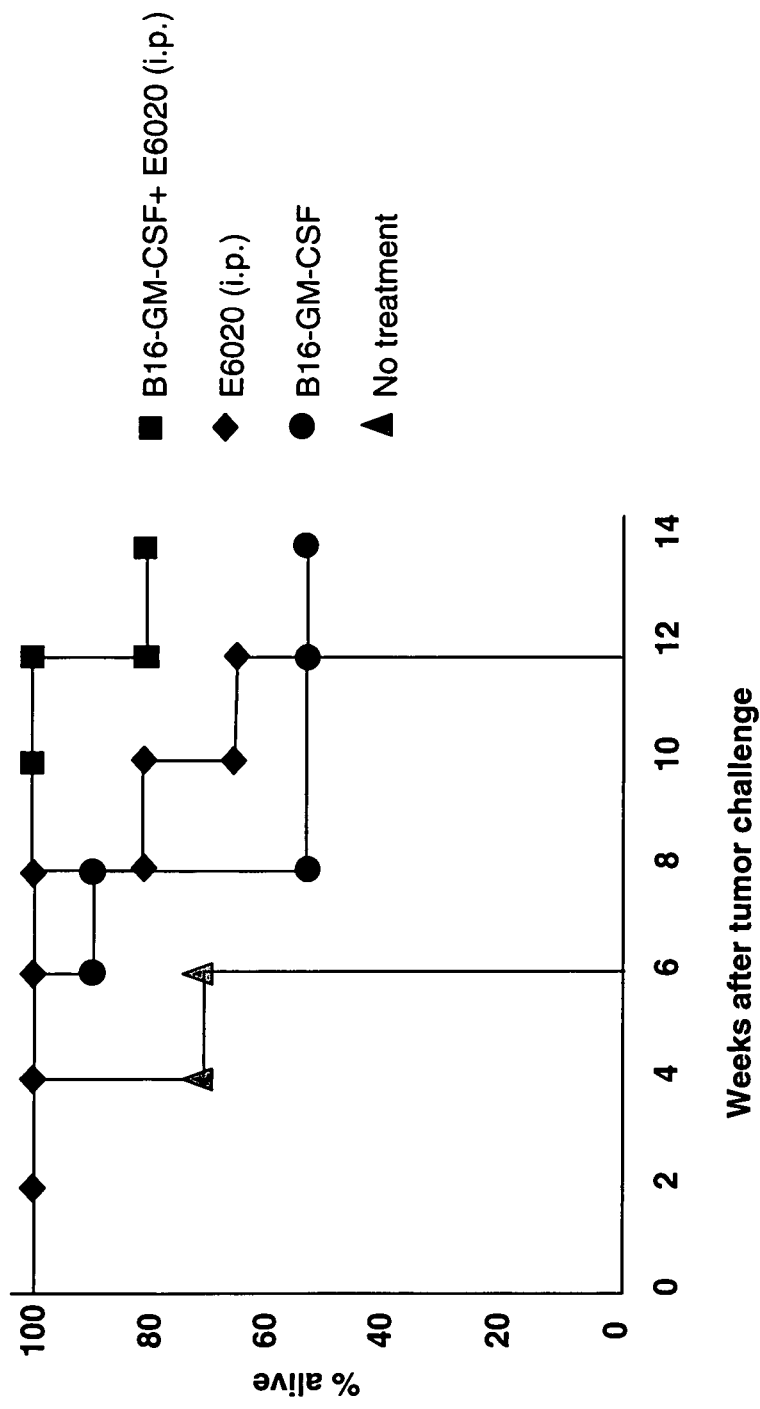
FIG. 1 is a graph depicting the percentage of tumor-bearing mice surviving after treatment with subcutaneous B16 GM-CSF(R) cells, E6020, or B16 GM-CSF (r) cells and E6020, or with no treatment.

The invention provides compositions comprising (i) at least one immunotherapeutic agent selected from one or more cancer antigens, one or more antigens derived from a virus associated with cancer, one or more an anti-cancer antibody, and one or more anti-idiotypic antibody to an anti-cancer antibody, and (ii) one or more compounds selected from formulae (I), (II), (III), (IV), and (V), and/or a pharmaceutically acceptable salt, hydrate, solvate, stereoisomer, amorphous solid thereof, or any combination thereof. The compounds are described in detail below. The compositions may be therapeutic, that is, the compounds are administered to treat an existing cancer, or to prevent the recurrence of a cancer, or prophylactic, that is, the compounds are administered to prevent or delay the development of cancer. When the compositions are used therapeutically, they are administered to cancer patients and are designed to elicit an immune response to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments. A composition used as a prophylactic treatment is administered to individuals who do not have cancer, and are designed to elicit an immune response to target potential cancer cells or to target an antigen derived from a virus associated with cancer.

The compositions of this invention may include more than one immunotherapeutic agent with another immunotherapeutic agent, for example, a cancer antigen in combination with one or more antigens derived from a virus associated with cancer, one or more anti-cancer antibodies, and one or more anti-idiotypic antibodies to an anti-cancer antibody. Another embodiment of the compositions may include one or more cancer antigens and an anti-cancer antibody and/or an anti-idiotypic antibody to an anti-cancer antibody. Other embodiments of the compositions may include an anti-cancer antibody and an anti-idiotypic antibody to an anti-cancer antibody. Another embodiment may include one or more antigens derived from a virus associated with cancer and an anti-cancer antibody and/or an anti-idiotypic antibody to an anti-cancer antibody.

4.1 Cancer Antigens

One of the immunotherapeutic agents of the pharmaceutical composition may be one or more cancer antigens. A cancer antigen is (a) a cell surface antigen that can be found on a malignant cell, (b) an antigen that can be found inside a malignant cell or (c) a mediator of tumor cell growth.

The term "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with cancer.

The cancer antigen can be any type of cancer antigen known in the art. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen.

In another embodiment, the cancer antigen is a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen.

In another embodiment, the cancer antigen is a mucin-1 protein or peptide (MUC-1) that is found on all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system. See Gendler, S. J., et al., *J. Biol. Chem.* 265:15286-15293 (1990).

In another embodiment, the cancer antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay. Mercer and Pritchard, *Biochim Biophys Acta.* (2003); 1653(1):25-40; Sharkey, et al, *Cancer Res.* (2004);64(5):1595-9.

In one embodiment, the cancer antigen is a human epidermal growth factor receptor-2 (HER-2/neu) antigen. Cancers that have cells that overexpress HER-2/neu are referred to as HER-2/neu$^+$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK® Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK® Accession No. AAA58637. Based on these sequences, one skilled in the art could develop HER-2/neu antigens using known assays to find appropriate epitopes that generate an effective immune response. Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [9$_{754}$]; and the like.

In one embodiment, the cancer antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR$^+$ cancers. Exemplary EGFR$^+$ cancers include lung cancer, head and neck cancer, colon cancer, colorectal cancer, breast cancer, prostate cancer, gastric cancer, ovarian cancer, brain cancer and bladder cancer.

The nucleotide sequence (mRNA) of EGFR variant 1 is available at GENBANK® Accession No. NM_005228. The nucleotide sequence (mRNA) of EGFR variant 2 is available at GENBANK® Accession No. NM_201282. The nucleotide sequence (mRNA) of EGFR variant 3 is available at GENBANK® Accession No. NM_201283. The nucleotide sequence (mRNA) of EGFR variant 4 is available at GENBANK® Accession No. NM_201284. Exemplary EGFR antigens include GI-3001; peptide aa 1168-1181; and the like.

In one embodiment, the cancer antigen is a vascular endothelial growth factor receptor (VEGFR) antigen. The VEGFR antigen can be VEGFR variant 1 antigen or VEGFR variant 2 antigen. VEGFR variant 1 is synonymous with Flt-1. VEGFR variant 2 is synonymous with Flk-1 and Kdr (i.e., kinase insert domain protein receptor). VEGFR is considered to be a regulator of cancer-induced angiogenesis. Cancers with cells that overexpress VEGFR are called VEGFR+ cancers. Exemplary VEGFR+ cancers include breast cancer, lung cancer, small cell lung cancer, colon cancer, colorectal cancer, renal cancer, leukemia, and lymphocytic leukemia.

The nucleotide sequence (DNA) for VEGFR variant 1 (Flt-1) is available at GENBANK® Accession No. D64016 (human gene for vascular endothelial growth factor receptor, promoter and exon 1). The nucleotide sequence (mRNA) for VEGFR variant 2 (Flk-1 or Kdr) is available at GENBANK® Accession No. AF063658 (human vascular endothelial growth factor receptor 2).

In one embodiment the cancer antigen is prostate-specific antigen (PSA) and/or prostate-specific membrane antigen (PSMA) that are prevalently expressed in androgen-independent prostate cancers.

In another embodiment, the cancer antigen is Gp-100 Glycoprotein 100 (gp 100) is a tumor-specific antigen associated with melanoma.

In one embodiment, the cancer antigen is a carcinoembryonic (CEA) antigen. Cancers with cells that overexpress CEA are referred to as CEA+ cancers. Exemplary CEA+ cancers include colorectal cancer, gastric cancer and pancreatic cancer. The nucleotide sequence (mRNA) for human carcinoembryonic antigen-like 1 is available at GENBANK® Accession No. NM_020219. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e. CEA aa 345-354), CAP-6 (i.e., CEA aa 19-28) and CAP-7.

In one embodiment, the cancer antigen is carbohydrate antigen 10.9 (CA 19.9). CA 19.9 is an oligosaccharide related to the Lewis A blood group substance and is associated with colorectal cancers.

In another embodiment, the cancer antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In one embodiment, the cancer antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In another embodiment of the invention, the cancer antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

The cancer antigen can be a cell, a protein, a peptide, a fusion protein, DNA encoding a peptide or protein, RNA encoding a peptide or protein, a glycoprotein, a lipoprotein, a phosphoprotein, a carbohydrate, a lipopolysaccharide, a lipid, a chemically linked combination of two or more thereof, a fusion or two or more thereof, or a mixture of two or more thereof. In another embodiment, the cancer antigen is a peptide comprising about 6 to about 24 amino acids; from about 8 to about 20 amino acids; from about 8 to about 12 amino acids; from about 8 to about 10 amino acids; or from about 12 to about 20 amino acids. In one embodiment, the cancer antigen is a peptide having a MHC Class I binding motif or a MHC Class II binding motif. In another embodiment, the cancer antigen comprises a peptide that corresponds to one or more cytotoxic T lymphocyte (CTL) epitopes.

In another embodiment, the cancer antigen is in the form of a foreign homologous cancer antigen. Foreign homologous cancer antigens and methods for making them are described in U.S. Pat. No. 6,942,862. Because many human cancer antigens are self proteins (i.e., proteins normally produced by an individual and not necessarily unique to cancer), immunologic tolerance may exist and represent a barrier to effective vaccination against the human cancer antigens. This aspect of the invention overcomes immunologic tolerance by immunizing a patient with a protein or peptide that is foreign (i.e., not identical to that in the individual) but nevertheless homologous to an individual's self cancer antigen or portion thereof. "Foreign" cancer antigens can be generated from, for example, rabbits, rats, mice and pigs. Generally, a foreign cancer antigen (e.g., protein or peptide) will possess at least about 75% sequence homology to the cancer antigen targeted. Sequence homology means either identical amino acids at the same positions in the sequence (i.e., sequence identity), or conservative substitutions of amino acids at the same positions in the sequence. Conservative substitutions are well known in the art. Examples are isoleucine for leucine, valine for alanine, glutamic acid for aspartic acid, threonine for serine, etc. Typically, a foreign cancer antigen (e.g., proteins or peptides) will possess about 80%, 85%, 90%, 95% or 99% sequence homology. Preferred foreign cancer antigens (e.g., proteins or peptides) are those which are highly homologous, e.g., with from about but less than 100% sequence homology. Particularly preferred foreign cancer antigens (e.g., proteins or peptides) are those wherein the aforementioned sequence homology percents each represent percent sequence identity.

4.2 Viral Antigens Derived from Virus Associated with Cancer

One of the immunotherapeutic agents of the pharmaceutical composition may be one or more antigens derived from a virus associated with cancer. Infection from certain viruses are known to lead to the development of different types of cancers, for example, human papilloma virus (HPV), hepatitis viral infections, Epstein-Barr virus (EBV), human herpes virus 8 (HHV-8), human T-cell leukemia virus-1 (HTLV-1) and human T-cell leukemia virus-2 (HTLV-2).

Patients who are infected or who are at risk of being infected with the human papilloma virus (HPV) are at a higher risk for developing cervical cancer than HPV negative patients. The risk for cervical cancer is particularly high for patients who have HPV-16, HPV-18, HPV-31, HPV-33 and/or HPV-35 infections. The HPV antigen that can be used in the pharmaceutical compositions and the methods of the invention can be an HPV-16 antigen, an HPV-18 antigen, an HPV-31 antigen, an HPV-33 antigen and/or an HPV-35 antigen; and is preferably an HPV-16 antigen and/or an HPV-18 antigen. The genome of HPV-16 is described in *Virology*, 145:181-185 (1985) and DNA sequences encoding HPV-18 are described in U.S. Pat. No. 5,840,306, the disclosures of which are incorporated by reference herein in their entirety. HPV-16 antigens (e.g., seroreactive regions of the E1 and/or E2 proteins of HPV-16) are described in U.S. Pat. No. 6,531,127, and HPV- 18 antigens (e.g., seroreactive regions of the L1 and/or L2 proteins of HPV-18) are described in U.S. Pat. No. 5,840,306, the disclosures of which are incorporated by reference herein. Based on the sequences and antigens for HPV-16 and HPV-18 described in these references, one skilled in the art could develop other HPV antigens using known assays to find appropriate epitopes that generate an effective immune response.

Patients who are infected or are at risk of being infected with hepatitis viral infections, such as hepatitis B (HBV) and/or hepatitis C (HCV) viral infections, are at a higher risk for developing liver cancer than patients who do not have hepatitis viral infections. HBV antigens and HCV antigens can be used in the pharmaceutical compositions and the methods of the invention. The complete genome for HBV is available at GENBANK® Accession No. NC_003977, the disclosure of which is incorporated herein. The genome of HCV is described in European Patent Application No. 318 216, the disclosure of which is incorporated herein. PCT/US90/01348, incorporated by reference herein, discloses sequence information of clones of the HCV genome, amino acid sequences of HCV viral proteins and methods of making and using such compositions for HCV vaccines comprising HCV proteins and peptides derived there from. Based on the sequences and antigens for HBV and HCV described in these references, one skilled in the art could develop other HBV and/or HCV antigens using known assays to find appropriate epitopes that generate an effective immune response.

Patients who are infected or are at risk for being infected with Epstein-Barr virus (EBV) are at a higher risk for developing Burkitt's lymphoma, nasopharyngeal carcinoma and Hodgkin's disease than EBV negative patients. An EBV antigen can be used in the pharmaceutical compositions and the methods of the invention. The nucleotide sequence of EBV DNA is described, for example, in U.S. Pat. No. 4,707,358. Based on this sequences for EBV, one skilled in the art could develop EBV antigens using known assays to find appropriate epitopes that generate an effective immune response. The compounds of the invention, EBV antigens and immunostimulatory compounds can be administered separately or in the form of a composition. The composition can be in the form of a prophylactic vaccine (i.e., for patients who are EBV negative) or therapeutic vaccine (i.e., for patients who are EBV positive).

Patients who are infected or are at risk of being infected with human herpes virus 8 (HHV-8) are at a higher risk for developing Kaposi's sarcoma than HHV-8 negative patients. The HHV-8 antigen can be used in the pharmaceutical compositions and the methods of the invention. The nucleotide sequence of HHV-8 is described, for example, by Russo et al, "Nucleotide sequence of the Kaposi sarcoma-associated herpes virus (HHV8)," *Proc. Natl. Acad. Sci USA*, 93:14862-14867 (1996). Based on the known sequence for HHV-8, one skilled in the art could develop HHV-8 antigens using known assays to find appropriate epitopes that generate an effective immune response.

Patients who are infected or at risk of being infected with human T-cell leukemia virus-1 (HTLV-1) or human T-cell leukemia virus-2 (HTLV-2) are at a higher risk for developing T-cell leukemia than HTLV-1 or HTLV-2 negative patients. The sequences of HTLV-1 and HTLV-2 are well known in the art and are described in Wong-Staal F, Gallo R C. Human T-lymphotropic retroviruses. *Nature* 317:395-403, 1985.

4.3 Anti-Cancer Antibodies

One of the immunotherapeutic agents of the pharmaceutical composition may be one or more anti-cancer antibodies, that is, an antibody that has been generated to one or more cancer antigens. Exemplary anti-cancer antibodies include the following:

trastuzumab (HERCEPTIN® by Genentech) which is used to treat HER-2/neu positive breast cancer or metastatic breast cancer;

bevacizumab (AVASTIN® by Genentech) which is used to treat colorectal cancer, metastatic colorectal cancer, breast cancer, metastatic breast cancer, non-small cell lung cancer, or renal cell carcinoma;

rituximab (RITUXAN® by Genentech), which is used to treat non-Hodgkin's lymphoma or chronic lymphocytic leukemia;

pertuzumab (OMNITARG® by Genentech) which is used to treat breast cancer, prostate cancer, non-small cell lung cancer, or ovarian cancer;

cetuximab (ERBITUX® by ImClone Systems Incorporated) which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer;

IMC-1C11 (ImClone Systems Incorporated) which is used to treat colorectal cancer, head and neck cancer, as well as other potential cancer targets;

tositumomab and tositumomab and iodine $I^{131}$ (BEXXAR® by Corixa Corporation) which is used to treat non-Hodgkin's lymphoma, which can be CD20 positive, follicular, non-Hodgkin's lymphoma, with and without transformation, whose disease is refractory to Rituximab and has relapsed following chemotherapy;

$In^{111}$ ibirtumomab tiuxetan; $Y^{90}$ ibirtumomab tiuxetan; $In^{111}$ ibirtumomab tiuxetan and $Y^{90}$ ibirtumomab tiuxetan (ZEVALIN® by Biogen Idec) which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma;

EMD 7200 (EMD Pharmaceuticals) which is used for treating for treating cancer is non-small cell lung cancer or cervical cancer;

SGN-30 (genetically engineered monoclonal antibody targeted to CD30 antigen by Seattle Genetics) (Hodgkin's lymphoma or non-Hodgkin's lymphoma); SGN-15 (genetically engineered monoclonal antibody targeted to a Lewis$^y$-related antigen that is conjugated to doxorubicin by Seattle Genetics) (non-small cell lung cancer); SGN-40 (humanized monoclonal antibody targeted to CD40 antigen by Seattle Genetics)(multiple myeoloma or non-Hodgkin's lymphoma); SGN-35 (genetically engineered monoclonal antibody targeted to a CD30 antigen that is conjugated to Auristatin E by Seattle Genetics)(non-Hodgkin's lymphoma); SGN-17/19 (fusion protein containing antibody and enzyme conjugated to melphalan prodrug by Seattle Genetics)(melanoma or metastatic melanoma).

The anti-cancer antibody can be a fragment of an antibody; a complex comprising an antibody; or a conjugate comprising an antibody. The antibody can optionally be chimeric or humanized.

The mechanism(s) of action of many of these antibodies are not entirely clear, but generation of an immune response such as antibody-dependent cell-mediated cytotoxicity (ADCC) is often believed to be part of the therapeutic action. Activation of ADCC by TLR4 ligation on Fc receptor-bearing cells may enhance the anti-tumor efficacy of the antibody. The use of the anti-cancer antibodies in combination with one or more compounds selected from formulae (I), (II), (III), (IV), and (V) will increase the immune response.

4.4 Anti-Idiotypic Antibodies

Antibodies to antigens have a serologically unique structure at the antigen-binding site, called an idiotype. An antibody may be generated to the original antibody, resulting in the production of anti-idiotypic antibodies. The original antibody is designated Ab1, and the anti-idiotypic antibody Ab2. The Ab2 antibodies recognize the antigen-binding site of Ab1, and therefore share a motif or structural similarities with the original antigen. An antibody raised to the binding site on Ab2 may therefore react with the original antigen. If the original antigen is a cancer antigen, the anti-Ab2 antibody may have a therapeutic effect.

When administered alone, the anti-idiotypic antibody may not be able to generate sufficient immune response to a cancer antigen. However, when the anti-idiotypic antibody is used in combination with one or more compound selected from formulae (I), (II), (III), (IV), and (V) as a pharmaceutical composition or in a method of administration of this invention, an immune response is generated. The adjuvant compounds of formulae (I), (II), (III), (IV), and (V) can improve the immunogenicity of the anti-idiotypic antibody or provide the anti-idiotypic antibody with the ability to generate an immune response by breaking immunological tolerance. In addition, the pharmaceutical composition of the invention may also reduce the amount of anti-idiotypic antibodies needed to induce an immune response and/or reduce the number of administrations needed to induce the desired immune response.

Anti-idiotypic antibodies are known in the art. The anti-idiotypic antibody may be an antibody to an antibody that that is produced in response to a cancer antigen described above or to an anti-cancer antibody. Exemplary anti-idiotypic antibodies include 105AD7 (described in U.S. Pat. No. 6,042,827, the disclosure of which is incorporated by reference herein in its entirety); BEC2 (ImClone Systems Incorporated); IGN301 (Igeneon, a subsidiary of Aphton Corporation); and the like. The production of anti-idiotypic antibodies are well known in the art and are described for example in U.S. Pat. No. 6,926,893, the disclosure of which is incorporated by reference herein in its entirety.

4.5 Modes of Administration of Pharmaceutical Compositions

Administration of the pharmaceutical composition can be accomplished by several routes that would be suitable for delivery. Exemplary delivery modes include parenteral administration, e.g., subcutaneous injection, transcutaneous, intravenous, intra-tumoral, peri-tumoral, intra-nasal, ophthalmic, intramuscular, intradermal, intraperitoneal, pulmonary, and non-parenteral administration, e.g., transmucosal, transdermal, inhalation, intravaginal, rectal or oral administration.

4.6 Methods of Treatment

The pharmaceutical composition provides a method for stimulating or eliciting or enhancing an immune response in a subject individual. The subject individual is preferably human, although the invention can be applied in veterinary applications to animal species, including mammals or avian species.

The subject individual may be at risk for developing cancer, diagnosed with a cancer, in treatment for cancer, or in post-therapy recovery from cancer.

The term "immune response" encompasses both cellular and humoral immune responses, including stimulating the production of cytokines, stimulating the proliferation of immune cells, stimulating the activation of immune cells, or stimulating the lytic activity of immune cells. Examples of immune responses stimulated by the methods of the invention are the secretion of cytokines, the activation of NK cells, the proliferation of B cells, T cells, macrophages, monocytes, and other immune cells, and other immune responses. To detect a cellular immune response, for example, T cell effector activity against cells expressing the antigen can be detected using standard assays, e.g., target-cell killing, macrophage activation, B-cell activation or lymphokine production. Humoral responses can be measured by detecting the appearance of, or the increase in titer of, for example, antigen-specific antibodies, using routine methods such as ELISA. The progress of the antibody response can be determined by measuring class switching, such as the switch from an early IgM response to a later IgG response.

As used herein, the term "stimulate an immune response" includes stimulating, eliciting, increasing, enhancing, sustaining, and/or improving the stimulation of new immune response or of a preexisting immune response. Thus, "stimulating an immune response" as an immunotherapy refers to enhancing the therapeutic efficacy, increasing survival time, slowing the progression of a cancerous tumor or shrinking the cancerous tumor size, preventing the spread of a tumor or of metastases, preventing or slowing the recurrence of treated cancer, eliminating cancer cells not killed by earlier treatments, targeting potential cancer cells or targeting antigens derived from a virus associated with cancer. In the methods of this invention, the immunotherapeutic agent and the compound of selected from formulae (I), (II), (III), (IV) and (V) are administered in an amount effective to stimulate an immune response in the subject individual at a dose sufficient to generate an effective immune response without unacceptable toxicity. As will be understood by one of skill in the art, the magnitude of the immune response and the maintenance of that response may have varying degrees which will be recognized a having a potential therapeutic or prophylactic benefit.

To stimulate an immune response, the subject individual is administered (i) at least one immunotherapeutic agent selected from one or more cancer antigens, one or more antigens derived from a virus associated with cancer, an anti-cancer antibody, and an anti-idiotypic antibody to an anti-cancer antibody, and (ii) one or more compounds selected from formulae (I), (II), (III), (IV) and (V), and/or a pharmaceutically acceptable salt, hydrate, solvate, stereoisomer, amorphous solid thereof, or any combination thereof. Typically, the administration of the immunotherapeutic agent and the compound of selected from formulae (I), (II), (III), (IV) and (V) will be in the form of a vaccine or administered in a vaccine regimen. The therapeutic agent and the compound of selected from formulae (I), (II), (III), (IV) and (V) can be administered at about the same time to the subject individual, or can be administered separately and/or sequentially. "At about the same time" includes administering one or more immunotherapeutic agents and one or more compounds selected from formulae (I), (II), (III), (IV), and (V) at the same time, at the same time, but through different modes of administration or at different sites on the body, at different times on the same day, or on different days, provided that they are administered as part of an overall dosing treatment regimen. When administered separately, or sequentially, the one or more immunotherapeutic agents and one or more compounds selected from formulae (I), (II), (III), (IV), and (V) are part of an overall treatment regimen, such as a therapeutic cocktail or a combination therapy. The dosing schedule can be routinely determined by one of skill in the art and may be varied or modified according to the appropriate treatment for the subject individual. For example, the immunotherapeutic agent and a compound of formulae (I), (II), (III), (IV) and (V) can be administered at about the same time as a single dose, or by a dose of the therapeutic agent and a dose of a compound of formulae (I), (II), (III), (IV) and (V). The dosing schedule can be continued at regular intervals, such as at 1 to 4 week time periods, followed by dosing at regular intervals of 1 to 3 months, for example. In another embodiment, the dosing schedule can be based on a "prime" and "boost" treatment, in which the immunotherapeutic agent is administered to prime or stimulate the production of CTLs and then another dose of immunotherapeutic agent in combination with one or more compounds selected from formulae (I), (II), (III), (IV), and (V) to boost the production of neutralizing antibodies and antibody dependent cellular cytotoxcity. The immune response in the subject individual can be assessed and monitored through known methods.

In some instance, these treatments can be used in combination with conventional cancer therapies or pharmaceutical formulations useful for treating cancer or infectious diseases. These treatments can include surgical procedures, radiation therapy and/or ablation therapy (e.g., laser therapy, infrared therapy and the like).

Cancer therapies including dendritic cell therapy, chemokines, cytokines, tumor necrosis factors (e.g., TNF-α), chemotherapeutic agents (e.g., adenosine analogs (e.g., cladribine, pentostatin), alkyl sulfanates (e.g., busulfan)), anti-tumoral antibiotics (e.g., bleomycin, dactinomycin, daunorubicin, doxorubicin, epirubicin, idarubicin, mitoxantrone, mitomycin), aziridines (e.g., thiotepa), camptothecin analogs (e.g., irinotecan, topotecan), cryptophycins (e.g., cryptophycin 52, cryptophicin 1), dolastatins (e.g., dolastatin 10, dolastatin 15), enedyine anticancer drugs (e.g., esperamicin, calicheamicin, dynemicin, neocarzinostatin, neocarzinostatin chromophore, kedarcidin, kedarcidin chromophore, C-1027 chromophore, and the like), epipodophyllotoxins (e.g., etoposide, teniposide), folate analogs (e.g., methotrexate), maytansinoids (e.g., maytansinol and maytansinol analogues), microtubule agents (e.g., docetaxel, paclitaxel, vinblastine, vincristine, vinorelbine), nitrogen mustards (e.g., chlorambucil, cyclophosphamide, estramustine, ifosfamide, mechlorethamine, melphalan), nitrosoureas (e.g., carmustine, lamustine, streptoxacin), nonclassic alkylators (e.g., altretamine, dacarbazine, procarbazine, temozolamide), platinum complexes (e.g., carboplatin, cisplatin), purine analogs (e.g., fludarabine, mercaptopurine, thioguanine), pyrimidine analogs (e.g., capecitabine, cytarabine, depocyt, floxuridine, fluorouracil, gemcitabine), substituted ureas (e.g., hydroxyurea)]; anti-angiogenic agents (e.g., canstatin, troponin I,), biologic agents (e.g., ZD 1839, virulizin and interferon ), antibodies and fragments thereof (e.g., anti EGFR, anti-HER-2/neu, anti-KDR, IMC-C225), anti-emetics (e.g., lorazepam, metroclopramide, and domperidone), epithelial growth factor inhibitors (e.g., transforming growth factor beta 1), anti-mucositic agents (e.g., dyclonine, lignocaine, azelastine, glutamine, corticoid steroids and allopurinol), anti-osteoclastic agents (e.g., bisphosphonates {e.g., etidronate, pamidronate, ibandronate, and osteoprotegerin}), hormone regulating agents (e.g., anti-androgens, LHRH agonists, anastrozole, tamoxifen), hematopoietic growth factors, anti-toxicity agents (e.g., amifostine), kinase inhibitors (gefitinib, imatinib), and mixtures of two or more thereof.

Antibodies that block immunosuppressive functions, for example, anti-CTLA4 antibodies that block a receptor on T cells that turns off activation may also be used in combination with the immunotherapeutic agent and a compound of formulae (I), (II), (III), (IV) and (V). Thus, administering the immunotherapeutic agent and a compound of formulae (I), (II), (III), (IV) and (V) with anti-CTLA4 antibodies will increase immune response in the subject individual.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype" or "drug response genotype"). Thus, another aspect of the invention provides methods for tailoring an individual's prophylactic or therapeutic treatment according to that individual's drug response genotype. Pharmacogenomics allows a clinician or physician to target prophylactic or therapeutic treatments to patients who will most benefit from the treatment and to avoid treatment of patients who will experience toxic drug-related side effects. The clinician or physician can thereby tailor the type of treatment that may be necessary to the specific patient.

4.7 Optional Immunostimulatory Compounds

In one embodiment of the methods of immunotherapy, the immune response is further augmented by the administration of compounds that may act as an immunostimulatory compound. Exemplary immunostimulatory compounds include toll like receptor (TLR) agonists (e.g., TLR4, TLR7, TLR9), N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, pegylated G-CSF, SCF, IL-3, IL6, PIXY 321), interferons (e.g., γ-interferon, α-interferon), interleukins (e.g., IL-2, IL-7, IL-12, IL-15, IL-18), MHC Class II binding peptides, saponins (e.g., QS21), unmethylated CpG sequences, 1-methyl tryptophan, arginase inhibitors, cyclophosphamide, antibodies that block immunosuppressive functions (e.g., anti-CTLA4 antibodies), and mixtures of two or more thereof. Exemplary TLR4 agonists include lipopolysaccharides (LPS); E. coli LPS; and P. gingivalis LPS. Exemplary TLR7 agonists include imidazoquinoline compounds (e.g., imiquimod, resiquimod and the like); and loxoribine.

4.8 Pharmaceutical Formulations

The pharmaceutical composition is formulated to be compatible with its intended route of administration, and will typically include a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, (eds. J. Swarbrick and J. C. Boylan), 1988-1999, Marcel Dekker, New York).

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols such as mannitol, sorbitol, and sodium chloride are included in the composition. Prolonged absorption of the injectable compositions can be brought about by including in the composition an agent which delays absorption, for example, aluminum monostearate and gelatin.

Sterile injectable solutions can be prepared by incorporating compound selected from formulae (I), (II), (III), (IV), and (V) in the specified amount in an appropriate solvent with one or a combination of ingredients enumerated above, as needed, followed by filtered sterilization. Generally, dispersions are prepared by incorporating the active compound into a sterile vehicle, which contains a basic dispersion medium and other ingredients selected from those enumerated above or others known in the art. In the case of sterile powders for the preparation of sterile injectable solutions, the methods of preparation can be vacuum drying and freeze-drying, which yields a powder of the active ingredient plus any additional desired ingredient from a previously sterile-filtered solution thereof.

4.9 Covalent Bonding, Complexes and Conjugates

In one embodiment, one or more immunotherapeutic agent and a compound selected from formulae (I), (II), (III), (IV), and (V) can be covalently bonded together through an alkyl, amino, carbonyl, ether, hydroxyl, phosphate, phosphonyl, sulfonyl, sulfate, thiol ether, or thiol moiety of compound selected from formulae (I), (II), (III), (IV), and (V). For example, one or more immunotherapeutic agent can be covalently bonded to the $R^1$, $X^1$ and/or $Y^1$ substituents in the compounds selected from formulae (I), (II), (III), (IV), and (V). For example, the immunotherapeutic agent can be covalently bonded to a carbonyl moiety (e.g., the $C_1$ carbonyl) of the —C(O)— group or to the —C(O)—$C_{1-14}$alkyl-C(O)— group of the $R^1$ substituent in one or more compounds of the invention. As another example, the immunotherapeutic agent can be covalently bonded through a nitrogen atom in the $X^1$ and/or $Y^1$ substituents in the compound selected from formulae (I), (II), (III), (IV), and (V). One skilled in the art would be able to link one or more immunotherapeutic agent to a compound selected from formulae (I), (II), (III), (IV), and (V) following the methods described, for example, by Hoffman et al., Biol. Chem. Hoppe-Sayler, 370:575-582 (1989); Wiesmuller et al., Vaccine, 7:29-33 (1989); Wiesmuller et al., Int. J. Peptide Protein Res., 40:255-260 (1992); Defourt et al., Proc. Natl. Acad. Sci., 89:3879-3883 (1992); Tohokuni et al., J. Am. Chem. Soc., 116:395-396 (1994); Reichel, Chem. Commun., 2087-2088 (1997); Kamitakahara, Agnew. Chem. Int. Ed. 37:1524-1528 (1998); Dullenkopf et al., Chem. Eur. J., 5:2432-2438 (1999); the disclosures of which are incorporated by reference herein in their entirety.

In one embodiment, the immunotherapeutic agent can be in the form of a complex. The complex can comprise at least one cancer antigen (optionally bonded to the compound selected from formulae (I), (II), (III), (IV), and (V)) and one or more proteins, peptides, immunostimulatory compounds and/or cells. Exemplary proteins and peptides include heat shock proteins, heat shock peptides, MHC Class I proteins, MHC Class I peptides, MHC Class II proteins, MHC Class II peptides, and the like. Exemplary cells include dendritic cells, autologous dendritic cells, dendritic cells pulsed with cancer antigens, autologous dendritic cells pulsed with cancer antigens, and the like. Exemplary immunostimulatory compounds include TLR agonists (e.g., TLR4, TLR7, TLR9), N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., γ-interferon, α-interferon), interleukins (e.g., IL-2, IL-7, IL-12, IL-15, IL-18), saponins (e.g., QS21), monophosphoryl lipid A, 3 De-O-acylated monophosphoryl lipid A (3D-MPL), unmethylated CpG sequences, 1-methyl tryptophan, arginase inhibitors, cyclophosphamide, antibodies that block immunosuppressive functions (e.g., anti-CTLA4 antibodies), and the like. The complex with at least one cancer antigen (optionally bonded to compound selected from formulae (I), (II), (III), (IV), and (V)) and the proteins, peptides, immunostimulatory compounds and/or cells can be non-covalent, ionic, covalent, van der Waals' forces, hydrogen bonding, and the like.

In another embodiment, the cancer antigen (optionally bonded to compound selected from formulae (I), (II), (III), (IV), and (V)) is in the form of a complex comprising a heat shock protein or heat shock peptide (HSP), particularly gp96. In one embodiment, the complex is formed by in vitro peptide pulsing the heat shock proteins and/or heat shock peptides. The complex can be covalent or non-covalent. In another embodiment, the cancer antigen (optionally bonded to compound selected from formulae (I), (II), (III), (IV), and (V)) is in the form of a complex comprising a peptide, at least one heat shock protein and/or heat shock peptide, and at least one MHC Class I and/or II protein or peptide.

In another embodiment, the cancer antigen (optionally bonded to compound selected from formulae (I), (II), (III), (IV), and (V)) is in the form of a complex comprising a peptide and dendritic cells. In one embodiment, the complex is formed by in vitro peptide pulsing the dendritic cells to form cancer antigen loaded dendritic cells. The dendritic cells can be pulsed with cancer antigens and/or organisms (e.g., recombinant viruses or bacteria) expressing cancer antigens. The dendritic cells can be autologous.

In another embodiment, the cancer antigen (optionally bonded to compound selected from formulae (I), (II), (III), (IV), and (V)) is in the form of a complex comprising a peptide and an MHC Class I protein or peptide; and/or comprising a peptide and a MHC Class II protein or peptide. In one embodiment, the MHC Class I protein or peptide is HLA (e.g., HLA-A*0201, HLA-A2, HLA-A3, HLA-A*1101, HLA-A*3101, HLA-A*3301, HLA-A*6801, HLA-A24). The complex can be covalent or non-covalent. In another embodiment, the cancer antigen (optionally bonded to compound selected from formulae (I), (II), (III), (IV), and (V)) is in the form of a complex comprising a peptide, a MHC Class I and/or II protein or peptide, and at least one heat shock protein and/or heat shock peptide.

In another embodiment, the cancer antigen is in the form of a conjugate. For example, one or more cancer antigens can be chemically linked to one or more proteins, peptides, carbohydrates, polymers, lipids and/or toxic moieties. The conjugate can be of the formula: A-L-X, wherein "A" is one or more cancer antigens as described herein, "L" is one or more linking groups, and "X" is one or more proteins, peptide, carbohydrates, polymers, lipids and/or toxic moieties. Exemplary linking groups include chemical linking groups and peptide linking groups. The most common methods for linking "A" and "X" rely on the presence of free amino (α-amino or Lys), sufhydryl (Cys), or carboxylic acid groups (Asp, Glu, or α-carboxyl). Linking methods should be used that link the peptides to the carrier proteins, peptides, carbohydrates, lipids and/or toxic moieties via the carboxy- or amino-terminal residue. Other common linking methods include maleimide and carbodiimide coupling chemistry. The linking group can be selected so that enzymes act upon the linking group so that "A" and "X" separate from each other in vivo. Alternatively, a linking group can be selected so that "A" and "X" remain covalently bonded via the linking group in vivo. In still other embodiments, "L" can simply be a covalent bond between "A" and "X." "X" can be a peptide, protein (such as an MHC Class I protein or an MHC Class II protein); keyhole limpet hemocyanin; albumin; bovine serum albumin; ovalbumin; rabbit serum albumin, antibody and the like. "X" can be a peptide. The peptide can be cancer antigen that is the same as or different from "A." Such a conjugate may be referred to as a multiple antigen peptide (MAP), and the peptides can form a fusion protein with or without the presence of a linking group "L." The peptide can be a Class I and/or Class II peptide that can assist in generating an immune response. One skilled in the art will appreciate that the term "fusion protein" may be used when two peptides are linked together, in which case the "L" group may drop out of the structure. In other embodiments, "X" can be a toxic moiety. Exemplary toxic moieties include viral toxins, bacterial toxins (e.g., diphtheria toxins, tetanus toxins, clostridia toxin, cholera toxin, anthrax toxin, botulinum toxin, pertussis toxin, tracheal toxin, 5. Compounds of Formulae (I), (II), (III), (IV) and (V)

The pharmaceutical compositions include the immunotherapeutic agents described above and a compound selected from formulae (I), (II), (III), (IV), and (V) and/or a pharmaceutically acceptable salt, hydrate, solvate, stereoisomer, amorphous solid thereof, or any combination thereof.). The compounds of Formula (I), (II), (III), (IV) and (V) can function as adjuvants and/or as immunostimulatory compounds depending on the application in which they are used.

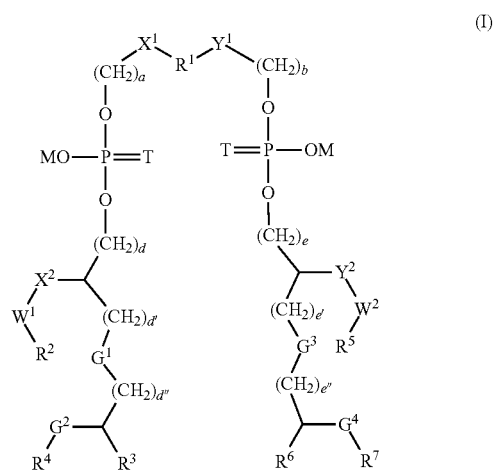

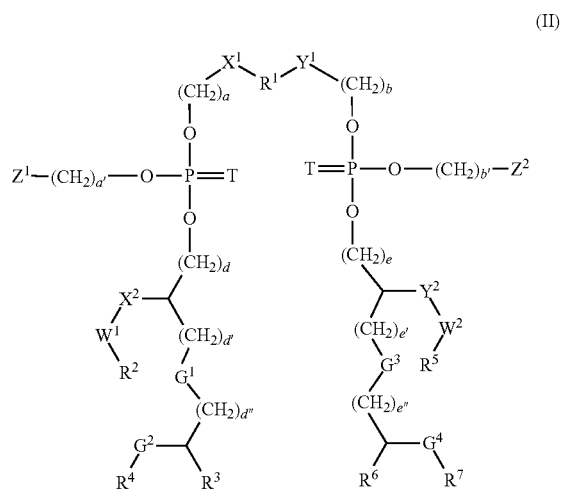

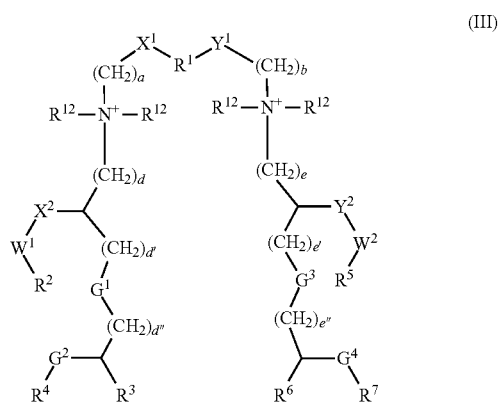

-continued

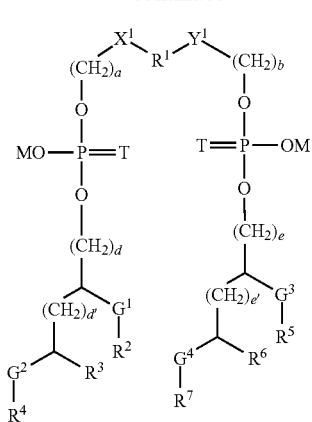

(IV)

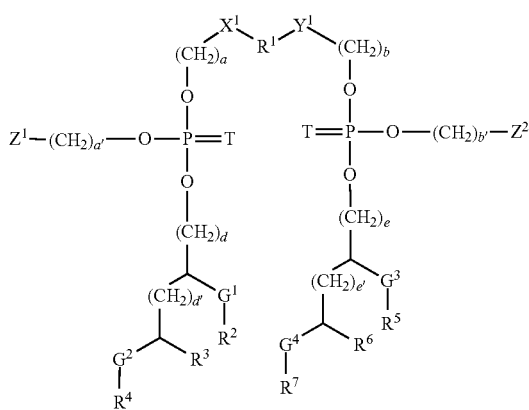

(V)

wherein:

R[1] is: (a) —C(O)—;
(b) —C(O)—C$_{1-14}$alkyl-C(O)— or —C(O)—C$_{1-14}$alkenyl-C(O)—;
  wherein the —C$_{1-14}$alkyl- or —C$_{1-14}$alkenyl- is optionally substituted with one or more substituents selected from hydroxy, C$_{1-6}$alkyl, C$_{1-6}$alkoxy, C$_{1-6}$alkyldioxy, C$_{1-5}$ alkylamino, carboxy, C$_{1-6}$ alkoxycarbonyl, C$_{1-6}$ carbamoyl, C$_{1-6}$ acylamino, and/or (aryl)C$_{1-6}$alkyl; and
  wherein the aryl moiety of the (aryl)C$_{1-6}$-alkyl is optionally substituted with one or more substituents selected from C$_{1-6}$alkyl, C$_{1-6}$alkoxy, C$_{1-6}$alkylamino, C$_{1-6}$alkoxyamino, C$_{1-6}$alkylamino-C$_{1-6}$alkoxy, —O—C$_{1-6}$alkylamino-C$_{1-6}$alkoxy, —O—C$_{1-6}$alkylamino-C(O)—C$_{1-6}$alkyl-C(O)OH, —O—C$_{1-6}$alkylamino-C(O)—C$_{1-6}$alkyl-C(O)—C$_{1-6}$alkyl, —O—C$_{1-6}$alkyl-NH—C$_{1-6}$alkyl-O—C$_{1-6}$ alkyl, —O—C$_{1-6}$alkyl-NH—C(O)C$_{1-6}$alkyl-C(O)OH, and/or —O—C$_{1-6}$alkyl-NH—C(O)C$_{1-6}$alkyl-C(O)—C$_{1-6}$alkyl;
(c) a C$_2$ to C$_{15}$ straight or branched chain alkyl group optionally substituted with one or more hydroxy and/or alkoxy groups; or
(d) —C(O)—C$_{6-12}$aryl-C(O)— wherein the aryl is optionally substituted with one or more hydroxy, halo (e.g., fluoro), nitro, amino, C$_{1-6}$alkyl and/or C$_{1-6}$alkoxy groups;

a and b are each independently 0, 1, 2, 3 or 4; (preferably 2);
a' and b' are independently 2, 3, 4, 5, 6, 7 or 8; (preferably 2);
d and e are each independently 1, 2, 3, 4, 5 or 6;
d' and e' are each independently 0, 1, 2, 3 or 4; (preferably 0, 1 or 2);
d" and e" are each independently 0, 1, 2, 3 or 4; (preferably 1, 2, 3 or 4);
T is oxygen or sulfur;
X[1], X[2], Y[1] and Y[2] are each independently null, oxygen, NH, —N(C(O)C$_{1-4}$alkyl)-, or —N(C$_{1-4}$alkyl)-;
W[1] and W[2] are each independently carbonyl, methylene, sulfone or sulfoxide;
R[2], R[3], R[4], R[5], R[6] and R[7] are each independently:
  (a) C$_2$ to C$_{20}$ straight chain or branched chain alkyl, which is optionally substituted with one or more oxo, halo (preferably fluoro), hydroxy and/or alkoxy groups;
  (b) C$_2$ to C$_{20}$ straight chain or branched chain alkenyl, which is optionally substituted with one or more of oxo, halo (preferably fluoro), hydroxy and/or alkoxy groups;
  (c) C$_2$ to C$_{20}$ straight chain or branched chain alkoxy, which is optionally substituted with one or more halo (e.g., fluoro), hydroxy and/or alkoxy groups;
  (d) —NH—C$_{2-20}$ straight chain or branched chain alkyl, wherein the alkyl group is optionally substituted with one or more oxo, halo (e.g., fluoro), hydroxy and/or alkoxy groups;
  (e) —C(O)—C$_{2-20}$ straight chain or branched chain alkyl or alkenyl, wherein the alkyl or alkenyl is optionally substituted with one or more oxo, halo (e.g., fluoro), hydroxy and/or alkoxy groups;
  (f)

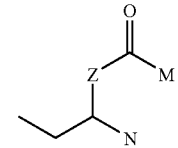

Z is O or NH; and M and N are each independently C$_2$ to C$_{20}$ straight chain or branched chain alkyl, alkenyl, alkoxy, acyloxy, alkylamino, or acylamino;
  (g)

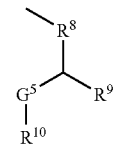

R[8] is C$_{1-6}$ straight or branched chain alkyl or C$_{2-6}$ straight or branched chain alkenyl or alkynyl;

$R^9$ and $R^{10}$ are independently selected from the group consisting of
(i) $C_1$ to $C_{20}$ straight chain or branched chain alkyl, which is optionally substituted with one or more halo, oxo, hydroxy and/or alkoxy; and
(ii) $C_2$ to $C_{20}$ straight chain or branched chain alkenyl or alkynyl which is optionally substituted with one or more halo, oxo, hydroxy and/or alkoxy;

$G^1$, $G^2$, $G^3$, $G^4$ and $G^5$ are each independently oxygen, methylene, —NH—, thiol, —N($C_{1-4}$alkyl)-, —N[C(O)—$C_{1-4}$alkyl]-, —NH—C(O)—, —NH—SO$_2$—, —C(O)—O—, —C(O)—NH—, —O—C(O)—, —O—C(O)NH—, —O—C(O)O—, —NH—C(O)—NH—, —C(O)NH—, —C(O)N($C_{1-4}$alkyl), aryl, and —S(O)$_n$—, where n is 0, 1, or 2;
or $G^1R^2$, $G^2R^4$, $G^3R^5$ and/or $G^4R^7$ may together be a hydrogen atom or hydroxyl;
$Z^1$ and $Z^2$ are each independently selected from —OP(O)(OH)$_2$, —P(O)(OH)$_2$, —OP(O)(OR$^8$)(OH) {where $R^8$ is a $C_{1-4}$alkyl}, —OS(O)$_2$OH, —S(O)$_2$OH—, —CO$_2$H, —OB(OH)$_2$, —OH, —CH$_3$, —NH$_2$, and —N($R^9$)$_2$ {where $R^9$ is a $C_{1-4}$alkyl};
$R^{12}$ is H or a $C_{1-4}$ straight or branched alkyl; and
M is independently selected from a hydrogen atom and a pharmaceutically acceptable cation {a monovalent cation will take the place of one M, while a divalent cation will take the place of two M variables}.

In one embodiment, $R^1$ in the compounds of Formula (I)-(V) is —C(O)— or —C(O)—$C_{1-14}$alkyl-C(O)—. In another embodiment, $R^1$ in the compounds of Formula (I)-(V) is —C(O)—.

In one embodiment of the invention, T is oxygen in the compounds of Formula (I)-(V).

In another embodiment, $G^1$, $G^2$, $G^3$ and $G^4$ in the compounds of Formula (I)-(V) are each independently oxygen, —NH—, —NH—C(O)—, —C(O)—O—, —C(O)NH—, —O—C(O)—, —O—(O)NH—, —O—C(O)—O—, —NH—C(O)—NH—, or —C(O)NH—. In another embodiment, $G^1$, $G^2$, $G^3$ and $G^4$ in the compounds of Formula (I)-(V) are each independently oxygen, —C(O)—O— or —O—C(O)—. In another embodiment, $G^1$ and $G^3$ in the compounds of Formula (I)-(V) are —O—C(O)—.

In one embodiment for the compounds of Formula (I)-(V) {preferably compounds of Formula (I)-(III)}, $R^2$ and $R^5$ are each independently substituents selected from (a), (b), (c), (d) and (f) in the definitions of $R^2$ and $R^5$ herein; $R^3$ and $R^6$ are each independently substituents selected from (a) and (b) in the definitions of $R^3$ and $R^6$ herein; and $R^4$ and $R^7$ are each independently substituents selected from (a), (b), (c) and (e) in the definitions of $R^4$ and $R^7$ herein.

In other embodiments for the compounds of Formula (I)-(V) {preferably compounds of Formula (IV) or (V)}, $R^2$, $R^3$, $R^4$, $R^5$, $R^6$ and $R^7$ are each independently substituents selected from (a), (b), (g) and (h) in the definitions of $R^2$, $R^3$, $R^4$, $R^5$, $R^6$ and $R^7$ herein.

In other embodiments for the compounds of Formulas (I)-(III), one or more of the following is present: each of a and b is 2; each of $X^1$ and $Y^1$ is NH; $R^1$ is —C(O)— or —C(O)—$C_{1-14}$alkyl-C(O)—; each of d' and e' is 1; each of d" and e" is 1; X is O or NH, more preferably NH; and W is C(O); or each of d' and e' are 2.

In other embodiments for Formulas (I)-(III), $R^1$ is a —C(O)$C_{1-14}$ alkyl-C(O)—, wherein the $C_{1-14}$alkyl is substituted, for example, with a $C_{1-5}$alkoxy group.

In one embodiment, the compounds of Formulas (I)-(III) are "Type 1" wherein the values of a and b are the same; the values of d and e are the same; the values of d' and e' are the same; the values of d" and e" are the same; $X^1$ and $Y^1$ are the same; $X^2$ and $Y^2$ are the same; $W^1$ and $W^2$ are the same; $R^2$ and $R^5$ are the same; $G^1$ and $G^3$ are the same; $R^3$ and $R^6$ are the same; $G^2$ and $G^4$ are the same; and $R^4$ and $R^7$ are the same.

In another embodiment, the compounds of Formulas (I)-(III) are "Type 2" wherein the values of a and b are different, the values of d and e are the same, the values of d' and e' are different; the values of d" and e" are the same; $X^1$ and $Y^1$ are different; $X^2$ and $Y^2$ are different; $W^1$ and $W^2$ are different; $R^2$ and $R^5$ are different; $G^1$ and $G^3$ are different; $R^3$ and $R^6$ are different; $G^2$ and $G^4$ are different; or $R^4$ and $R^7$ are different.

In another embodiment, the compounds of Formulas (I)-(III) are "Type 3" wherein the values of a and b are different, the values of d and e are different, the values of d' and e' are different; the values of d" and e" are different; $X^1$ and $Y^1$ are different; $X^2$ and $Y^2$ are different; $W^1$ and $W^2$ are different; $R^2$ and $R^5$ are different; $G^1$ and $G^3$ are different; $R^3$ and $R^6$ are different; $G^2$ and $G^4$ are different; or $R^4$ and $R^7$ are different.

In other embodiments, the compounds of Formulas (I), (II) and/or (III) are preferably:

ER 803022; a pharmaceutically acceptable salt thereof other than the sodium salt shown below; and/or the one or more sodium cations shown below can be replaced with hydrogen atoms:

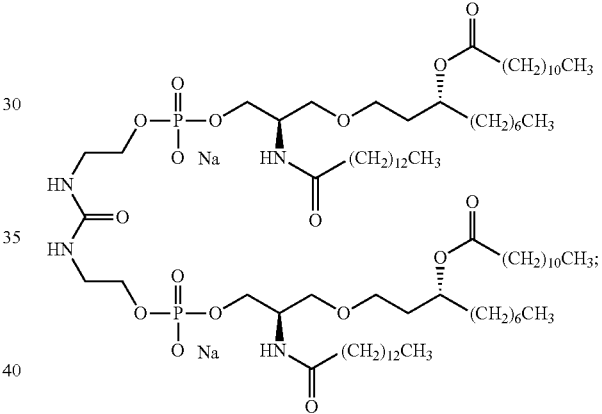

ER 803058; a pharmaceutically acceptable salt thereof other than the sodium salt shown below; and/or the one or more sodium cations shown below can be replaced with hydrogen atoms:

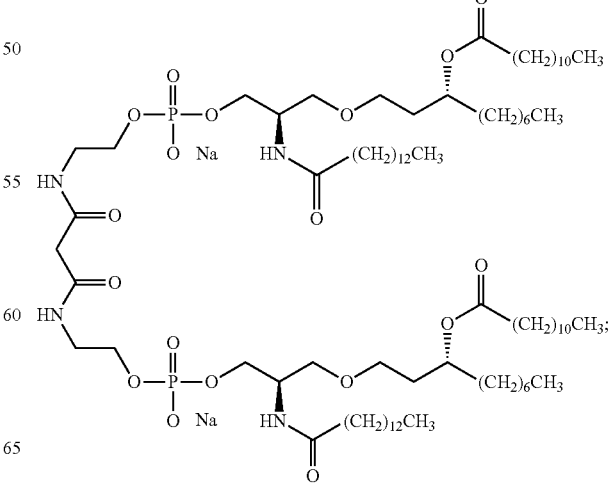

ER 803732; a pharmaceutically acceptable salt thereof other than the sodium salt shown below; and/or the one or more sodium cations shown below can be replaced with hydrogen atoms:

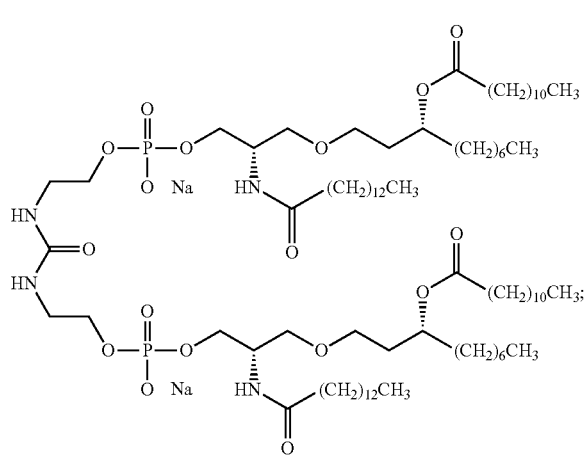

ER 804053; a pharmaceutically acceptable salt thereof other than the sodium salt shown below; and/or the one or more sodium cations shown below can be replaced with hydrogen atoms:

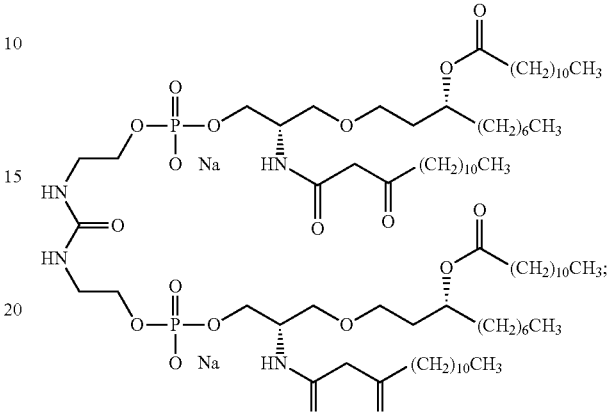

ER 804058; a pharmaceutically acceptable salt thereof other than the sodium salt shown below; and/or the one or more sodium cations shown below can be replaced with hydrogen atoms:

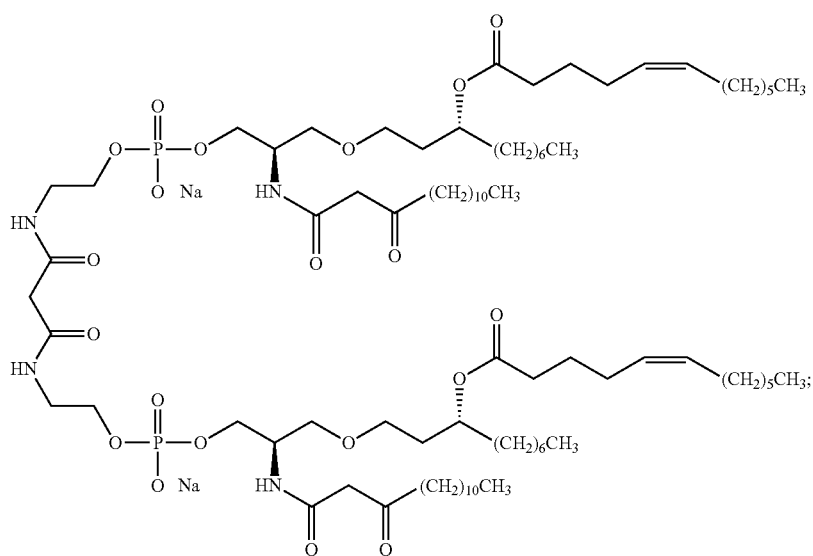

ER 804059; a pharmaceutically acceptable salt thereof other than the sodium salt shown below; and/or the one or more sodium cations shown below can be replaced with hydrogen atoms:

ER 804764; a pharmaceutically acceptable salt thereof other than the sodium salt shown below; and/or the one or more sodium cations shown below can be replaced with hydrogen atoms:

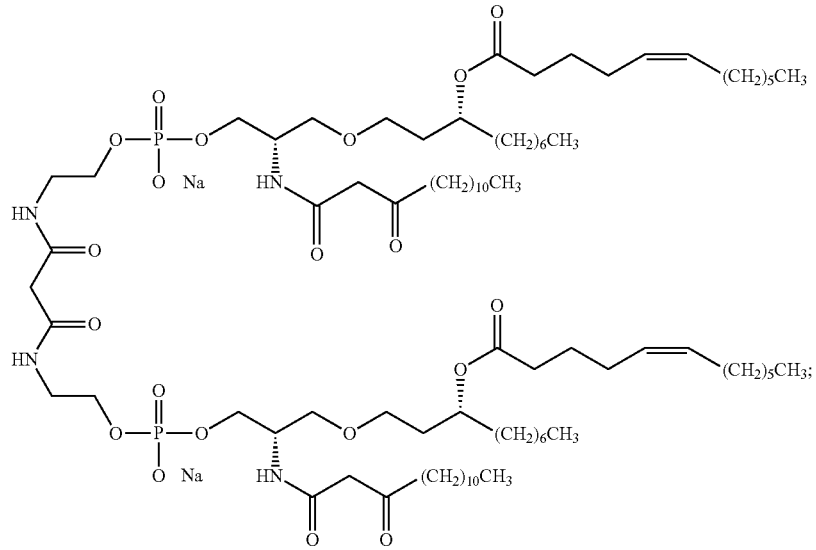

ER 804442; a pharmaceutically acceptable salt thereof other than the sodium salt shown below; and/or the one or more sodium cations shown below can be replaced with hydrogen atoms:

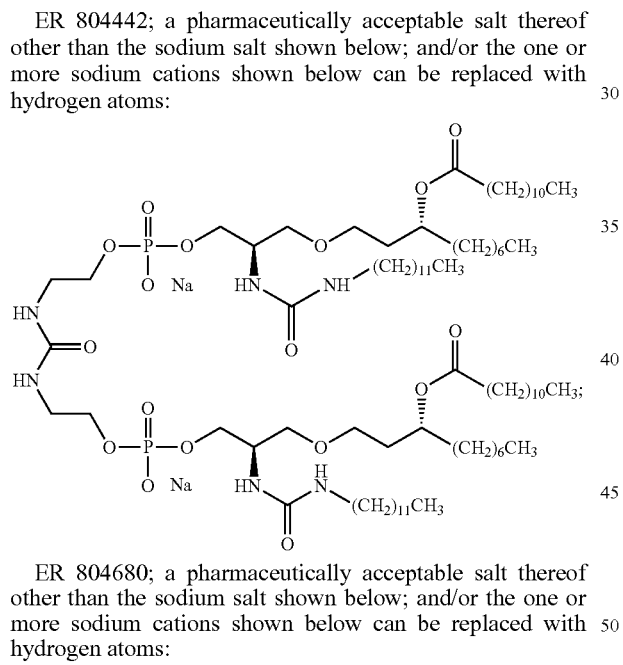

ER 804680; a pharmaceutically acceptable salt thereof other than the sodium salt shown below; and/or the one or more sodium cations shown below can be replaced with hydrogen atoms:

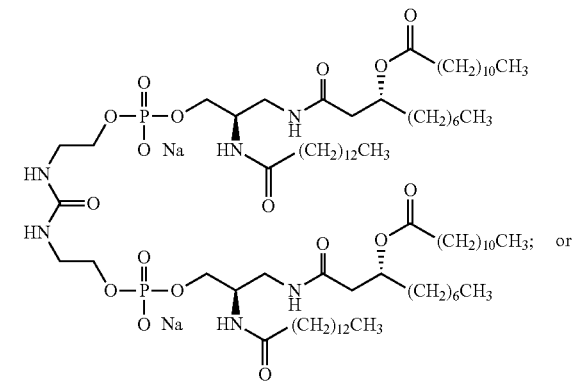

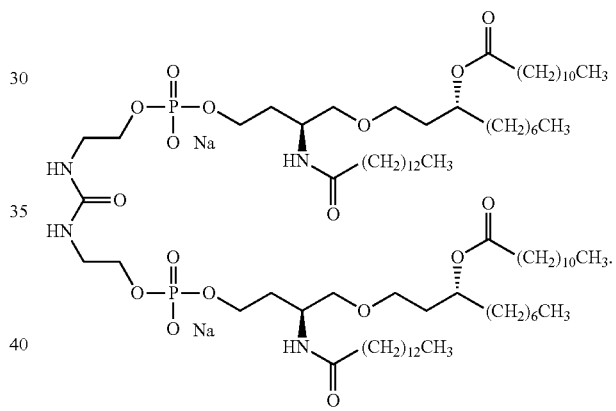

In one embodiment, the preferred compound is 112066; a stereoisomer thereof; a pharmaceutically acceptable salt thereof other than the sodium salt shown below; and/or the one or more sodium cations shown below can be replaced with hydrogen atoms:

In one embodiment, the preferred compound is ER 804057; a pharmaceutically acceptable salt thereof other than the sodium salt shown below; or the one or more sodium cations shown below can be replaced with hydrogen atoms:

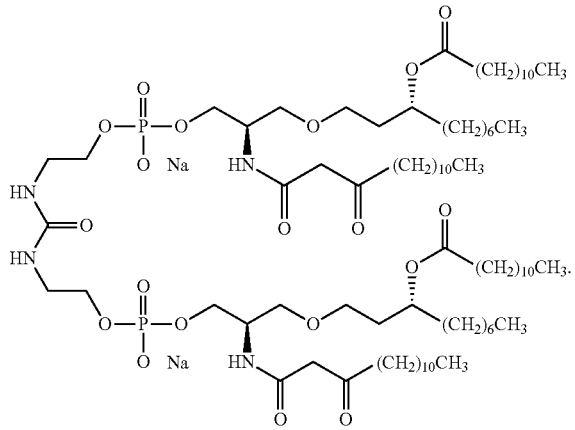

In some embodiments for Formulas (IV) and (V), one or more of the following limitations is present: each of a and b is 2; each of $X^1$ and $Y^1$ is NH; each of d and e is 1 or 2; and each of d' and e' is 0, 1, or 2. In certain preferred embodiments, each of d and e is 1 and each of d' and e' is 0. In certain other preferred embodiments, each of d and e is 1 and each of d' and e' is 1 or 2.

In some embodiments for Formulas (IV) and (V), $R^1$ is —C(O)— or —C(O)—$C_{1-14}$alkyl-C(O)—, wherein the $C_{1-14}$alkyl is optionally substituted with one or two substituents selected from the group consisting of hydroxy, $C_{1-6}$alkoxy, $C_{1-6}$alkyldioxy, $C_{1-6}$alkylamino, or (aryl)$C_{1-6}$alkyl, wherein the aryl moiety of the (aryl)$C_{1-6}$alkyl is optionally substituted with $C_{1-6}$alkyl, $C_{1-6}$alkoxy, $C_{1-6}$alkylamino, ($C_{1-6}$alkoxy)$C_{1-6}$alkylamino, ($C_{1-6}$alkylamino)$C_{1-6}$alkoxy, —O—$C_{1-6}$alkyl-NH—$C_{1-6}$alkyl-O—$C_{1-6}$alkyl, —O—$C_{1-6}$alkyl-NH—C(O)—$C_{1-6}$alkyl-C(O)OH, or —O—$C_{1-6}$alkyl-NH—C(O)—$C_{1-6}$alkyl-C(O)—$C_{1-6}$alkyl.

In some embodiments for Formulas (IV) and (V), $G^1$, $G^2$, $G^3$, and $G^4$ are each independently selected from the group consisting of —NH—C(O)— and —O—C(O)—.

In some embodiments for Formula (IV) and (V), at least two of $R^2$, $R^3$, $R^4$, $R^5$, $R^6$, $R^7$, $R^9$ and $R^{10}$ are $C_{6-20}$ straight or branched chain alkyl, alkenyl, or alkynyl; any of which may optionally be substituted with one or more substituents selected from the group consisting of halo, oxo, hydroxy and/or alkoxy. In other embodiments, at least two of $R^2$, $R^3$, $R^4$, $R^5$, $R^6$, $R^7$, $R^9$ and $R^{10}$ are $C_{8-15}$ straight or branched chain alkyl, alkenyl, or alkynyl; any of which may optionally be substituted with one or more substituents selected from the group consisting of halo, oxo, hydroxy and alkoxy.

In some embodiments for Formulas (IV) and (V), at least four of $R^2$, $R^3$, $R^4$, $R^5$, $R^6$, $R^7$, $R^9$ and $R^{10}$ are $C_{6-20}$ straight or branched chain alkyl, alkenyl or alkynyl; any of which may optionally be substituted with one or more substituents selected from the group consisting of halo, oxo, hydroxy and alkoxy. In certain preferred embodiments, at least four of $R^2$, $R^3$, $R^4$, $R^5$, $R^6$, $R^7$, $R^9$ and $R^{10}$ are $C_{8-15}$ straight or branched chain alkyl, alkenyl or alkynyl; any of which may optionally be substituted with one or more substituents selected from the group consisting of halo, oxo, hydroxy and alkoxy.

In some embodiments for Formulas (IV) and (V), at least six of $R^2$, $R^3$, $R^4$, $R^5$, $R^6$, $R^7$, $R^9$ and $R^{10}$ are $C_{6-20}$ straight or branched chain alkyl, alkenyl, or alkynyl; any of which may optionally be substituted with one or more substituents selected from the group consisting of halo, oxo, hydroxy and alkoxy. In other embodiments, at least six of $R^2$, $R^3$, $R^4$, $R^5$, $R^6$, $R^7$, $R^9$ and $R^{10}$ are $C_{8-15}$ straight or branched chain alkyl, alkenyl or alkynyl; any of which may optionally be substituted with one or more substituents selected from the group consisting of halo, oxo, hydroxy and alkoxy.

In other embodiments, the invention provides compounds of Formula (I), (II), (III), (IV) or (V) wherein T is sulfur. In other embodiments, the invention provides compounds of Formula (I), (II), (III), (IV) or (V) wherein T is sulfur; provided that the compound is not Compound No. 804678.

In another embodiment of the invention, there is a proviso that the compounds of Formula (I), (II) or (III) are not:

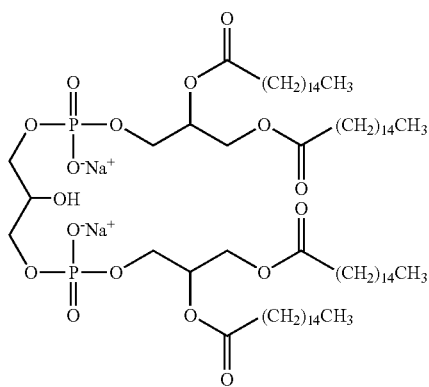

or

-continued

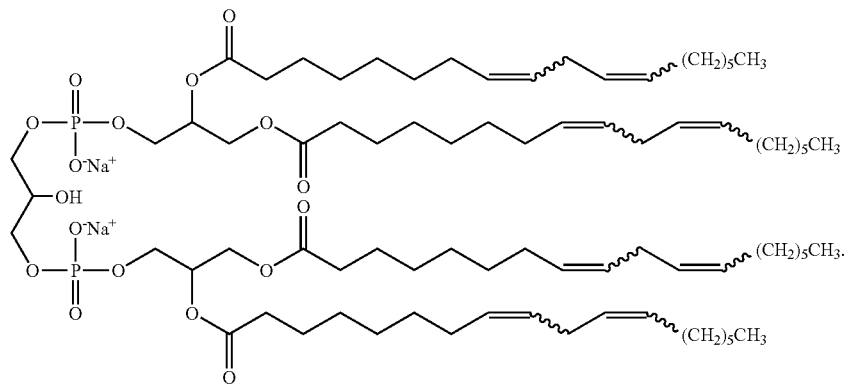

As used herein, the term "alkyl" includes substituted or unsubstituted, straight or branched chain monovalent or bivalent aliphatic hydrocarbon groups. One skilled in the art will appreciate the distinction between a monovalent alkyl group and a bivalent alkyl group in view of the context of the term "alkyl" in the definition for any particular substituent. When an alkyl is a terminal group, it will be monovalent, such as —$CH_3$, —$CH_2CH_3$, —$CH_2CH_2CH_3$, —$CH_2CH_2CH_2CH_3$, and the like. When an alkyl is between other moieties, such as "—C(O)—$C_{1-14}$alkyl-C(O)—" in the definition of $R^1$, the alkyl group will be bivalent, such as —$CH_2$—, —$CR_2CH_2$—, —$CH_2CH_2CH_2$—, —$CH_2CH_2CH_2CH_2$—, and the like.

As used herein, the term "alkenyl" includes substituted or unsubstituted, straight or branched chain unsaturated monovalent or bivalent aliphatic hydrocarbon groups. The "alkenyl" group can have any number of carbon-carbon double bonds, preferably one or two. One skilled in the art will appreciate the distinction between a monovalent alkenyl group and a bivalent alkenyl group in view of the context of the term "alkenyl" in the definition for any particular substituent. When an alkenyl is a terminal group, it will be monovalent, such as —CH=$CH_2$, —CH=$CHCH_3$, and the like. When an alkenyl is between other moieties, such as "—C(O)—$C_{1-14}$alkenyl-C(O)—" in the definition of $R^1$, the alkenyl group will be bivalent, such as —CH=CH—, —CH=$CHCH_2$—, —$CH_2$CH=$CHCH_2$—, and the like.

As used herein, the term "aryl" includes substituted or unsubstituted, monovalent or bivalent aromatic hydrocarbon groups. One skilled in the art will appreciate the distinction between a monovalent aryl group and a bivalent aryl group in view of the context of the term "aryl" in the definition for any particular substituent. When an aryl is a terminal group, it will be monovalent. When an aryl is between other moieties, such as "—C(O)—$C_{6-12}$aryl-C(O)—" in the definition of $R^1$, the aryl group will be bivalent.

Boc is t-butyloxycarbonyl.

Null with reference to a given substituent means that the substituent is absent, and the chemical groups between which the substituent is positioned are directly attached to each other by way of a covalent bond.

The compounds of Formulas (I), (II), (III), (IV) and (V) may have one or more asymmetric carbon atoms, depending upon the substituents, and can have stereoisomers, which are within the scope of the invention. The compounds of Formulas (I), (II), (III), (IV) and/or (V) can be administered in the form of a pharmaceutically acceptable salt (e.g., where M in the compounds of Formulas (I), (II), (III), (IV) and/or (V) is a pharmaceutically acceptable cation). The compounds of Formulas (I), (II), (III), (IV) and/or (V) can be administered in the form of a pharmaceutically acceptable salt of a stereoisomer of the compounds. "Pharmaceutically acceptable salt" refers to salts which retain their biological effectiveness. Pharmaceutically acceptable base addition salts can be prepared from inorganic and organic bases. Exemplary pharmaceutically acceptable salts derived from inorganic bases include sodium, potassium, lithium, ammonium, calcium and magnesium salts. Exemplary salts derived from organic bases include salts of primary, secondary and tertiary amines. Pharmaceutically acceptable acid addition salts may be prepared from inorganic and organic acids. Exemplary salts derived from inorganic acids include hydrochloric acid, hydrobromic acid, sulfuric acid, nitric acid, phosphoric acid, and the like. Exemplary salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Methods for making the compounds of Formulas (I), (II), (III), (IV) and (V) are described in US Publication No. 2004/0006242, US Publication No. 2003/0153532, US Publication No. 2002/0176861, US Publication No. 2002/0049314, U.S. Pat. Nos. 6,551,600, 6,521,776, 6,290,973, and WO 03/099195, the disclosures of which are incorporated by reference herein in their entirety. Some compounds of Formulas (I), (II), (III), (IV) and (V) and methods for making them are also described by Hawkins et al, *The Journal of Pharmacology and Experimental Therapeutics,* 300(2):655-661 (2000); Lien et al, *The Journal of Biological Chemistry,* 276(3):1873-1880 (2001); Przetak et al, *Vaccine,* 21:961-970 (2003); and Seydel et al, *Eur. J. Immunol.,* 33:1586-1592 (2003), the disclosures of which are incorporated by reference herein in their entirety.

Exemplary compounds falling within the scope of the compounds of Formulas (I)-(V) are set forth below.

| No. | Structure |
|---|---|
| 112022 | 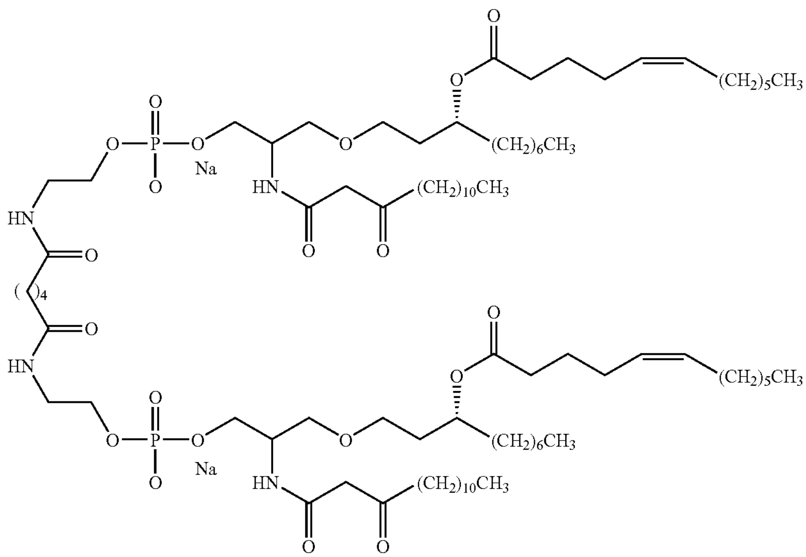 |
| 111230 | 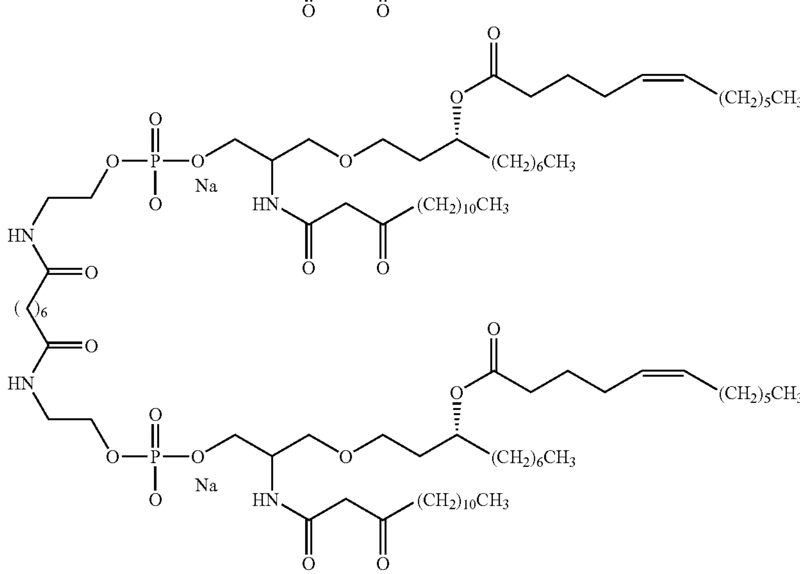 |
| 111231 | 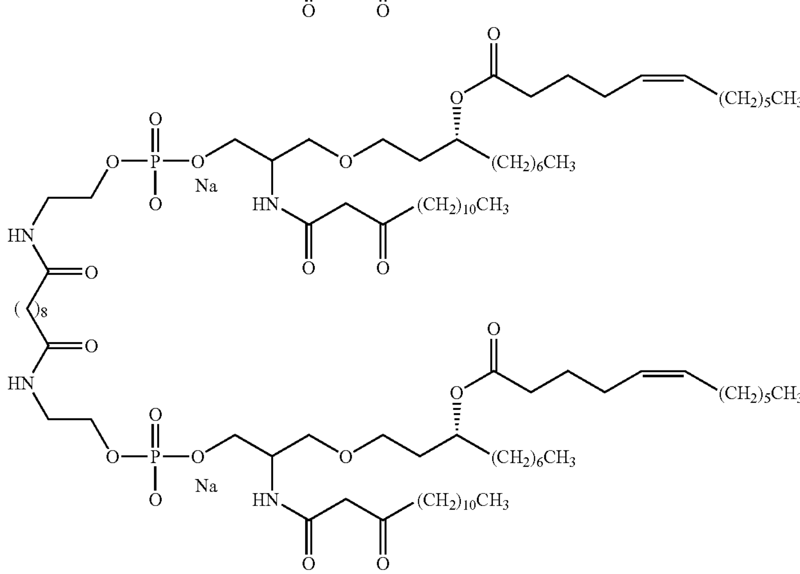 |

-continued
| No. | Structure |
|---|---|
| 111232 | 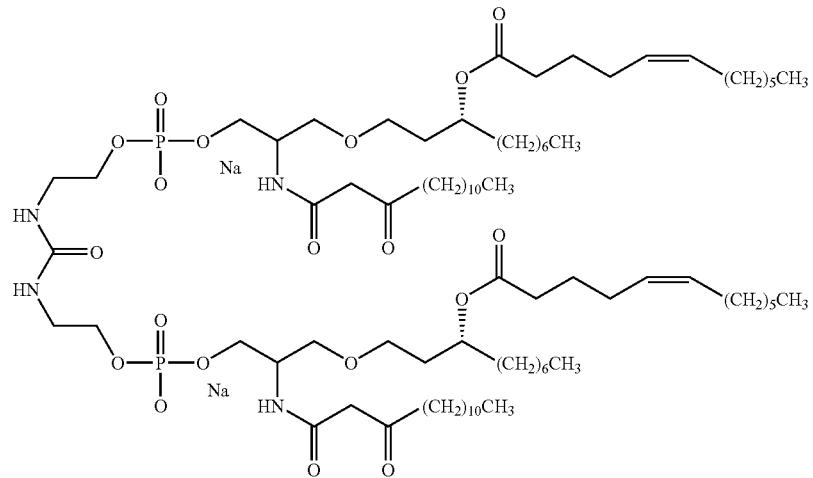 |
| 111233 | 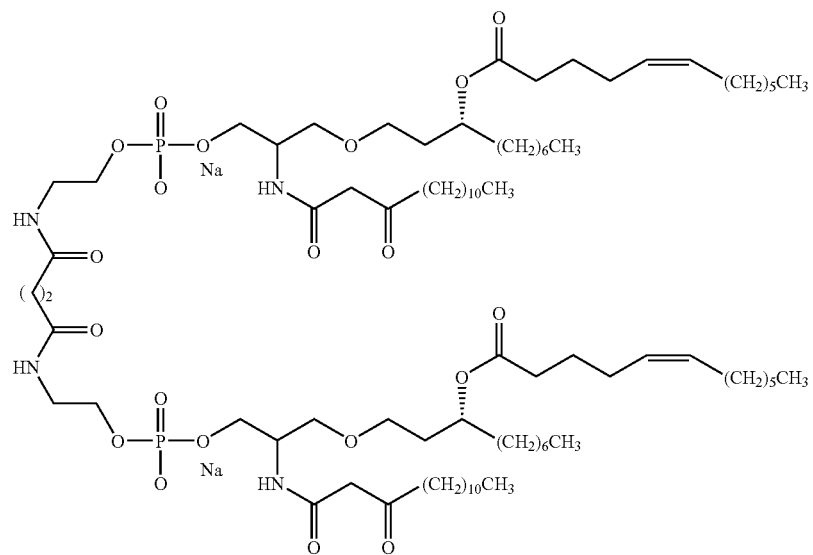 |
| 112043 | 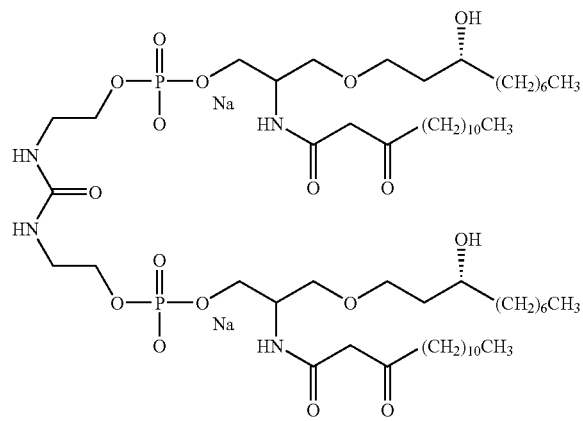 |

| No. | Structure |
|---|---|
| 112044 | 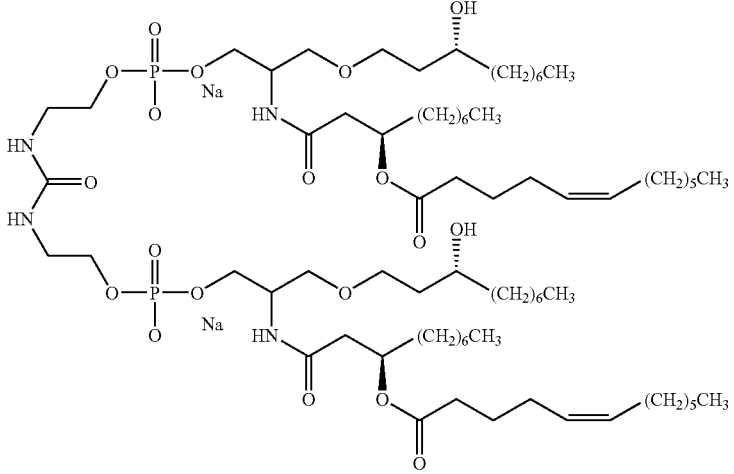 |
| 112047 | 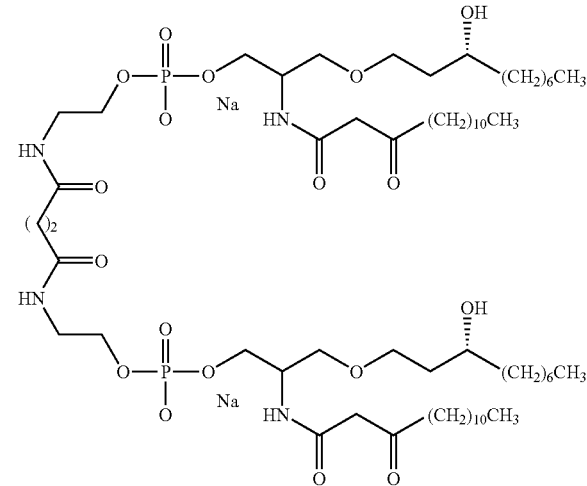 |
| 112048 | 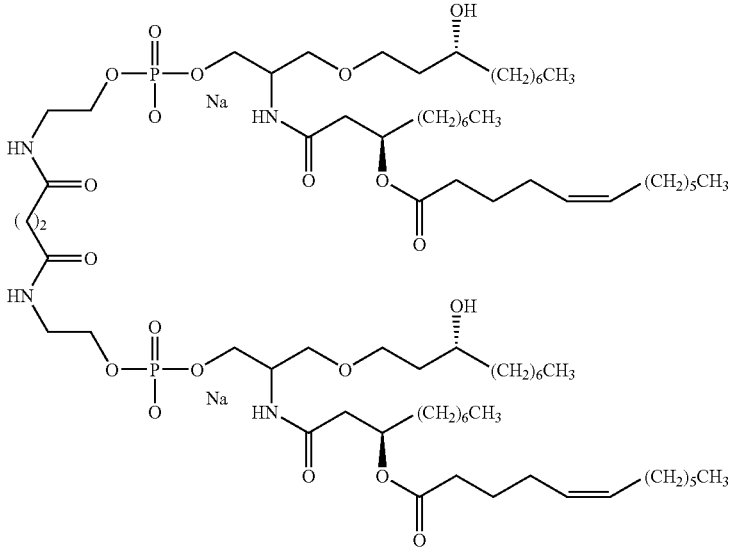 |

-continued
| No. | Structure |
|---|---|
| 112049 | 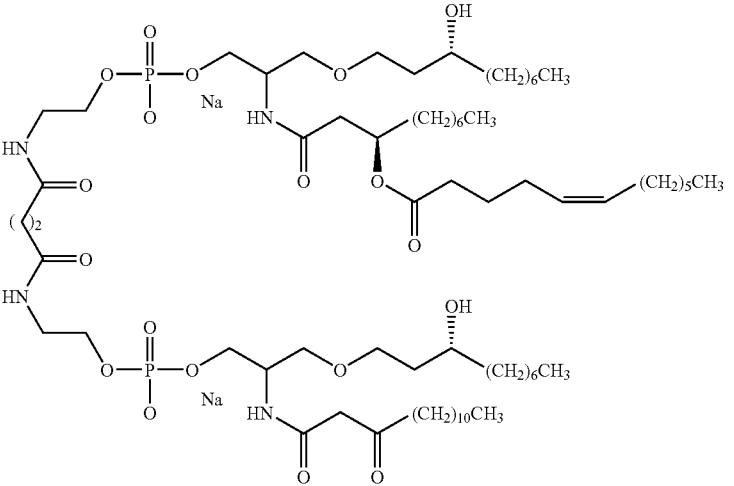 |
| 112063 | 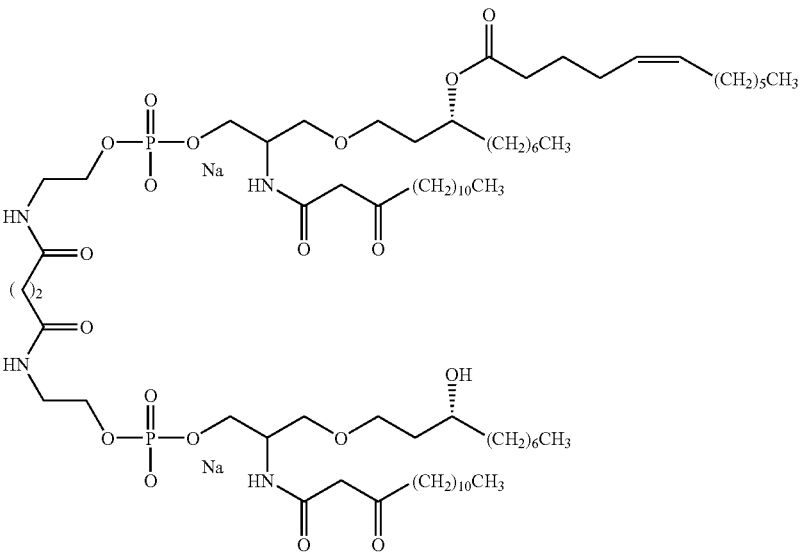 |
| 112064 | 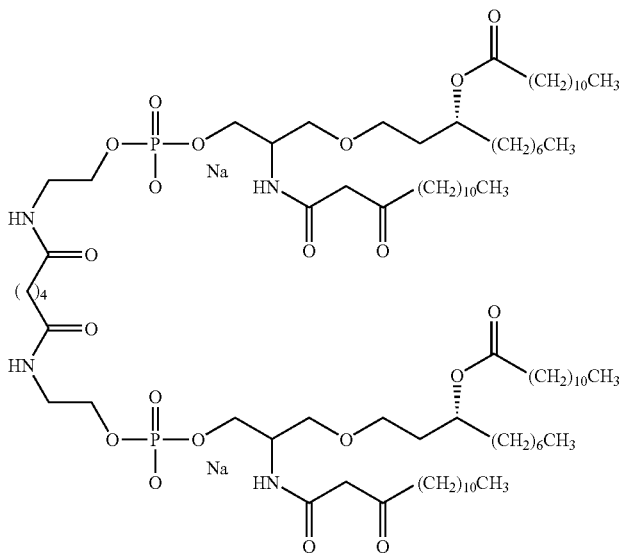 |

| No. | Structure |
|---|---|
| 112065 | 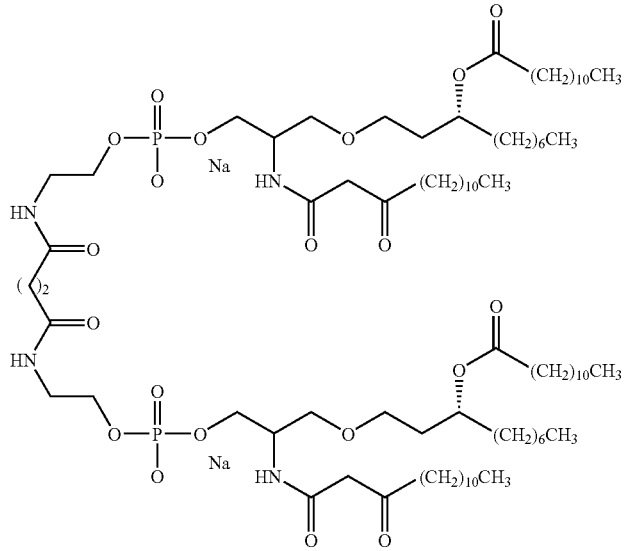 |
| 112066 | 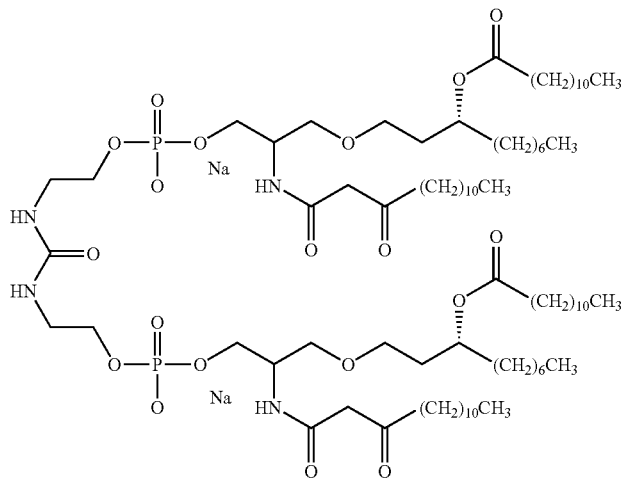 |
| 112071 | 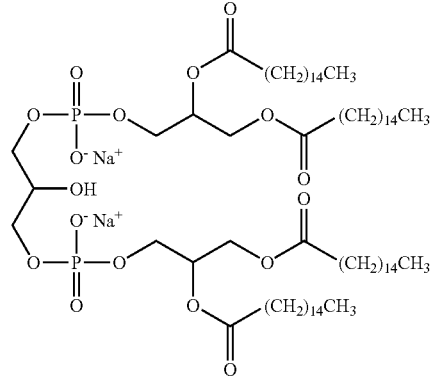 |

-continued

| No. | Structure |
|---|---|
| 112072 | 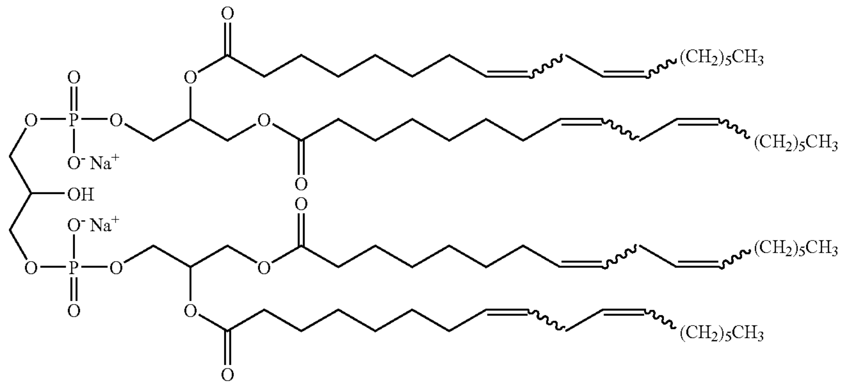 |
| 112091 | 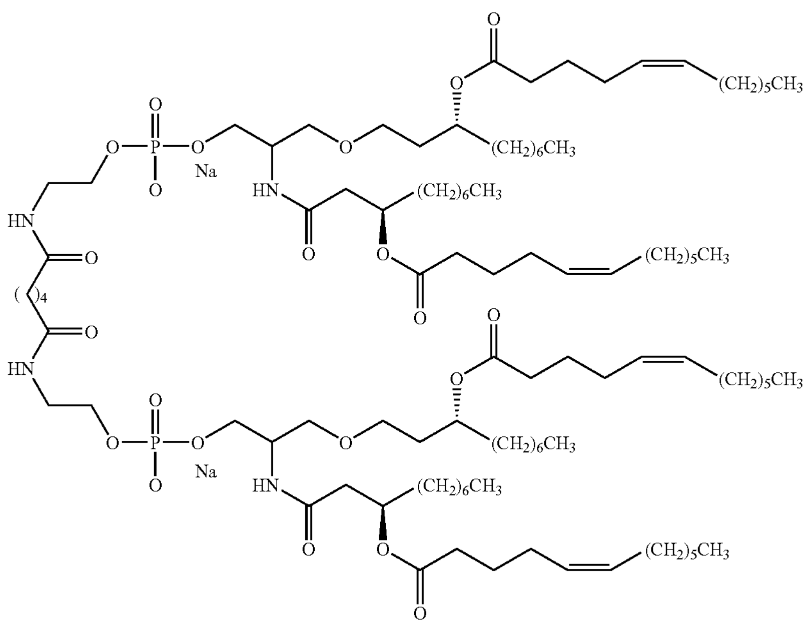 |
| 112092 | 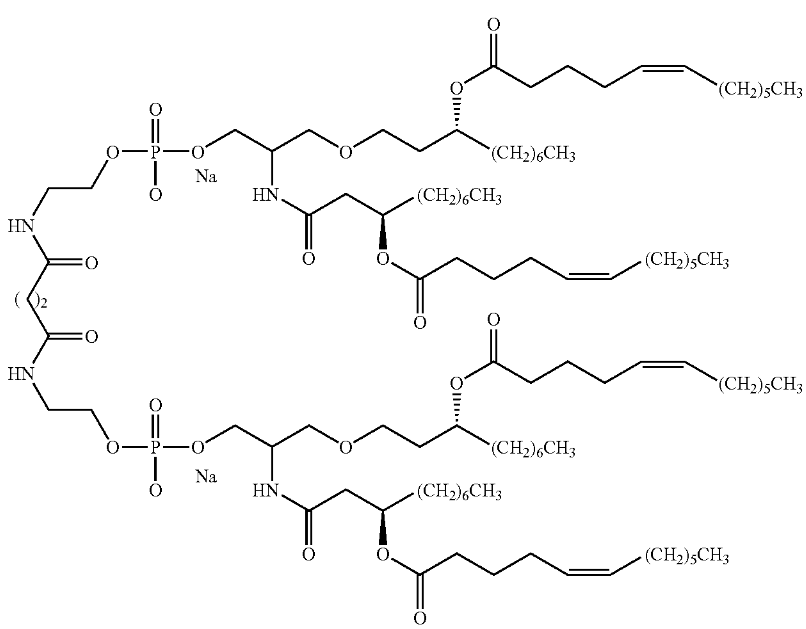 |

| No. | Structure |
|---|---|
| 112093 | 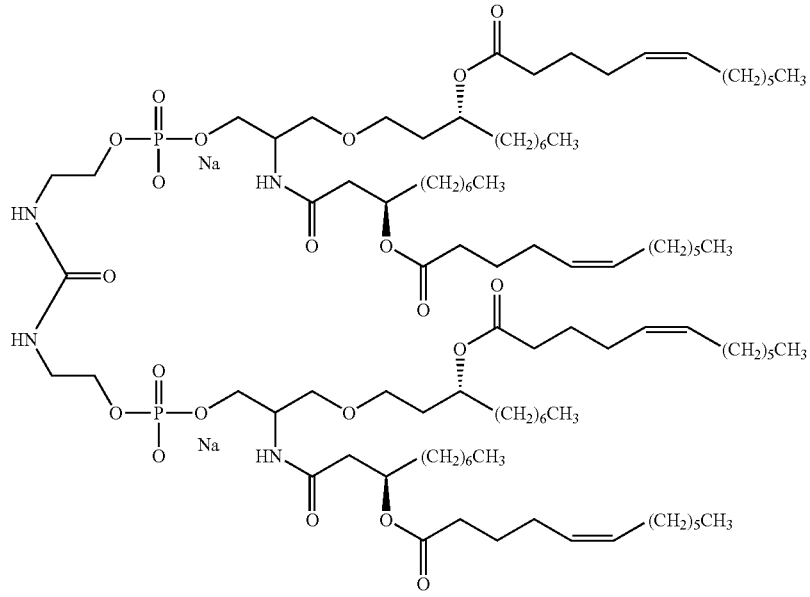 |
| 112098 | 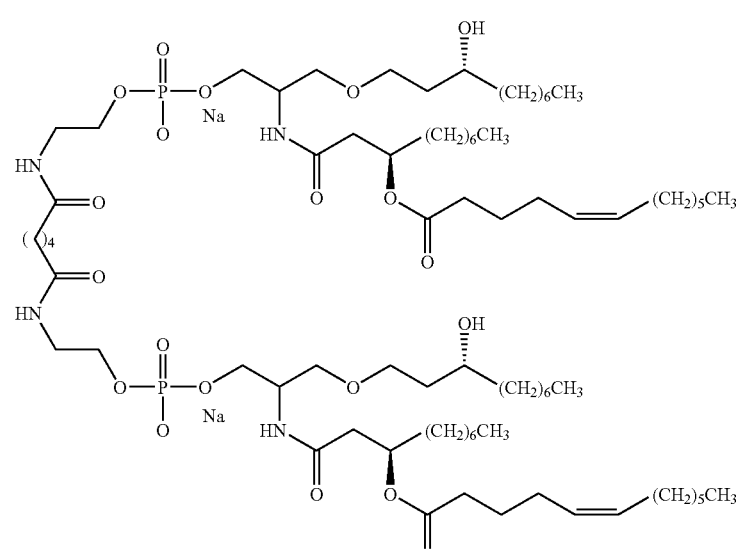 |

| No. | Structure |
|---|---|
| 112099 | 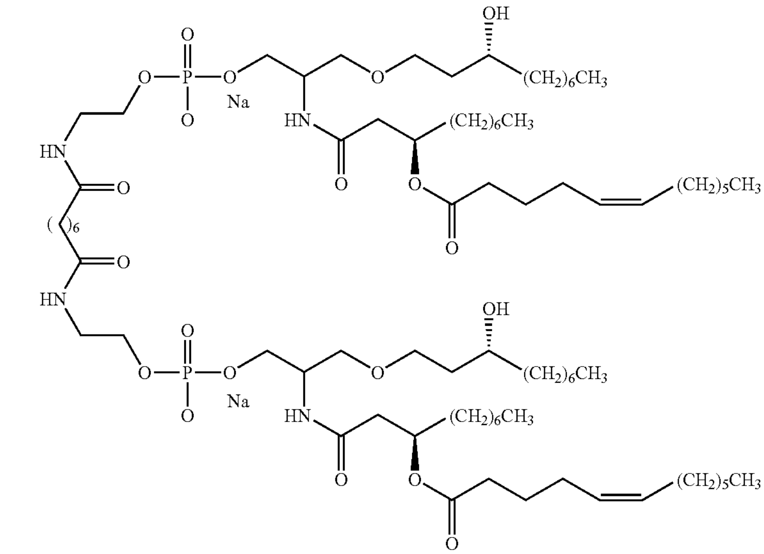 |
| 112100 | 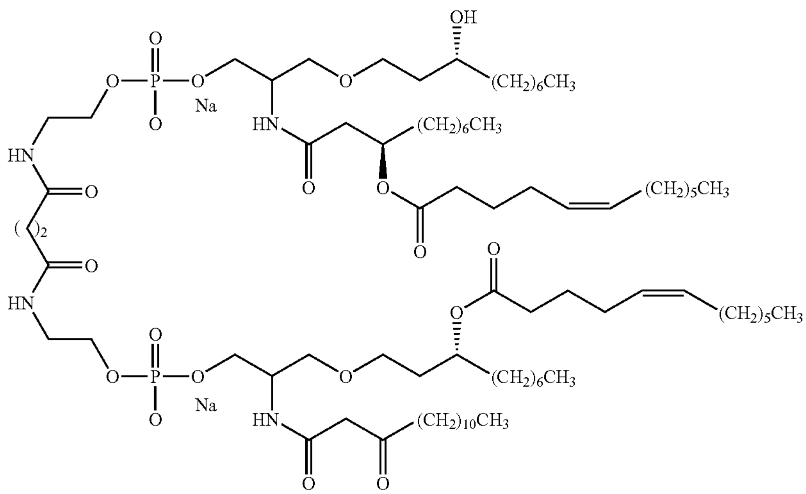 |
| 112859 | 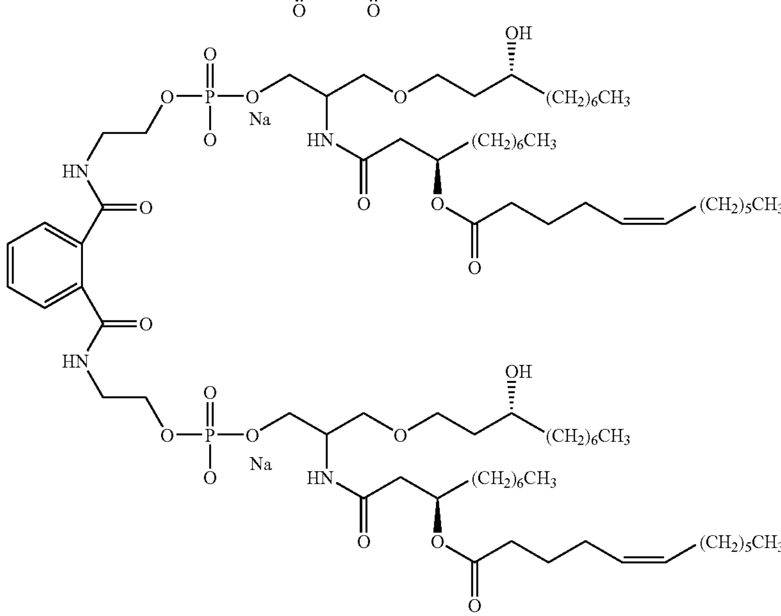 |

-continued
| No. | Structure |
|---|---|
| 112860 | 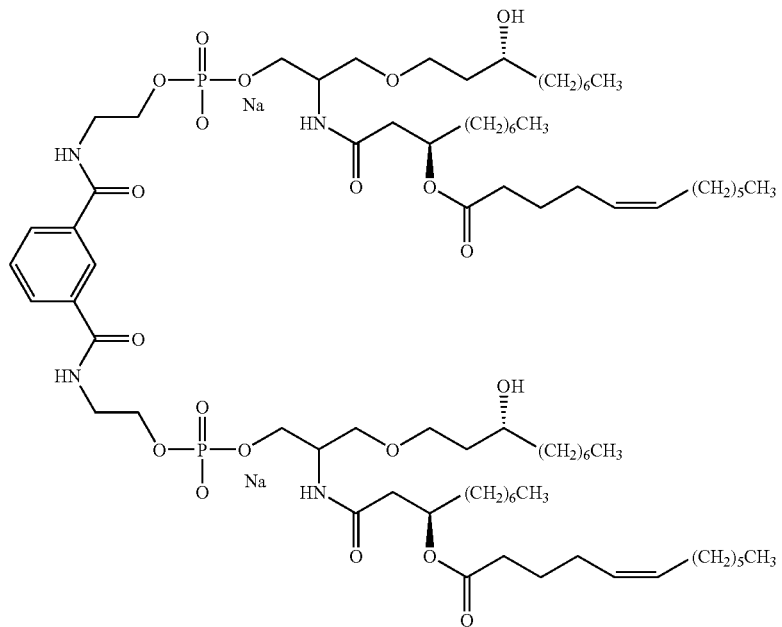 |
| 112861 | 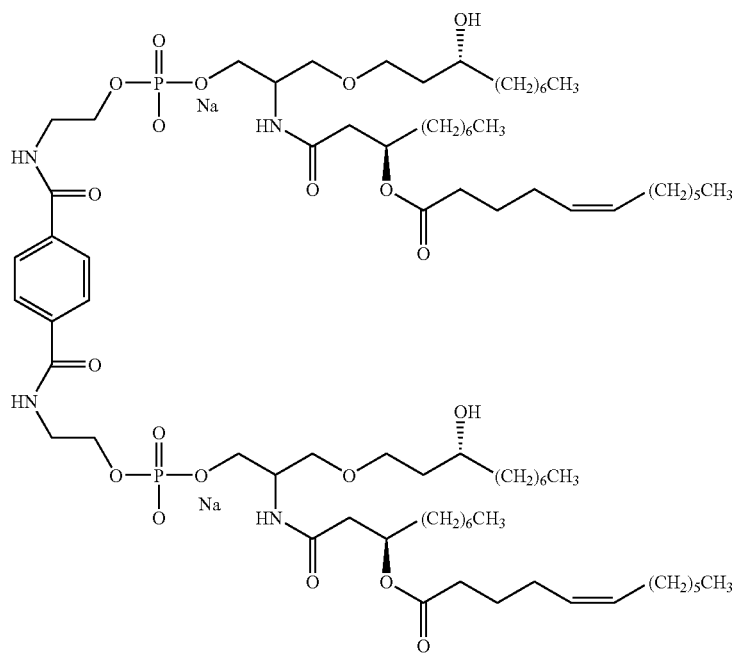 |

| No. | Structure |
|---|---|
| 113634 | 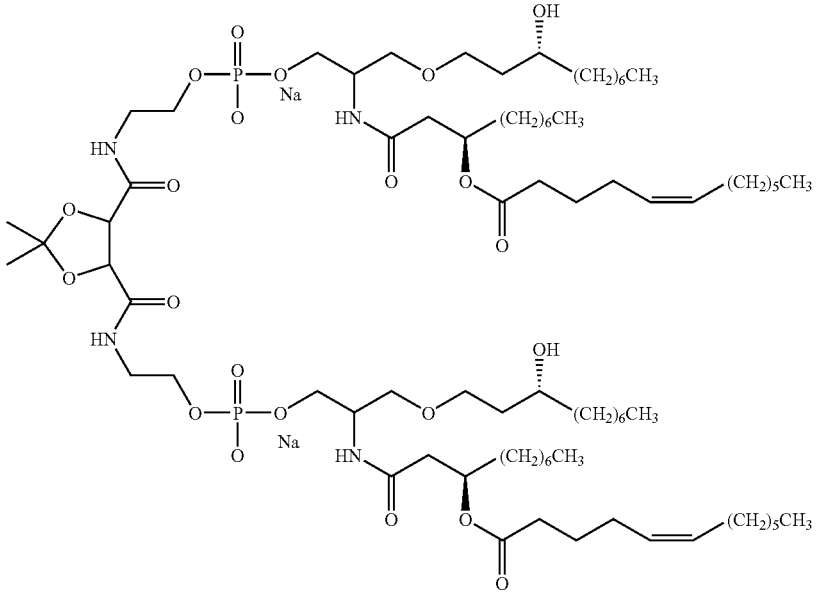 |
| 113635 | 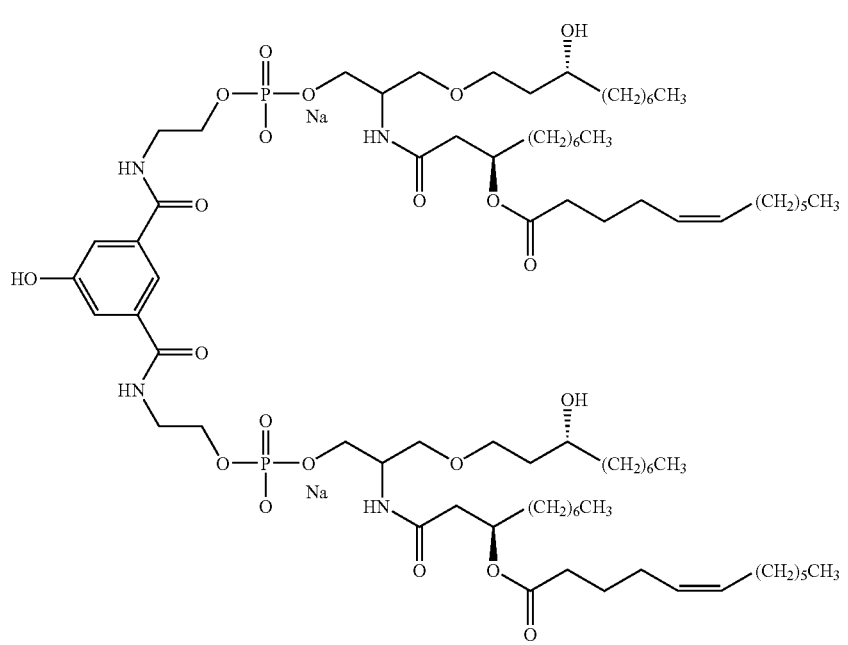 |

| No. | Structure |
| --- | --- |
| 113643 | 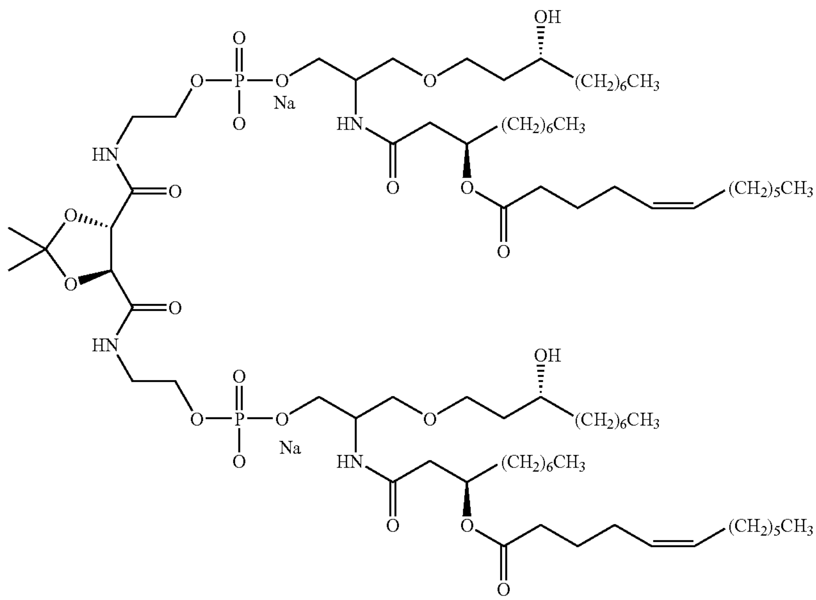 |
| 113644 | 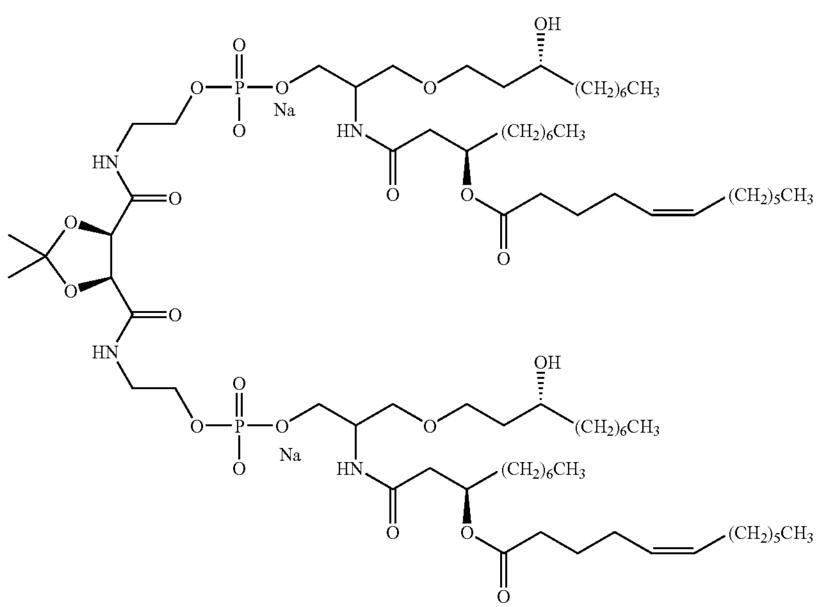 |

| No. | Structure |
|---|---|
| 113651 | 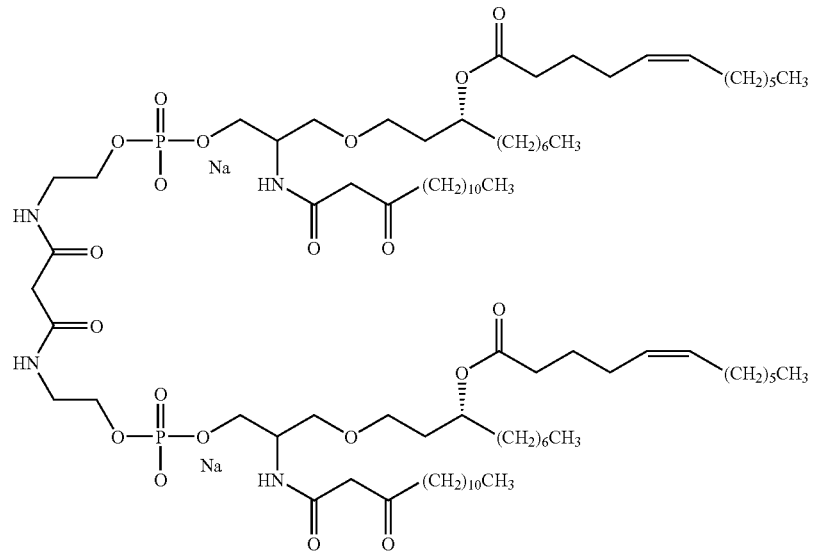 |
| 113665 | 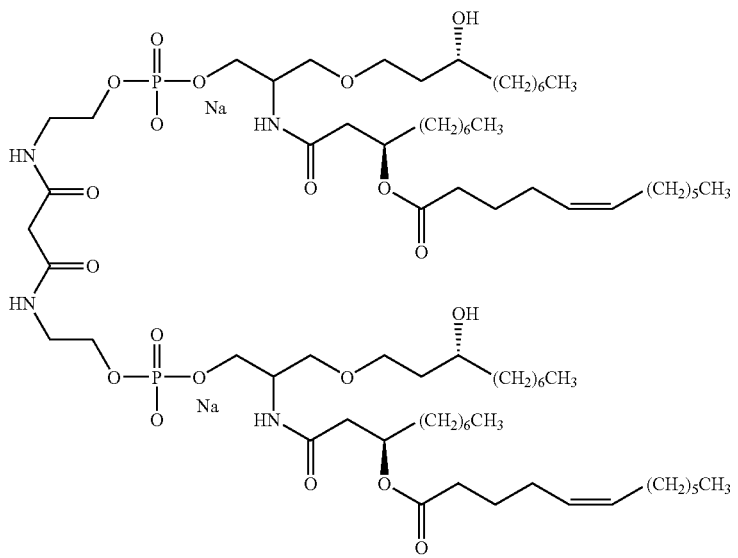 |

| No. | Structure |
|---|---|
| 113666 | 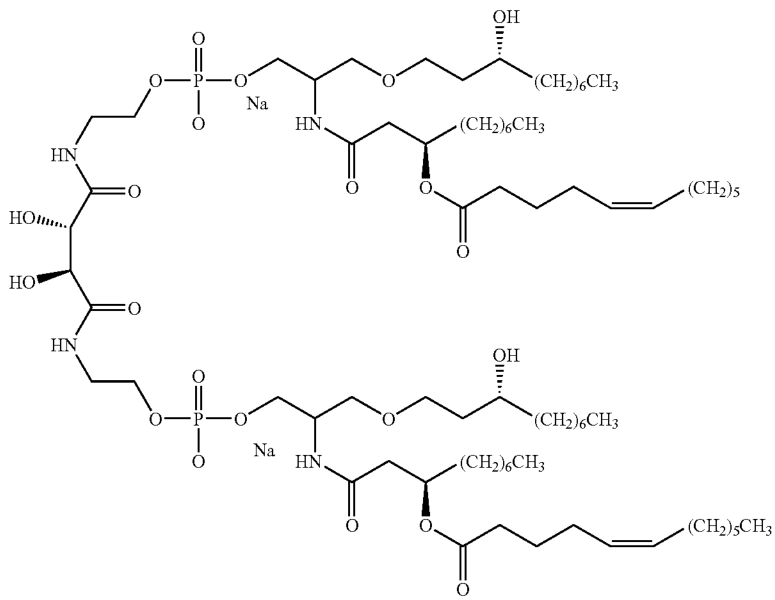 |
| 118023 | 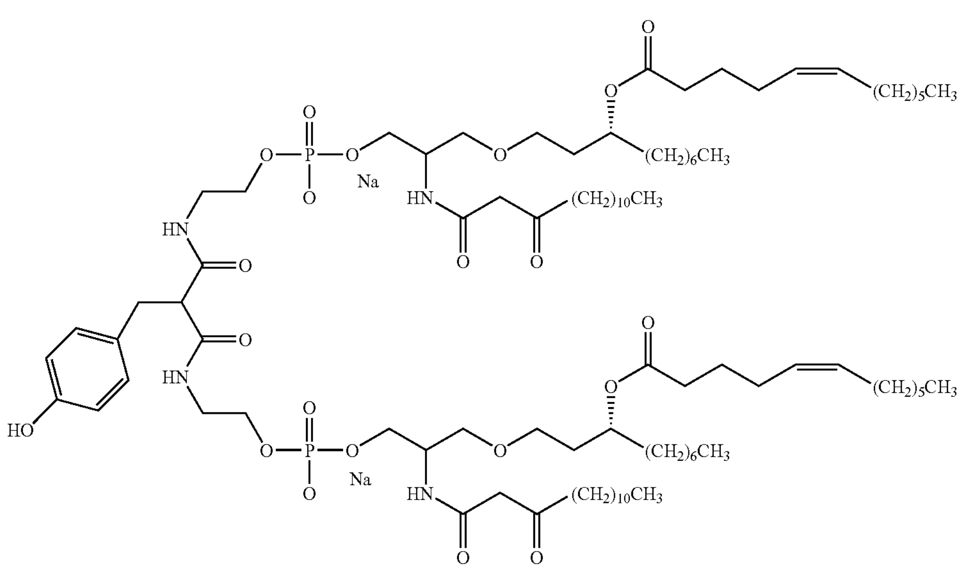 |

| No. | Structure |
|---|---|
| 019772 | 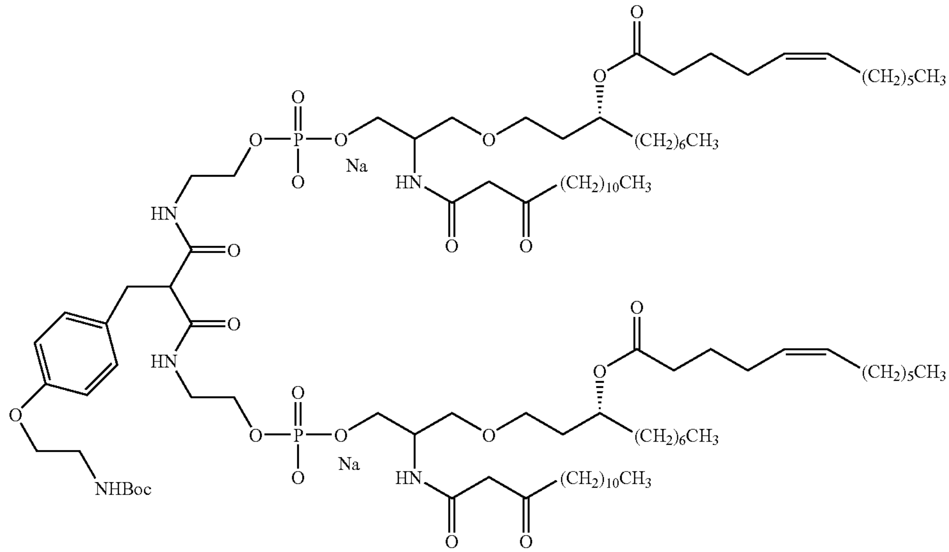 |
| 118989 | 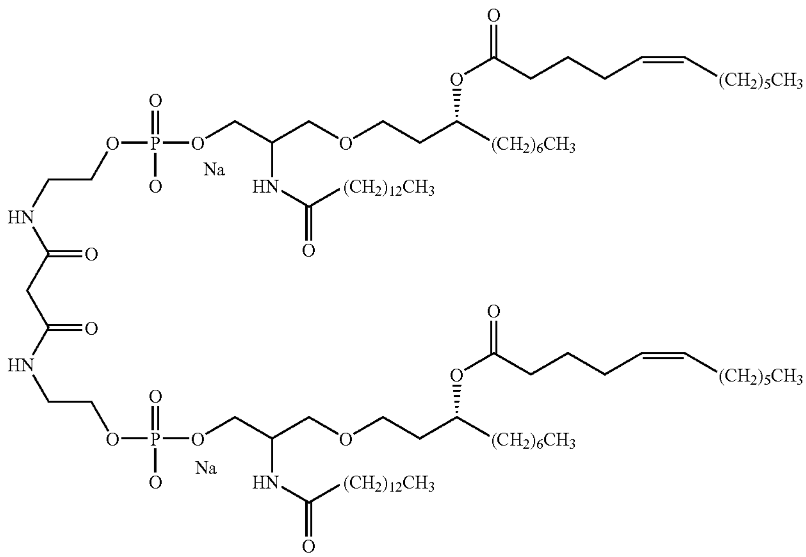 |
| 118999 | 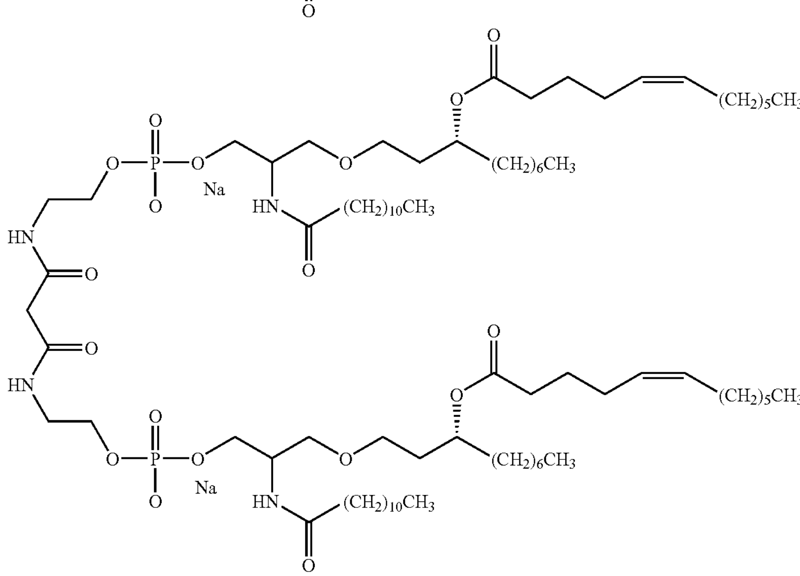 |

| No. | Structure |
|---|---|
| 119000 | 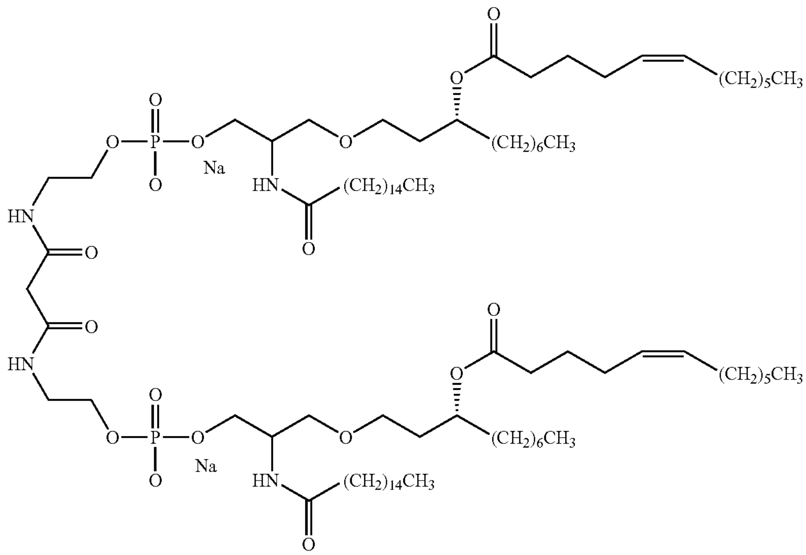 |
| 119001 | 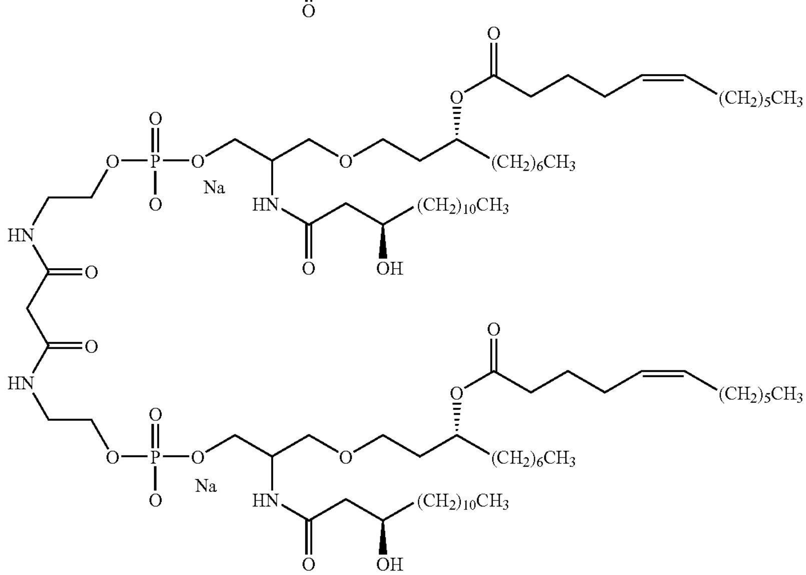 |
| 118949 | 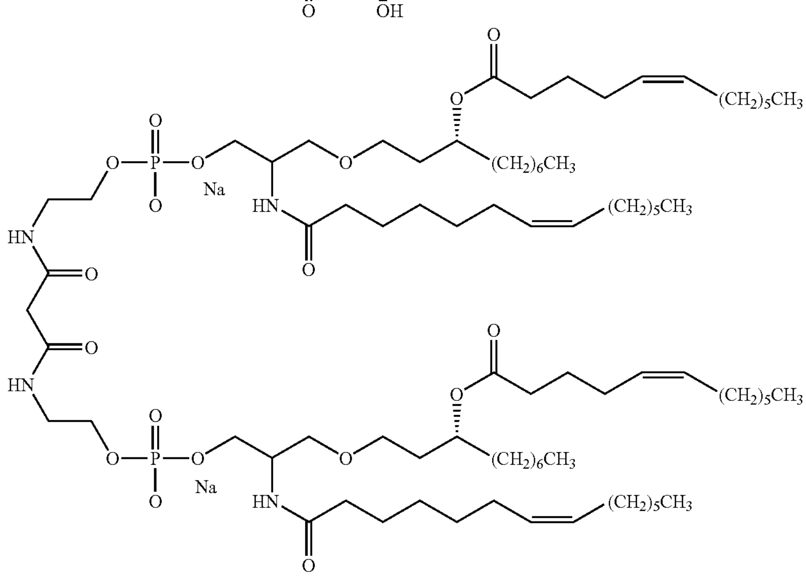 |

| No. | Structure |
|---|---|
| 119327 | 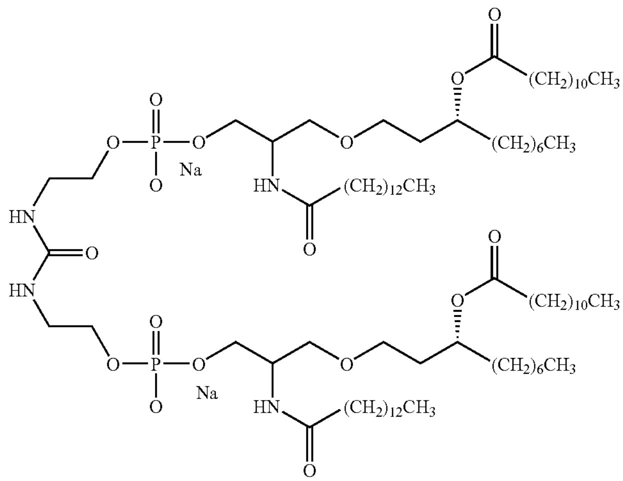 |
| 119328 | 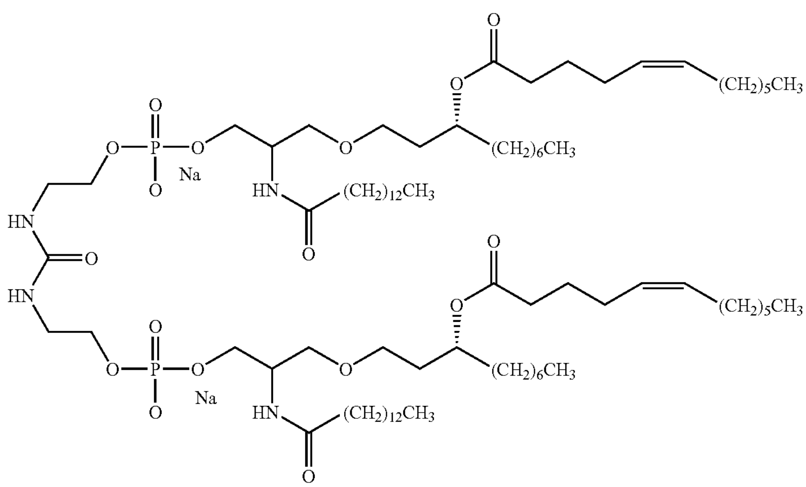 |
| 119329 | 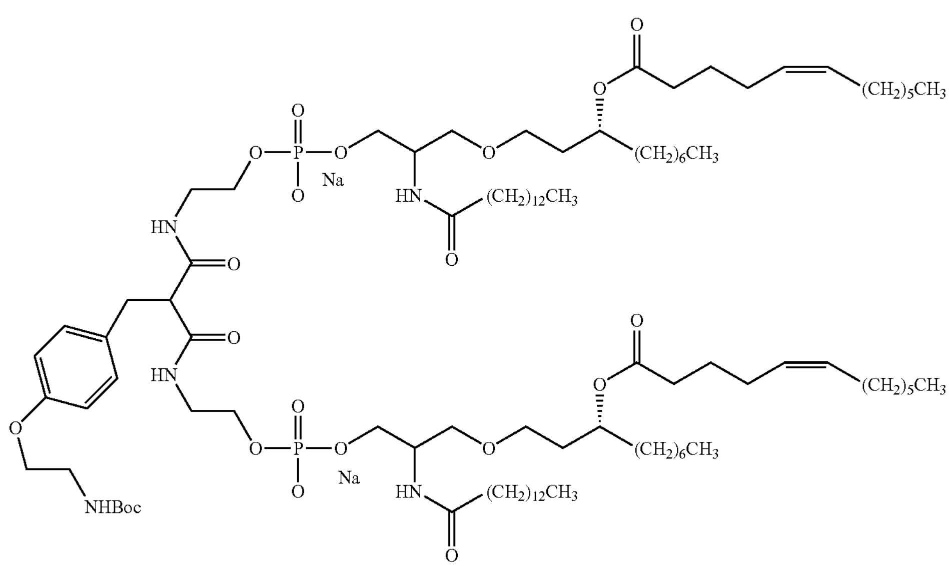 |

| No. | Structure |
|---|---|
| 119521 | 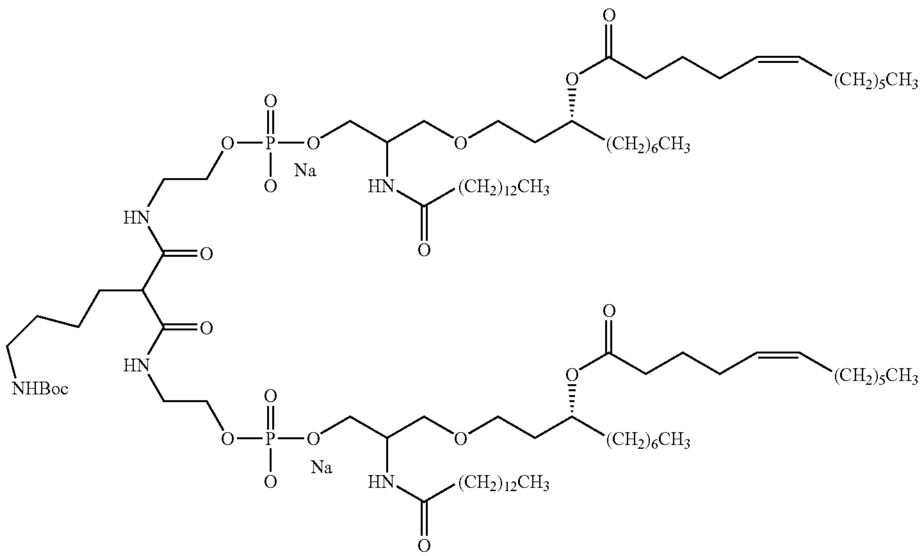 |
| 119522 | 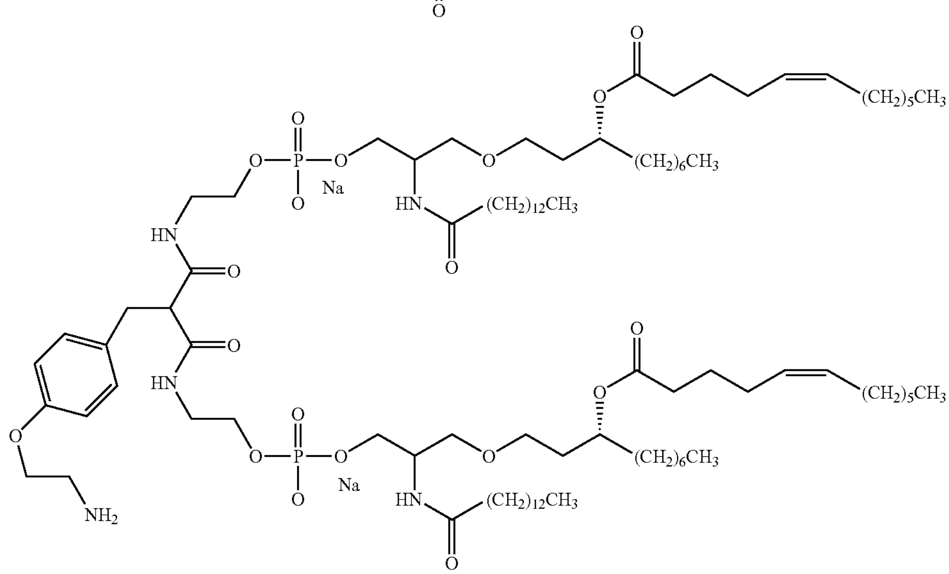 |
| 119523 | 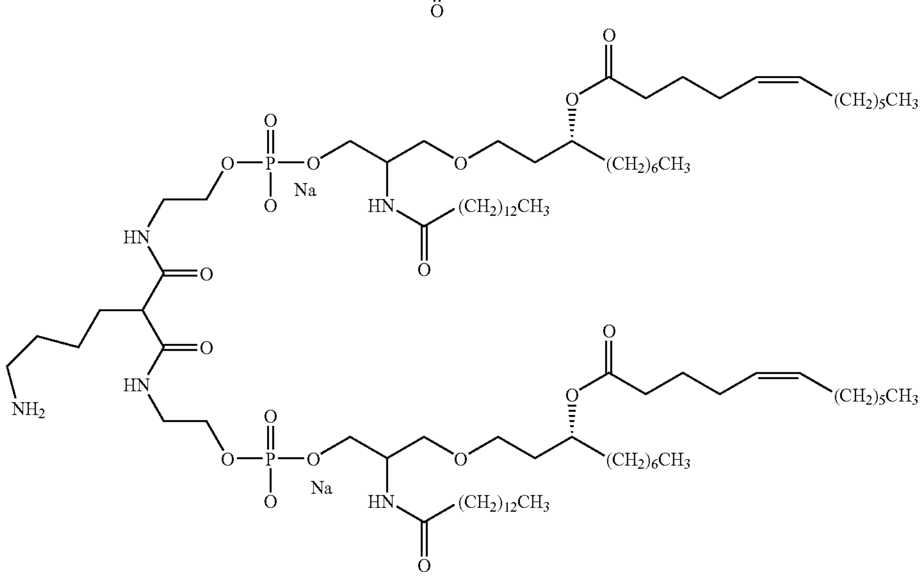 |

-continued
| No. | Structure |
|---|---|
| 803028 | 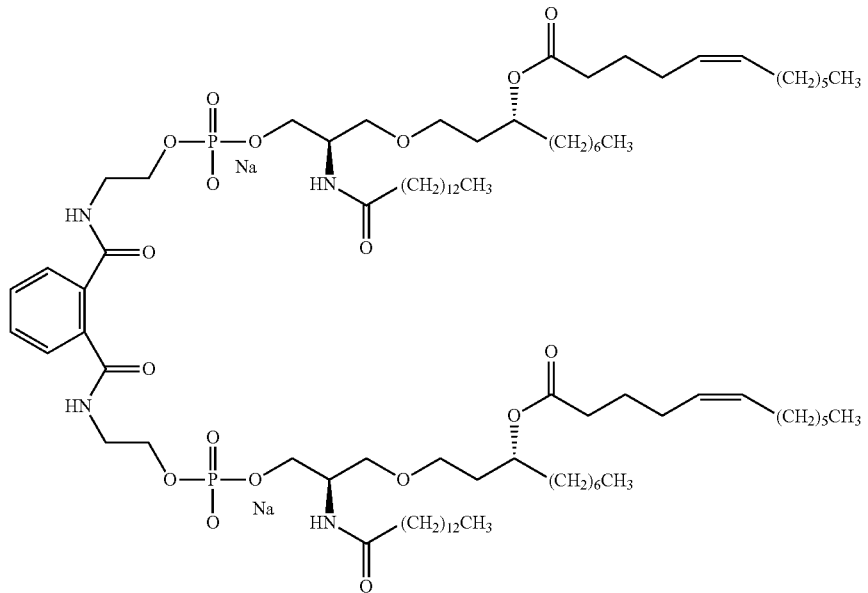 |
| 803045 | 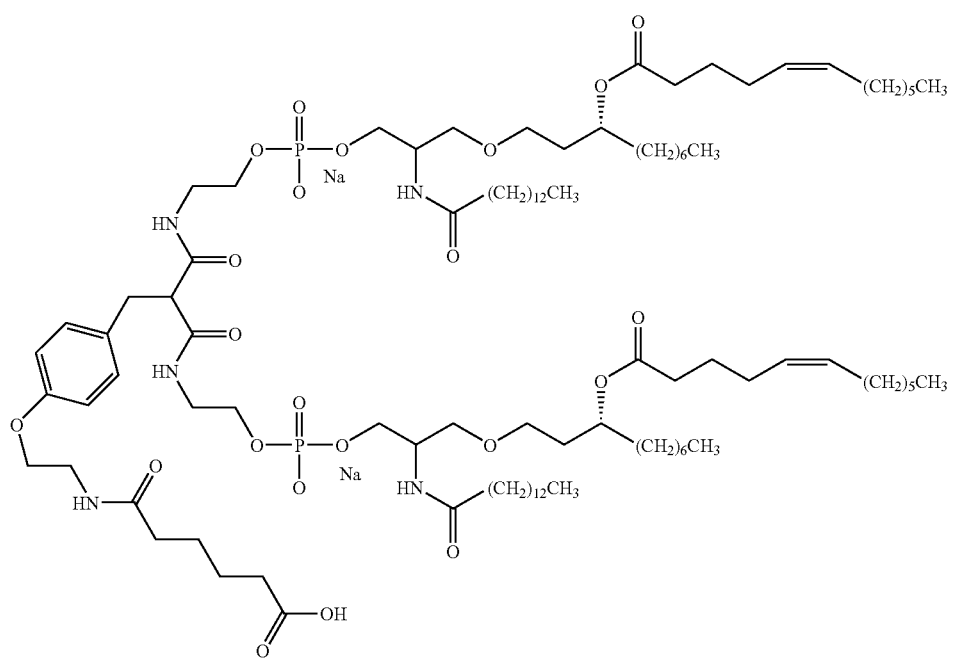 |

| No. | Structure |
|---|---|
| 803056 | 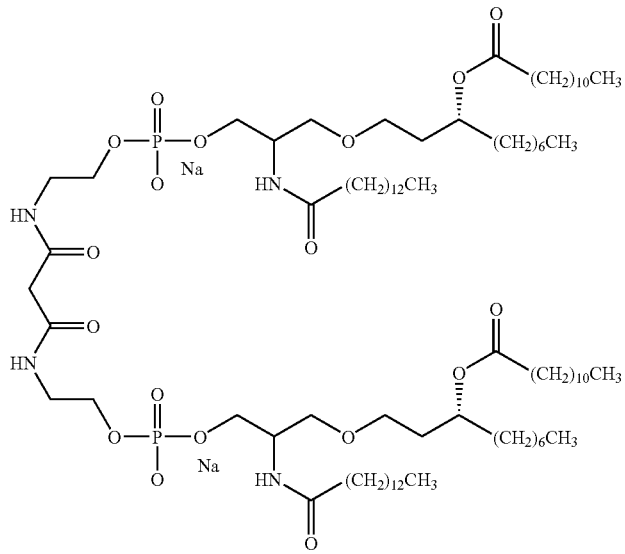 |
| 803059 | 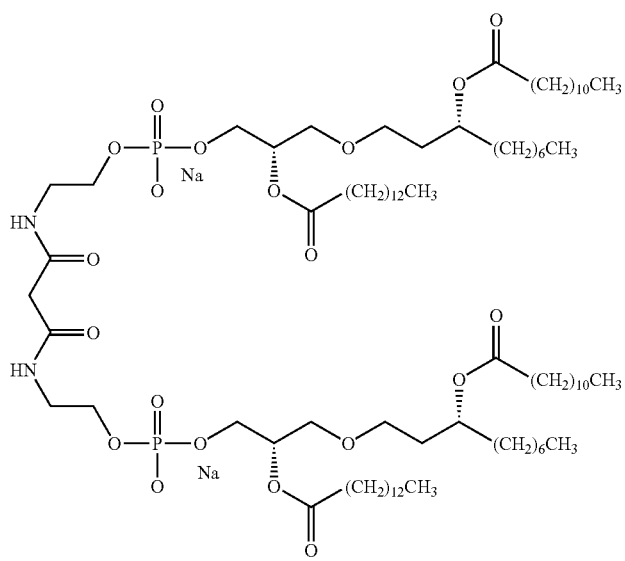 |
| 803592 | 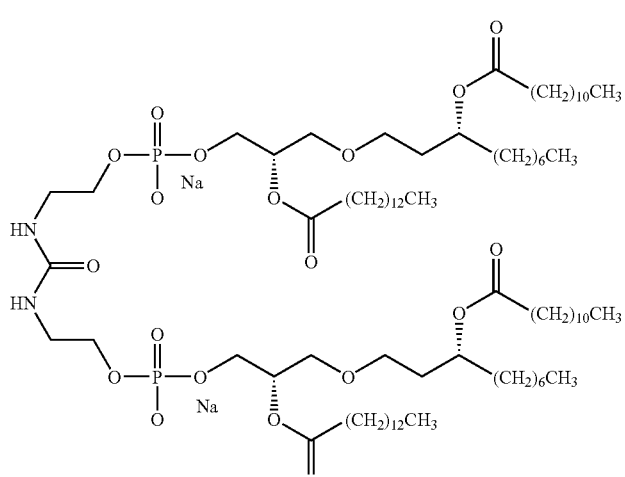 |

| No. | Structure |
|---|---|
| 803596 | 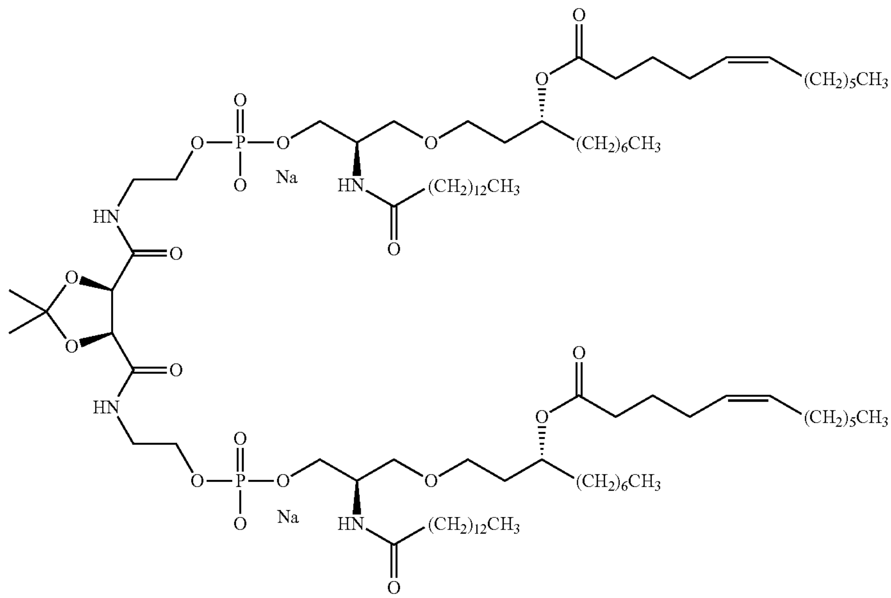 |
| 803597 | 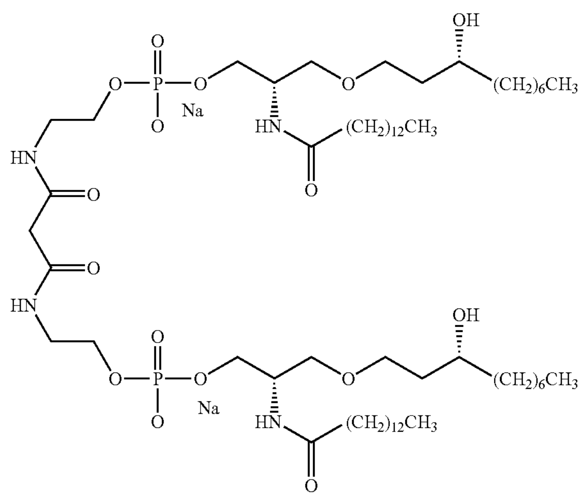 |
| 803598 | 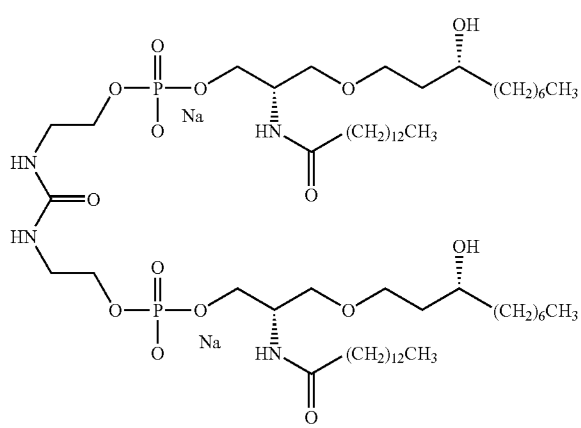 |

| No. | Structure |
|---|---|
| 803599 | 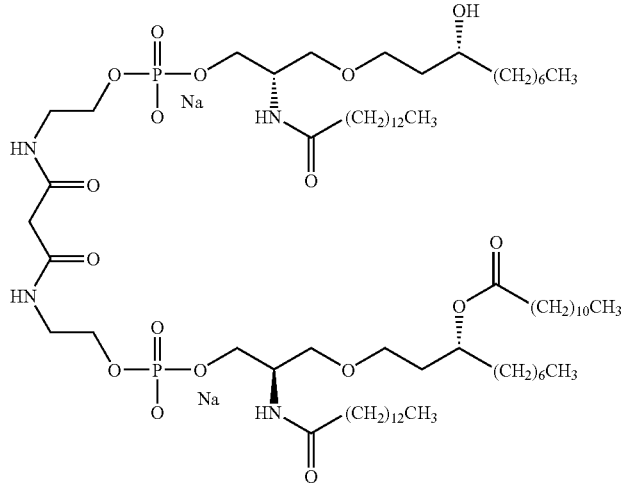 |
| 803613 | 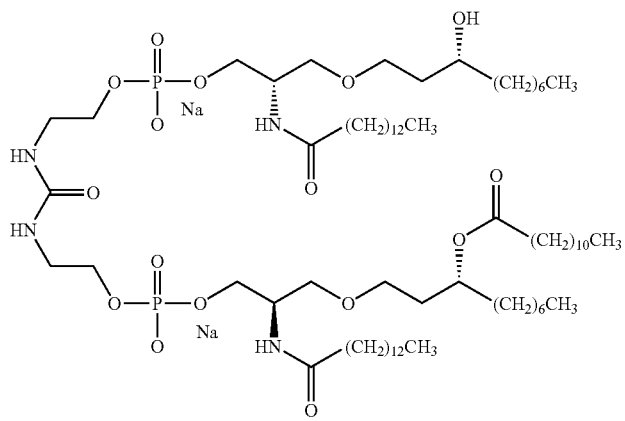 |
| 803731 | 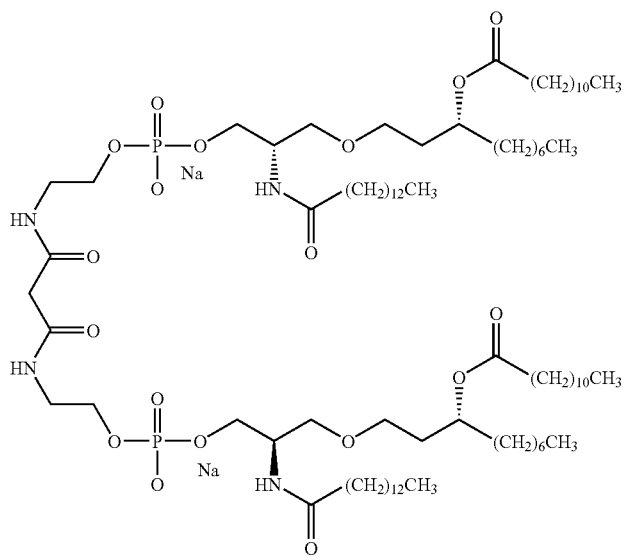 |

| No. | Structure |
|---|---|
| 803733 | 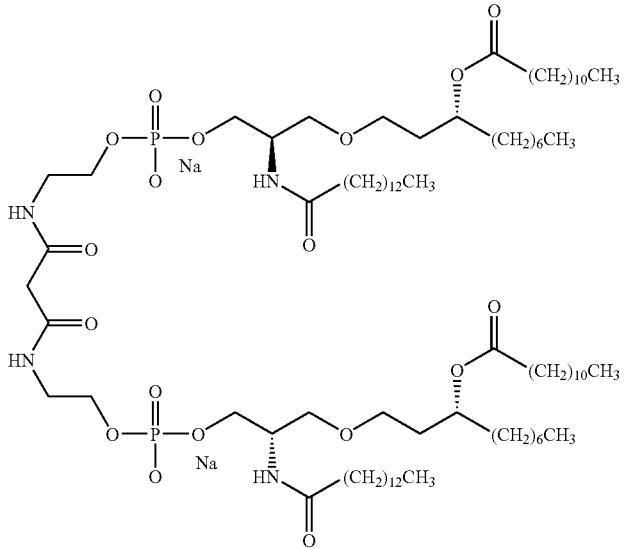 |
| 803751 | 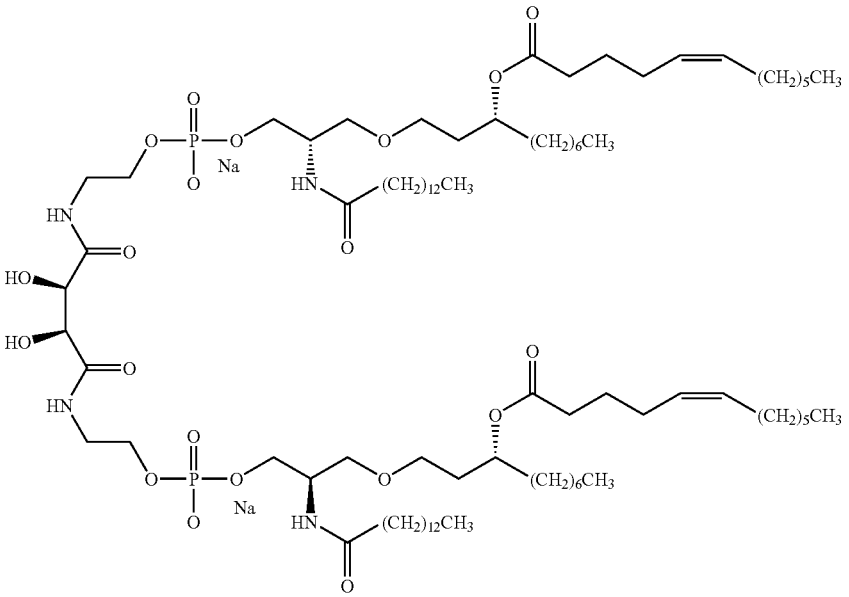 |
| 803783 | 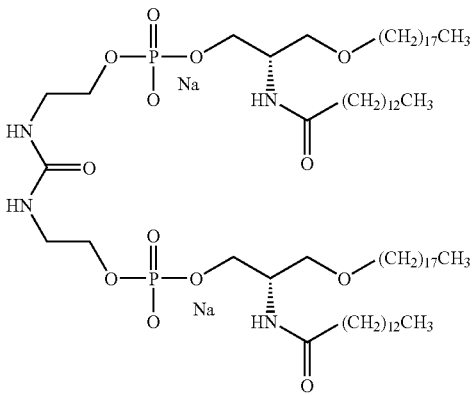 |

-continued

| No. | Structure |
|---|---|
| 803784 | 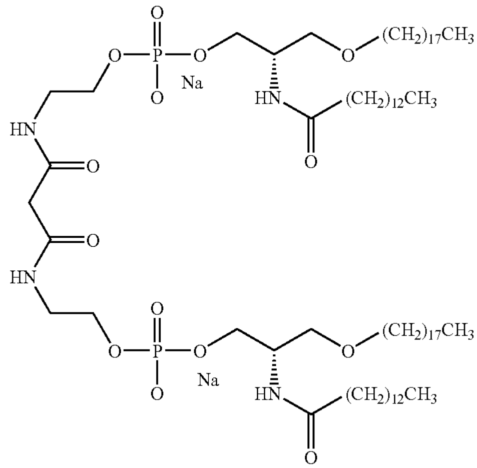 |
| 803789 | 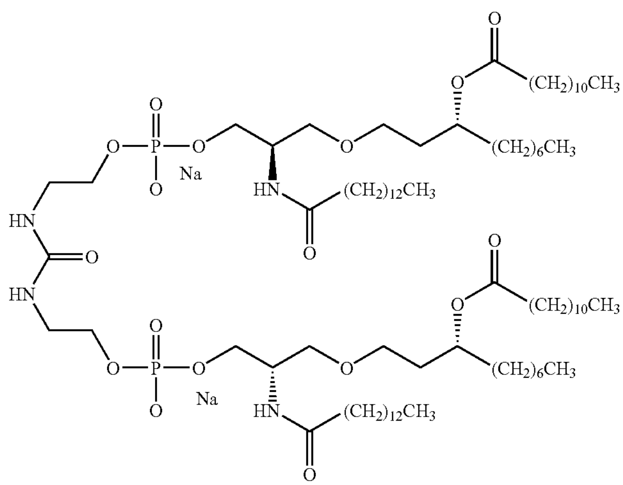 |
| 804061 | 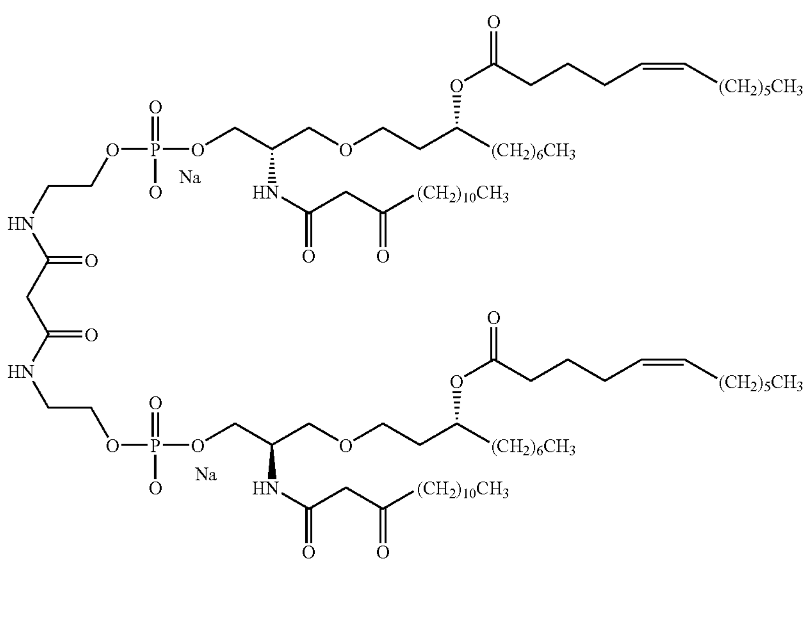 |

| No. | Structure |
|---|---|
| 804097 | 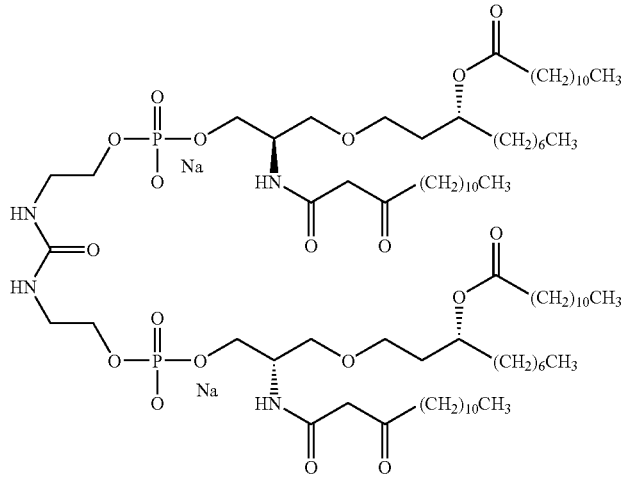 |
| 804121 | 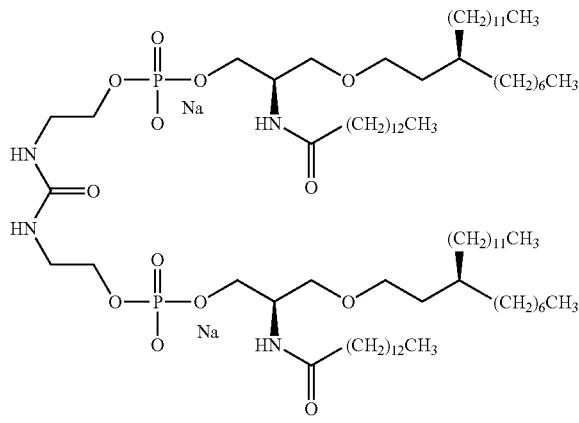 |
| 804130 | 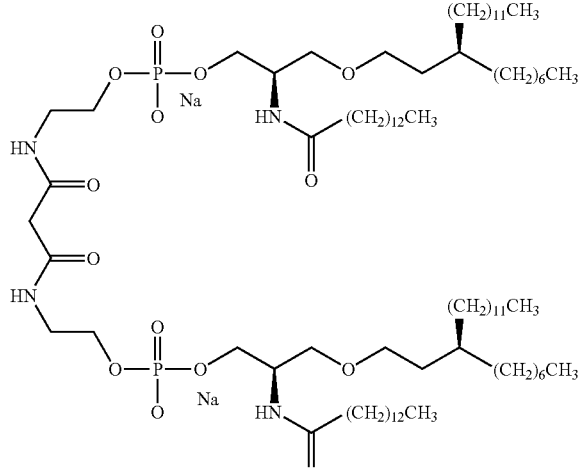 |

| No. | Structure |
|---|---|
| 804221 | 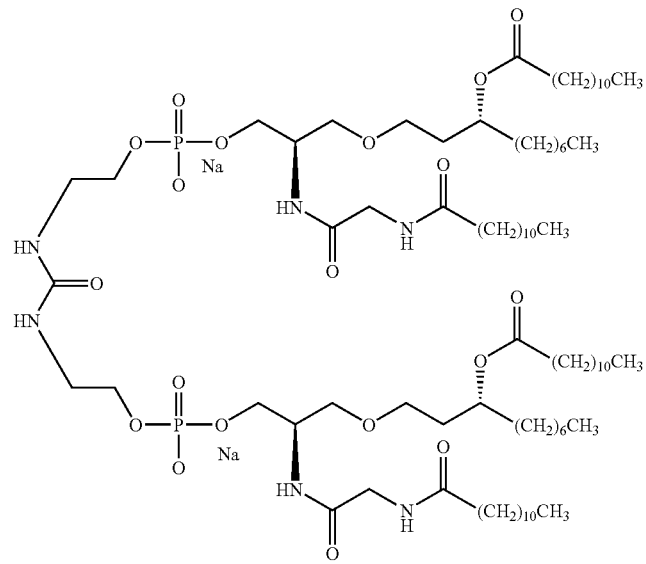 |
| 804222 | 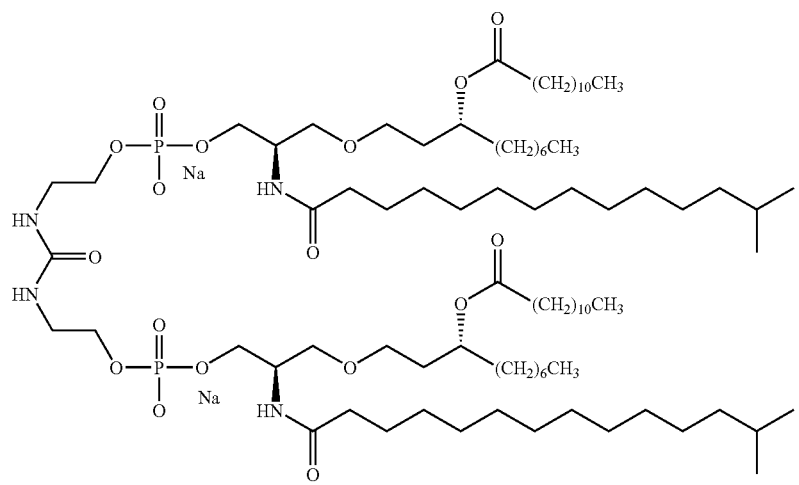 |
| 804252 | 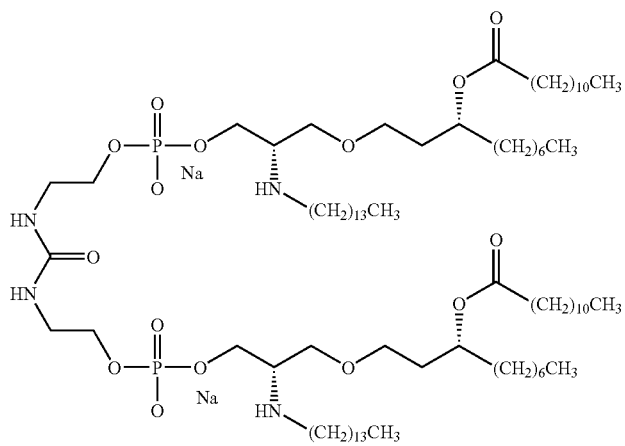 |

| No. | Structure |
|---|---|
| 804253 | 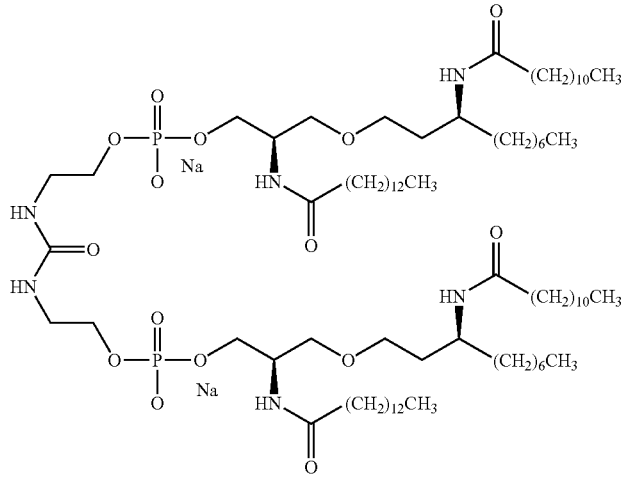 |
| 804281 | 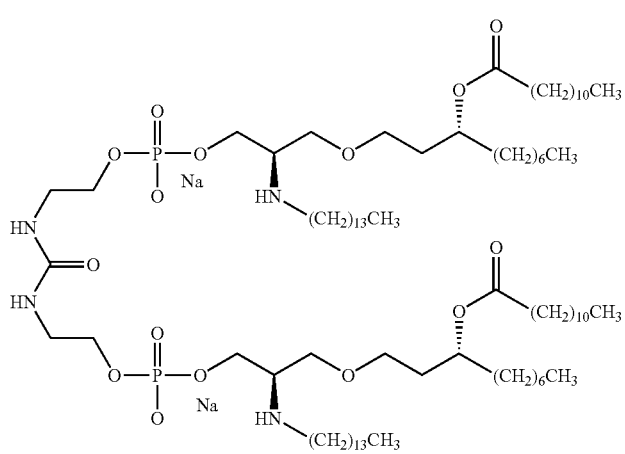 |
| 804313 | 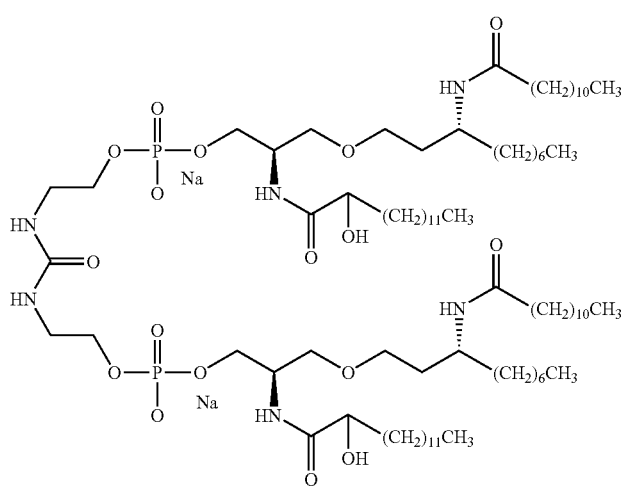 |

| No. | Structure |
|---|---|
| 804339 | 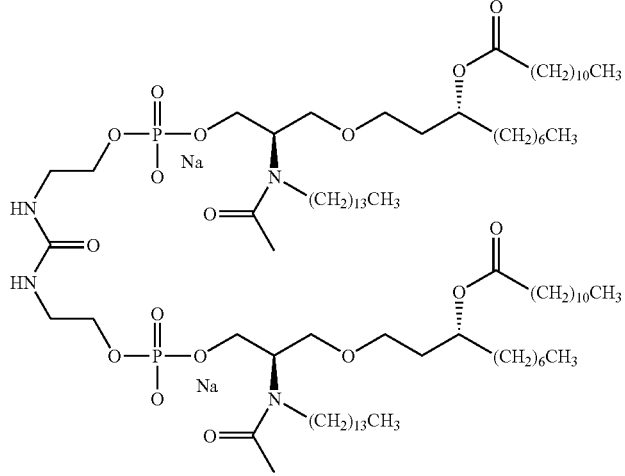 |
| 804372 | 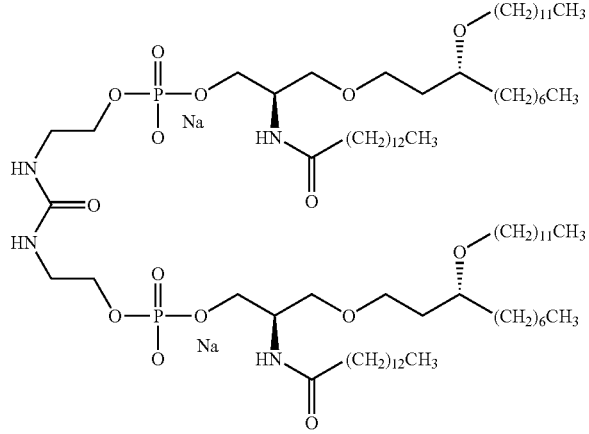 |
| 804503 | 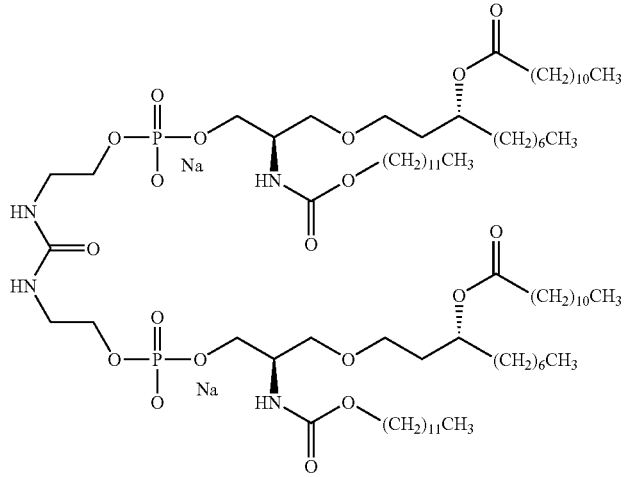 |

| No. | Structure |
|---|---|
| 804558 | 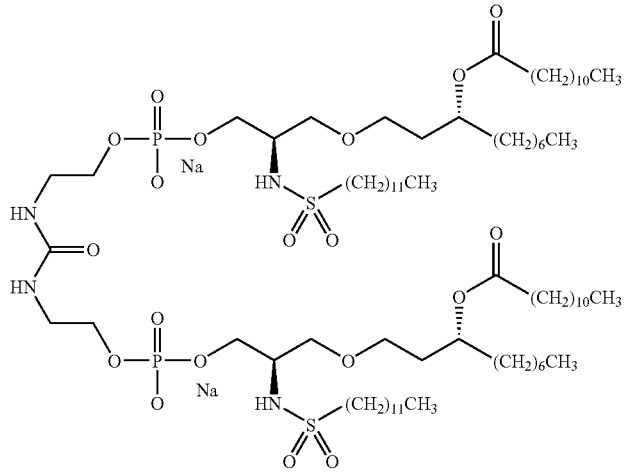 |
| 804596 | 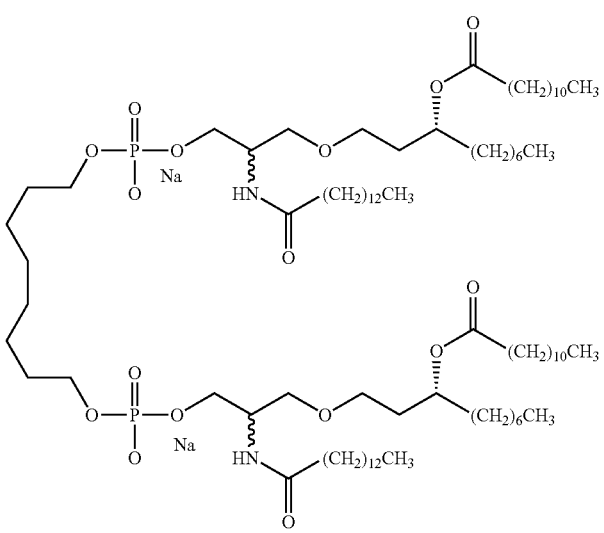 |
| 804674 | 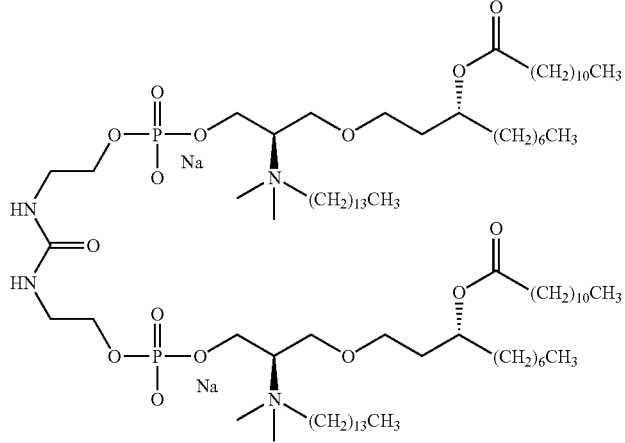 |

| No. | Structure |
|---|---|
| 804678 | 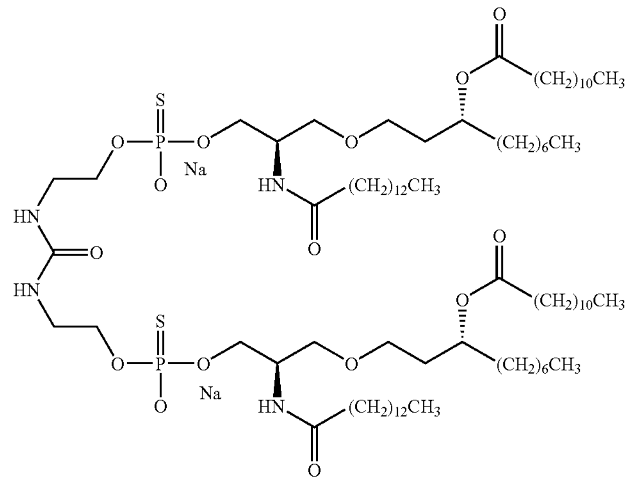 |
| 804679 | 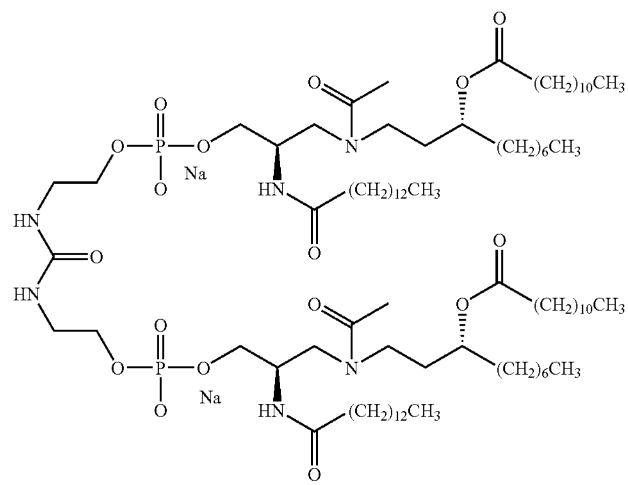 |
| 804732 | 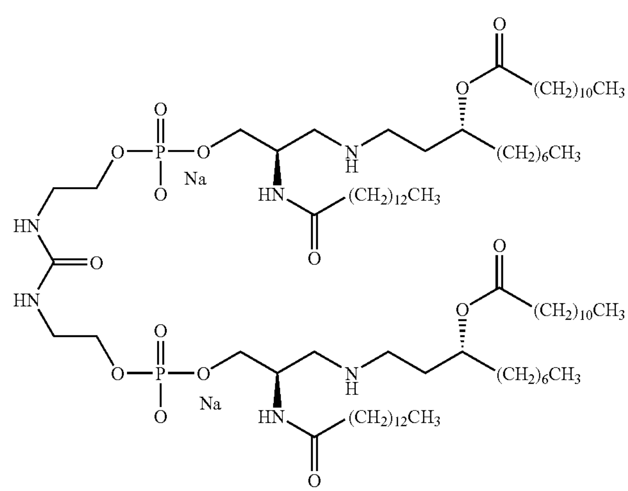 |

| No. | Structure |
|---|---|
| 804772 | 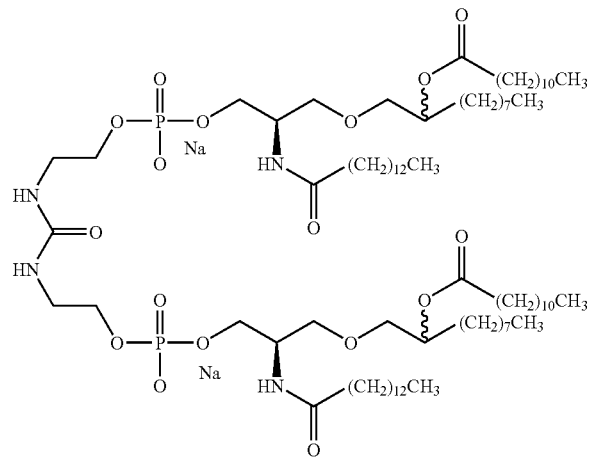 |
| 804947 | 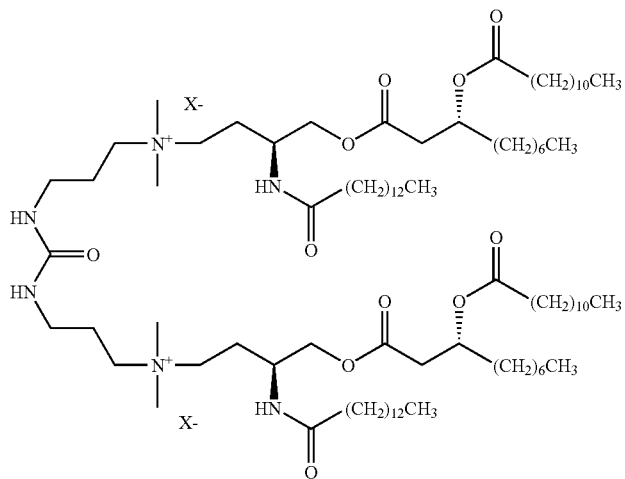 |
| 804638 | 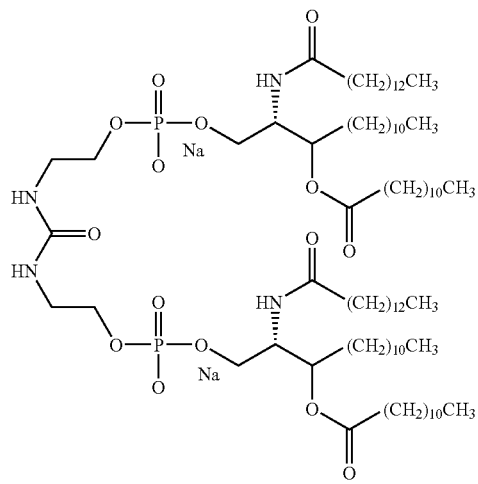 |

| No. | Structure |
|---|---|
| 804666 | 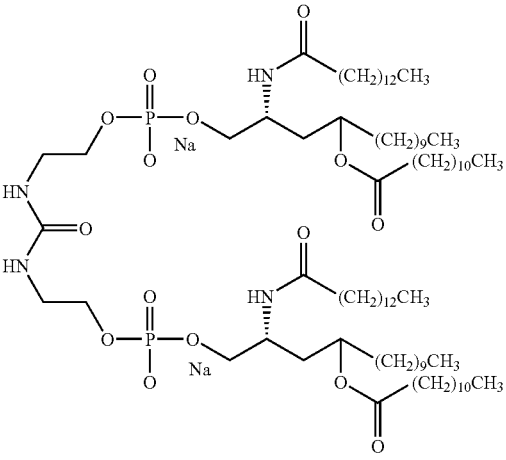 |
| 804874 | 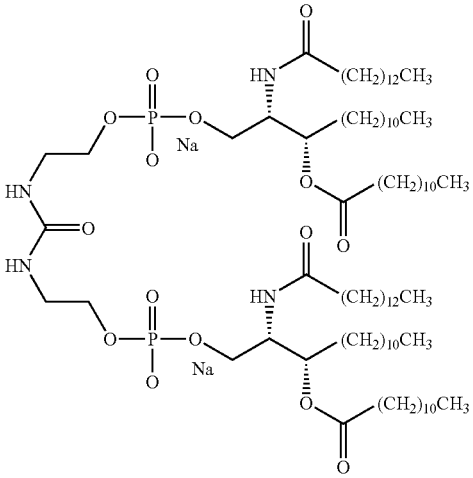 |
| 805028 | 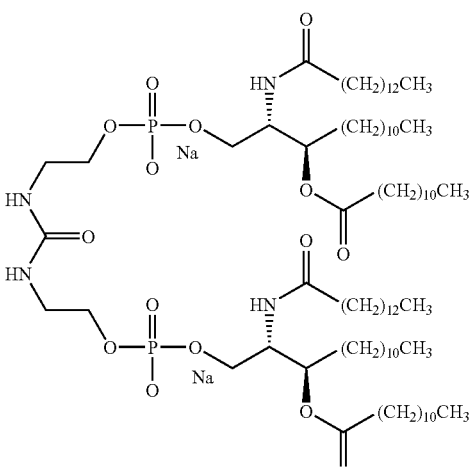 |

| No. | Structure |
|---|---|
| 805520<br>Isomer A | 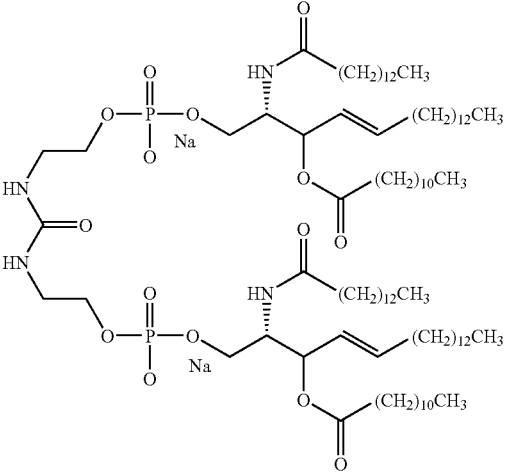 |
| 805270<br>Isomer B | 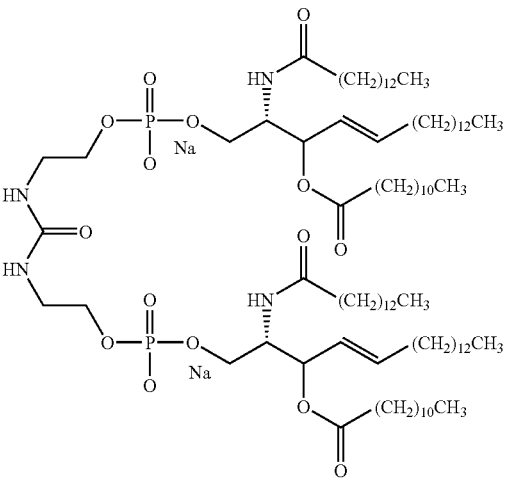 |
| 805271 | 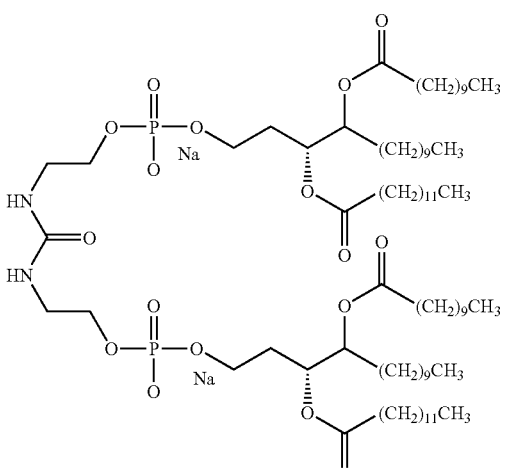 |

| No. | Structure |
|---|---|
| 805274 | 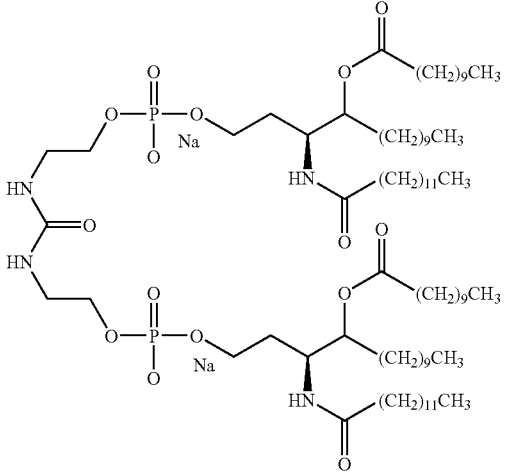 |
| 805328 | 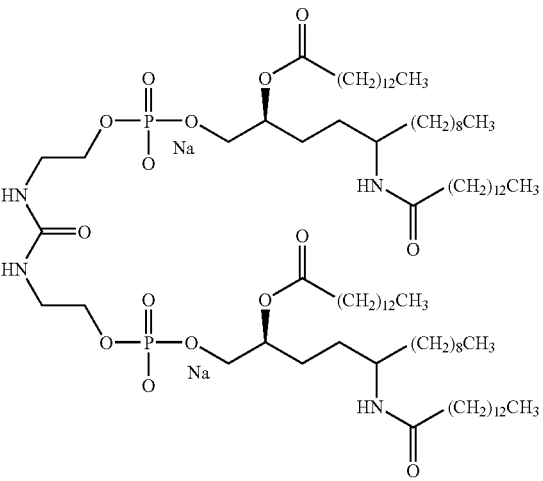 |
| 805329 | 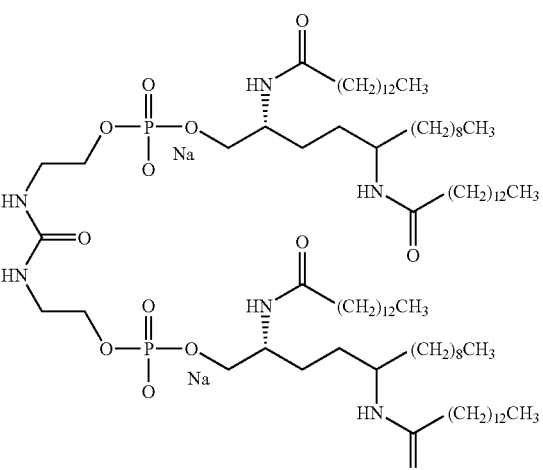 |

| No. | Structure |
|---|---|
| 805517 | 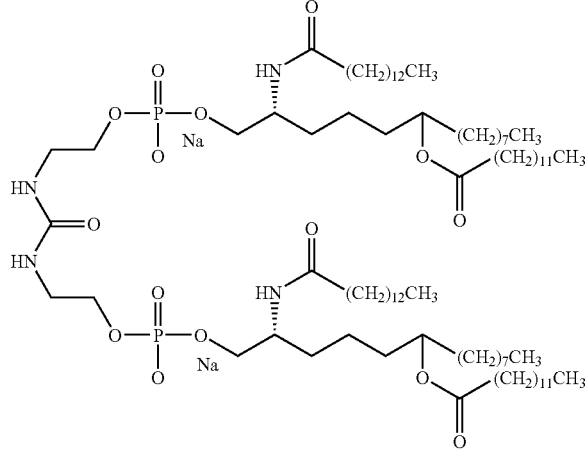 |
| 805518 Isomer A | 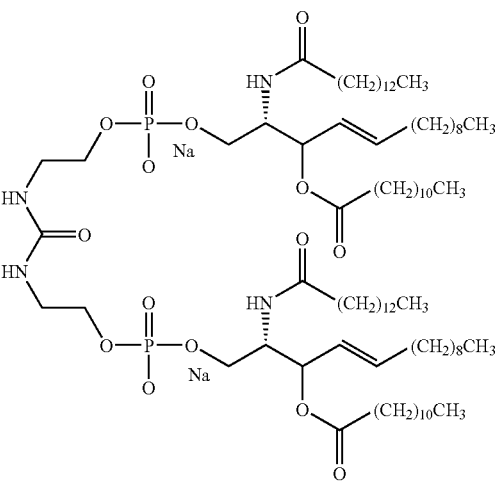 |
| 805519 Isomer B | 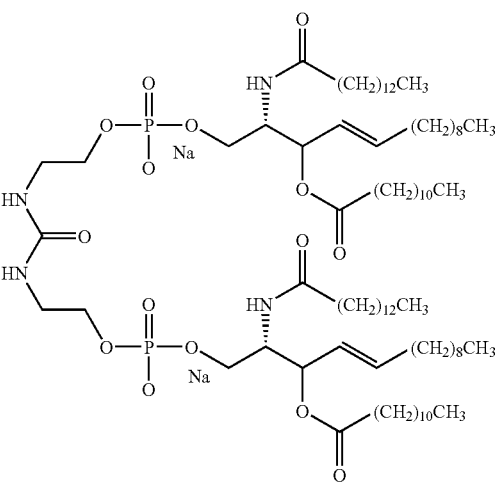 |

EXAMPLES

Example 1

Intraperitoneal Administration of a TLR Agonist Enhances Therapeutic Efficacy of a Vaccine

To determine the effect of E6020, a sodium salt of ER 804057, when administered intraperitoneally with a cancer vaccine, e.g., granulocyte-macrophage colony stimulating factor (GM-CSF) secreting tumor cells, a mouse model using melanoma cells was used.

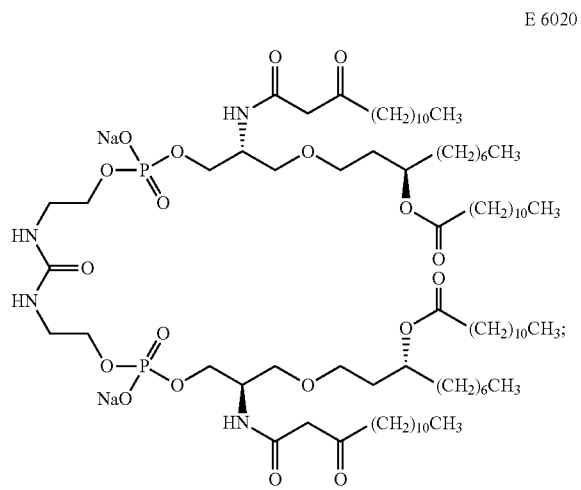

E 6020

E6020 is a TLR4 (Toll-like receptor-4) agonist. B6 mice (C57BL/6 mice) were engrafted subcutaneously with 1×10⁶ syngeneic B16F10 murine melanoma cells. Three days after tumor cell inoculation, the mice were either (1) vaccinated subcutaneously (s.c.) with 1×10⁶ B16F10 tumor cells that were genetically modified to stably express and secrete murine GM-CSF (B16-GM-CSF cells); (2) vaccinated intraperitoneally (i.p.) with E6020; or (3) were treated with a combination of s.c. GM-CSF cell vaccination and i.p. E6020 (the GM-CSF cell vaccination and E6020 vaccination were administered at separate sites in the mice). In these experiments, the GM-CSF cells were inactivated by gamma-irradiation prior to inoculation. Survival of the animals was monitored.

Example 2

Local Administration of a TLR Agonist Enhances the Therapeutic Efficacy of a Cancer Vaccine

The effect of E6020 on treatment of B6 mice that were engrafted subcutaneously with 1×10⁶ syngeneic B16F10 murine melanoma cells was examined. When tumors became palpable, the mice were injected intratumorally with GM-CSF cells alone, or in combination with E6020 (about 3-10 µg). Survival of the animals was monitored.

Figure 2:
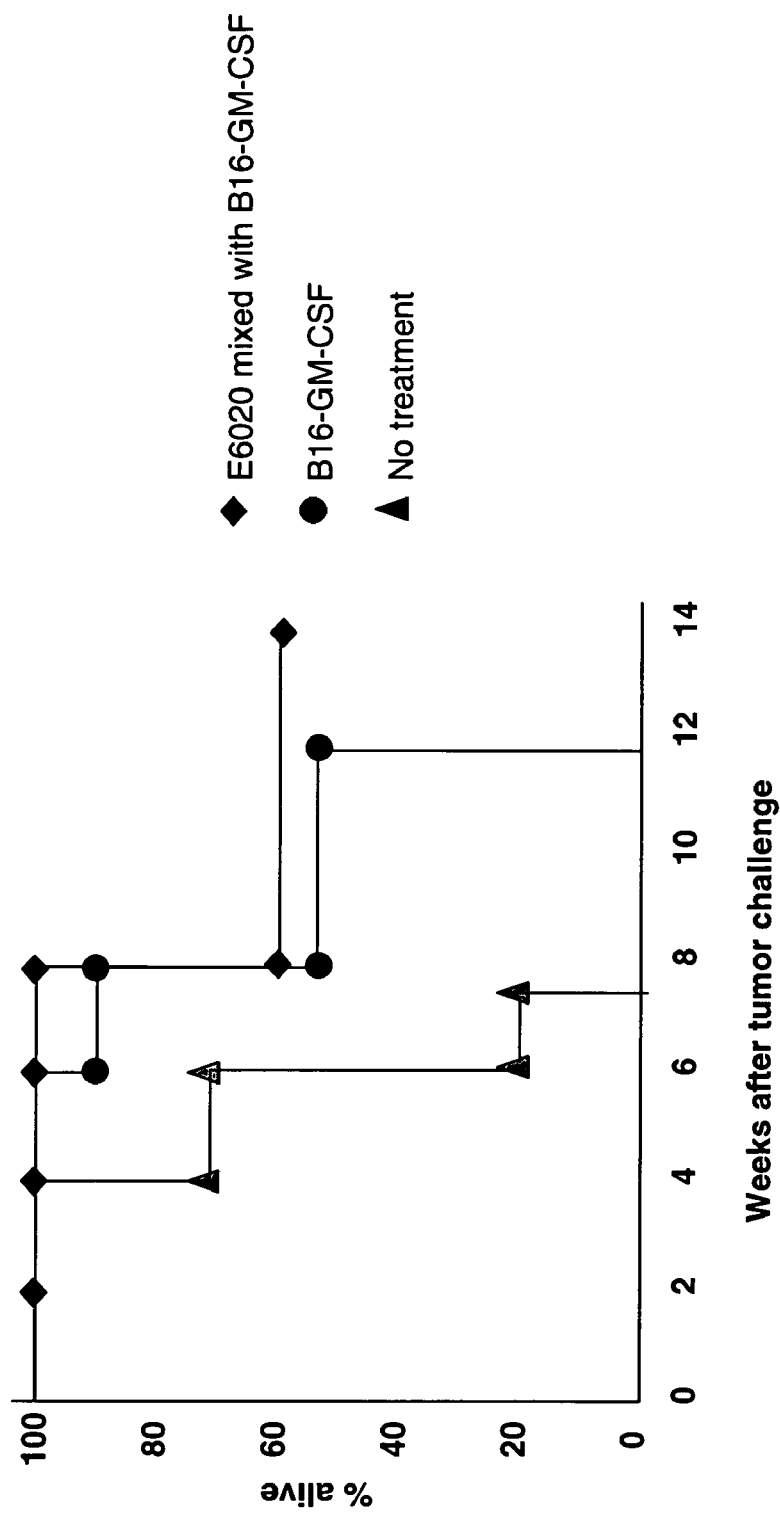
FIG. 2 is a graph depicting the percentage of tumor-bearing mice surviving after intratumoral treatment with B16 GM-CSF (R) cells, or B16 GM-CSF(r) cells and E6020, or with no treatment.

It was found that the population of animals treated intratumorally with a combination of GM-CSF cells and E6020 had increased survival compared to animals that were untreated or treated with GM-CSF cells alone (FIG. 2).

Example 3

MUC-1/E6020 Vaccine Therapeutic Effects

To test the effects of a MUC-1 vaccine with E6020 adjuvant for treating inflammatory bowel disease (IBD) and subsequent development of colon adenocarcinoma, an engineered mouse strain that lacks the IL-10 gene and expresses transgenic human MUC1 was used. Such mice spontaneously develop intestinal inflammation resembling IBD followed by colon adenocarcinoma. These data were presented and published in Beatty et al., AACR Annual Meeting 2006, Washington D.C., Apr. 4, 2006.

In these experiments, mice were immunized intranasally with 30 mg/nare of Tn MUC100mer (HGVTSAPDTRPAPG-STAPPA)×5, SEQ ID NO:1) and 3 mg of E6020. Animals were vaccinated at about 4.5 weeks and boosted at about 6.5 weeks and 9 weeks.

Figure 3:
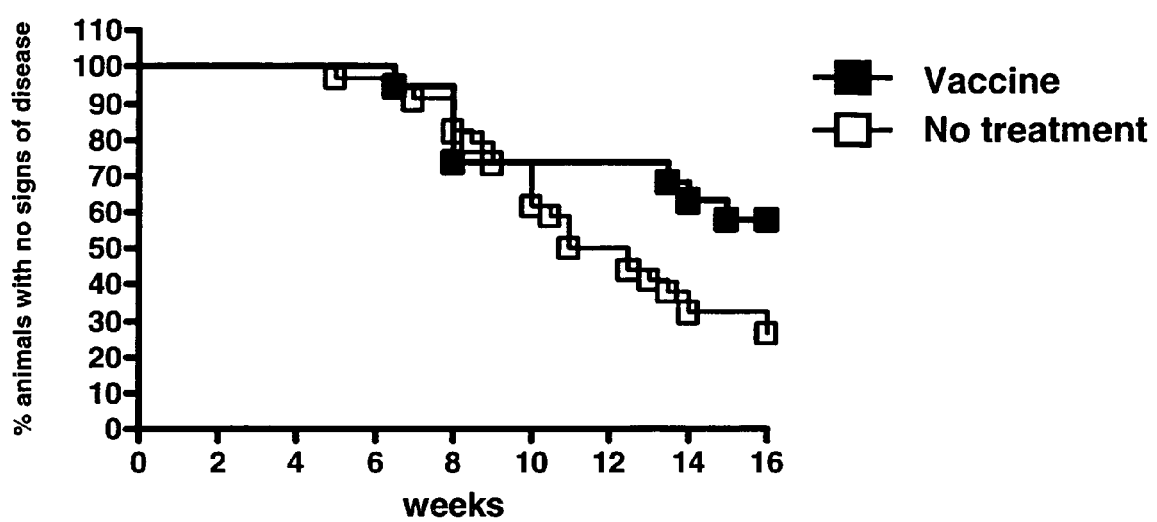
FIG. 3 is a graph depicting the percentage of animals without sign of disease after no treatment or treatment with vaccine and E6020.
Figure 4:
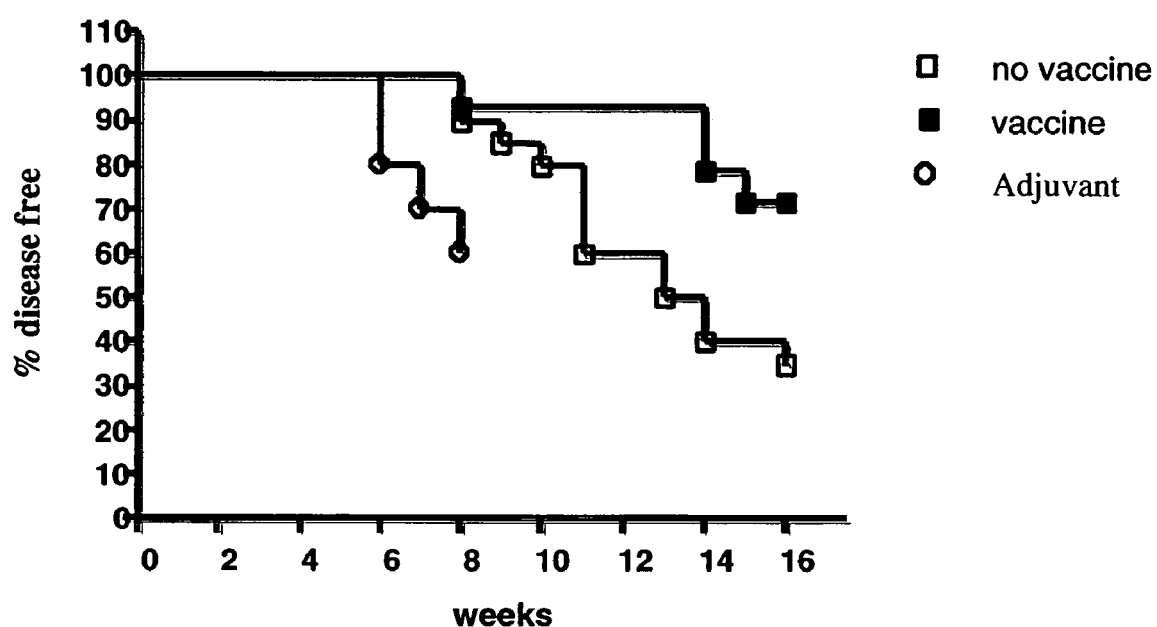
FIG. 4 is a graph depicting the percentage of animals alive after no treatment, treatment with vaccine, or treatment with E6020.

MUC IL-10-/- mice treated with vaccine and E6020 had delayed onset of IBD or did not develop IBD during the period of the experiment (FIG. 3). Mice treated with vaccine and E6020 had improved survival and did not develop colon cancer (FIG. 4 and Table 1).

TABLE 1

| Treatment/no. of mice treated | Age (weeks) | Colon tumors |
|---|---|---|
| Vaccine/6 mice | 14-35.5 | 0/6 |
| Adjuvant/3 mice | 12.5-18 | 3/3 |
| No treatment/4 mice | 8-15.5 | 4/4 |

The data demonstrate that the addition of E6020 to the MUC-1 vaccine can slow the progression to rectal prolapse associated with IBD, and suppresses the appearance of histologically detected tumors.

Example 4

EGFRvIII Therapeutic Effects with Adjuvant

To determine whether an adjuvant can enhance the effect of an oncology antigen (i.e., an antigen that can be used to vaccinate an animal against a cancer), C57/BL6J mice were immunized subcutaneously with a tumor-associated peptide, LEEKKGNYVVTDHC (SEQ ID NO: 2) (derived from mutant form of EGFR, EGFRvIII) conjugated to the protein carrier keyhole limpet hemocyanin (KLH), with or without E6020 or murine GM-CSF, a cytokine used in cancer vaccine trials to boost immune response. E6020 was dosed at 3 µg, GM-CSF at 5 µg and the peptide-KLH conjugate at 25 µg per dose. Mice were immunized three times at intervals of three weeks. Serum was prepared from mice two weeks after each immunization and tested for EGFRvIII peptide-specific antibodies using ELISA on plates coated with EGFRvIII peptide conjugated to bovine serum albumin. The results in Table 2 are presented as titers from individual animals. The titer is defined as the last serum dilution at which a signal at 0.25 OD units above background was observed.

The data from these experiments demonstrate that E6020 enhanced the mean titer of antigen-specific IgG2a, which binds high affinity Fc receptors involved in antibody-dependent cell-mediated cytotoxicity (ADCC). IgG2a is the mouse correlate of the human IgG1 isotype that is used in currently marketed human anti-tumor monoclonal antibodies, because it is most efficacious in tumor killing.

The combination of E6020 and GM-CSF in the vaccination with EGFRvIII peptide demonstrated a greater effect on IgG2a titers than either material alone. These data demonstrate the usefulness of combinations of E6020 with other immunoenhancers.

TABLE 2

Antibody titers to EGFRvIII peptide are enhanced by E6020

| | Antigen administered with: | | | | | | | |
|---|---|---|---|---|---|---|---|---|
| | PBS | | E6020 | | GM-CSF | | E6020/GMCSF | |
| Antibody subclass: | IgG1 | IgG2a | IgG1 | IgG2a | IgG1 | IgG2a | IgG1 | IgG2a |
| | 6000 | 3000 | 3000 | 1500 | 12000 | 750 | 12000 | 3000 |
| | 12000 | 3000 | 24000 | 6000 | 12000 | 750 | 12000 | 6000 |
| | 24000 | 6000 | 24000 | 6000 | 12000 | 3000 | 24000 | 24000 |
| | 24000 | 6000 | 24000 | 12000 | 24000 | 3000 | 24000 | 24000 |
| | 24000 | 6000 | 24000 | 12000 | 24000 | 6000 | 48000 | 24000 |
| | 24000 | 6000 | 24000 | 12000 | 48000 | 6000 | 48000 | 48000 |
| | 48000 | 6000 | 24000 | 24000 | 48000 | 6000 | 48000 | 48000 |
| | 48000 | 24000 | 48000 | 48000 | 48000 | 24000 | 48000 | 48000 |
| Geometric mean titer: | 22008 | 6000 | 20182 | 10091 | 24000 | 3568 | 28541 | 20182 |

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

The invention claimed is:

1. A method for inducing an immune response in a subject individual, the method comprising the steps of: administering to the individual one or more anti-cancer antibodies and administering to the individual a compound of formula (I)

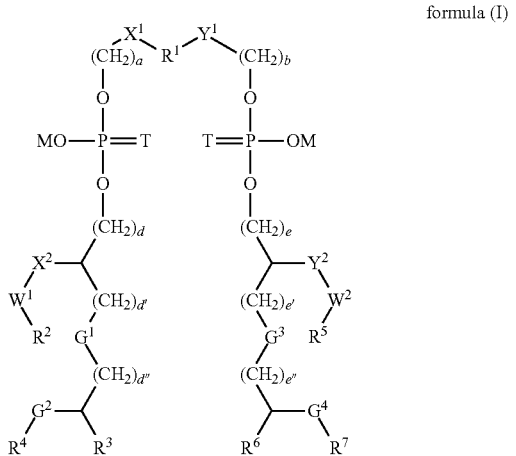

formula (I)

wherein:

$R^1$ is:

(a) —C(O)—;

(b) —C(O)—$C_{1-4}$ alkyl-C(O)— or —C(O)—$C_{1-4}$ alkenyl-C(O)—;

wherein the —$C_{1-14}$ alkyl- or —$C_{1-14}$ alkenyl- is optionally substituted with one or more substituents selected from the group consisting of hydroxy, $C_{1-6}$ alkyl, $C_{1-6}$ alkoxy, $C_{1-6}$ alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$ alkyl; and wherein the aryl moiety of the (aryl)$C_{1-6}$ alkyl is optionally substituted with one or more substituents selected from the group consisting of $C_{1-6}$ alkyl, $C_{1-6}$ alkoxy, $C_{1-6}$ alkylamino, $C_{1-6}$ alkoxyamino, $C_{1-6}$ alkylamino-$C_{1-6}$ alkoxy, —O—$C_{1-6}$ alkylamino-$C_{1-6}$ alkoxy, —O—$C_{1-6}$ alkylamino-C(O)—$C_{1-6}$ alkyl-C(O)OH, —O—$C_{1-6}$ alkylamino-C(O)—$C_{1-6}$ alkyl-C(O)—$C_{1-6}$ alkyl, —O—$C_{1-6}$ alkyl-NH—$C_{1-6}$ alkyl —O—$C_{1-6}$ alkyl, —O—$C_{1-6}$ alkyl-NH—C(O)$C_{1-6}$ alkyl-C(O)OH, and/or —O—$C_{1-6}$ alkyl - NH—C(O) $C_{1-6}$ alkyl-C(O)—$C_{1-6}$ alkyl;

(c) a $C_2$ to $C_{15}$ straight or branched chain alkyl group optionally substituted with one or more hydroxyl or alkoxy groups; or (d) —C(O)—$C_{6-12}$ aryl-C(O)— wherein the aryl is optionally substituted with one or more group selected from the group consisting of hydroxy, halo, nitro, amino, $C_{1-6}$ alkyl and $C_{1-6}$ alkoxy groups;

a and b are each independently 0, 1, 2, 3 or 4;

a' and b' are independently 2, 3, 4, 5, 6, 7 or 8;

d and e are each independently 1, 2, 3, 4, 5 or 6;

d' and e' are each independently 0, 1, 2, 3 or 4;

d" and e" are each independently 0, 1, 2, 3 or 4;

T is oxygen or sulfur;

$X^1$, $X^2$, $Y^1$ and $Y^2$ are each independently null, oxygen, NH, —N(C(O)$C_{1-4}$ alkyl)-, or —N($C_{1-4}$ alkyl)-;

$W^1$ and $W^2$ are each independently selected from the group consisting of carbonyl, methylene, sulfone and sulfoxide;

$R^2$, $R^3$, $R^4$, $R^5$, $R^6$ and $R^7$ are each independently:

(a) $C_2$ to $C_{20}$ straight chain or branched chain alkyl, which is optionally substituted with one or more groups selected from the group consisting of oxo, halo, hydroxy and alkoxy groups;

(b) $C_2$ to $C_{20}$ straight chain or branched chain alkenyl, which is optionally substituted with one or more groups selected from the group consisting of oxo, halo, hydroxy and alkoxy groups;

(c) $C_2$ to $C_{20}$ straight chain or branched chain alkoxy, which is optionally substituted with one or more groups selected from the group consisting of oxo, halo, hydroxy and alkoxy groups;

(d) —NH—$C_{2-20}$ straight chain or branched chain alkyl, wherein the alkyl group is optionally substituted with one or more groups selected from the group consisting of oxo, halo, hydroxy and alkoxy groups;

(e) —C(O)—$C_{2-20}$ straight chain or branched chain alkyl or alkenyl, wherein the alkyl or alkenyl is optionally substituted with one or more groups selected from the group consisting of oxo, halo, hydroxy and alkoxy groups;

(f)

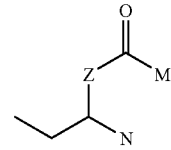

Z is O or NH; and M and N are each independently $C_2$ to $C_{20}$ straight chain or branched chain alkyl, alkenyl, alkoxy, acyloxy, alkylamino, or acylamino; or (g)

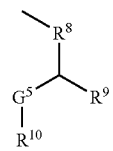

$R^8$ is $C_{1-6}$ straight or branched chain alkyl or $C_{2-6}$ straight or branched chain alkenyl or alkynyl;

$R^9$ and $R^{10}$ are independently selected from the group consisting of (i) $C_1$ to $C_{20}$ straight chain or branched chain alkyl, which is optionally substituted with one or more groups selected from the group consisting of halo, oxo, hydroxy and alkoxy; and (ii) $C_2$ to $C_{20}$ straight chain or branched chain alkenyl or alkynyl which is optionally substituted with one or more groups selected from the group consisting of halo, oxo, hydroxy and alkoxy;

$G^1$, $G^2$, $G^3$, $G^4$ and $G^5$ are each independently oxygen, methylene, —NH—, thiol, —N($C_{1-4}$ alkyl)-, —N[C(O)—$C_{1-4}$ alkyl]-, —NH—C(O)—, —NH—$SO_2$—, —C(O)—O—, —C(O)—NH—, —O—C(O)—, —O—C(O)NH—, —O—C(O)O—, —NH—C(O)—NH—, —C(O)NH—, —C(O)N($C_{1-4}$ alkyl), aryl, and —S(O)$_n$—, wherein n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from the group consisting of —OP(O)(OH)$_2$, —P(O)(OH)$_2$, —OP(O)(OR$^8$)(OH), where $R^8$ is a $C_{1-4}$ alkyl, —OS(O)$_2$OH, —S(O)$_2$OH—, —$CO_2$H, —OB(OH)$_2$, —OH, —$CH_3$, —$NH_2$, and —N($R^9$)$_2$, where $R^9$ is a $C_{1-4}$ alkyl;

$R^{12}$ is H or a $C_{1-4}$ straight or branched alkyl; and

M is independently selected from a hydrogen atom and a pharmaceutically acceptable cation;

or a pharmaceutically acceptable salt, hydrate, solvate, stereoisomer, amorphous solid thereof, or any combination thereof;

wherein said immune response results in stabilizing a tumor by preventing or slowing the growth of an existing cancer, preventing the spread of a tumor or of metastases, reducing tumor size, preventing the recurrence of treated cancer, eliminating cancer cells not killed by earlier treatments, or preventing or delaying the development of cancer in said individual;

wherein the one or more anti-cancer antibodies is trastuzumab and the compound of formula (I) is ER 804057 and/or a pharmaceutically acceptable salt, hydrate, solvate, stereoisomer, or amorphous solid thereof.

2. The method of claim 1, wherein the one or more anti-cancer antibodies and the compound of formula (I) are administered at about the same time.

3. The method of claim 1, wherein the one or more anti-cancer antibodies and the compound of formula (I) are administered separately.

4. The method of claim 1, wherein the one or more anti-cancer antibodies and the compound of formula (I) are administered to a subject individual at risk for developing cancer, diagnosed with a cancer, in treatment for cancer, or in post-therapy recovery from cancer.

5. The method of claim 4, wherein the one or more anti-cancer antibodies and the compound of formula (I) are administered therapeutically in combination with a surgical procedure to remove or reduce the size of a cancer tumor, radiation therapy, chemotherapy, and/or ablation therapy.

6. The method of claim 4, wherein the one or more anti-cancer antibodies and the compound of formula (I) are administered therapeutically to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments.

7. The method of claim 1, wherein the one or more anti-cancer antibodies and the compound of formula (I) are administered prophylactically to the subject individual to prevent or delay the development of cancer.

8. The method of claim 1, wherein the compound of formula (I) is ER 804057 and/or a pharmaceutically acceptable salt thereof.

9. The method of claim 8, wherein the pharmaceutically acceptable salt of ER 804057 is E6020

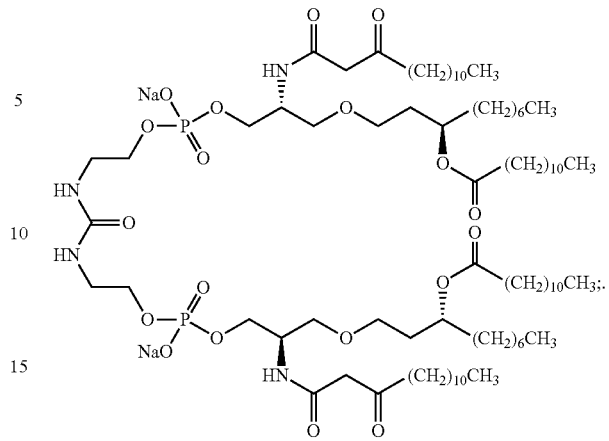

10. A method for increasing the therapeutic efficacy of an anti-cancer antibody in a subject individual, the method comprising the steps of: administering to the individual one or more anti-cancer antibodies and administering to the individual a compound of formula (I)

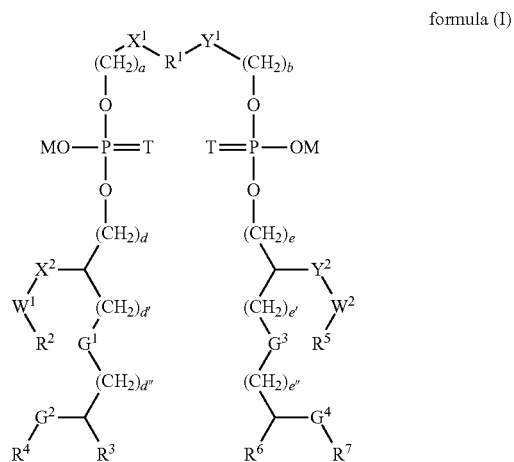

formula (I)

wherein:
$R^1$ is:
(a) —C(O)—;
(b) —C(O)—$C_{1-14}$ alkyl-C(O)— or —C(O)—$C_{1-14}$ alkenyl-C(O)—;
wherein the —$C_{1-14}$ alkyl- or —$C_{1-14}$ alkenyl- is optionally substituted with one or more substituents selected from the group consisting of hydroxy, $C_{1-6}$ alkyl, $C_{1-6}$ alkoxy, $C_{1-6}$ alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$ alkyl; and
wherein the aryl moiety of the (aryl)$C_{1-6}$ alkyl is optionally substituted with one or more substituents selected from the group consisting of $C_{1-6}$ alkyl, $C_{1-6}$ alkoxy, $C_{1-6}$ alkylamino, $C_{1-6}$ alkoxyamino, $C_{1-6}$ alkylamino-$C_{1-6}$ alkoxy, —O—$C_{1-6}$ alkylamino-$C_{1-6}$ alkoxy, —O—$C_{1-6}$ alkylamino-C(O)—$C_{1-6}$ alkyl-C(O)OH, —O—$C_{1-6}$ alkylamino-C(O)—$C_{1-6}$ alkyl-C(O)—$C_{1-6}$ alkyl, —O—$C_{1-6}$ alkyl-NH—$C_{1-6}$ alkyl -O—$C_{1-6}$ alkyl, —O—$C_{1-6}$ alkyl-NH—C(O)$C_{1-6}$ alkyl-C(O)OH, and/or —O—$C_{1-6}$ alkyl -NH—C(O)$C_{1-6}$ alkyl-C(O)—$C_{1-6}$ alkyl;

(c) a $C_2$ to $C_{15}$ straight or branched chain alkyl group optionally substituted with one or more hydroxyl or alkoxy groups; or (d) —C(O)—$C_{6-12}$ aryl-C(O)— wherein the aryl is optionally substituted with one or more group selected from the group consisting of hydroxy, halo, nitro, amino, $C_{1-6}$ alkyl and $C_{1-6}$ alkoxy groups;

a and b are each independently 0, 1, 2, 3 or 4;
a' and b' are independently 2, 3, 4, 5, 6, 7 or 8;
d and e are each independently 1, 2, 3, 4, 5 or 6;
d' and e' are each independently 0, 1, 2, 3 or 4;
d'' and e'' are each independently 0, 1, 2, 3 or 4;
T is oxygen or sulfur;
$X^1$, $X^2$, $Y^1$ and $Y^2$ are each independently null, oxygen, NH, —N(C(O)$C_{1-4}$ alkyl)-, or —N($C_{1-4}$ alkyl)-;
$W^1$ and $W^2$ are each independently selected from the group consisting of carbonyl, methylene, sulfone and sulfoxide;
$R^2$, $R^3$, $R^4$, $R^5$, $R^6$ and $R^7$ are each independently:

(a) $C_2$ to $C_{20}$ straight chain or branched chain alkyl, which is optionally substituted with one or more groups selected from the group consisting of oxo, halo, hydroxy and alkoxy groups;

(b) $C_2$ to $C_{20}$ straight chain or branched chain alkenyl, which is optionally substituted with one or more groups selected from the group consisting of oxo, halo, hydroxy and alkoxy groups;

(c) $C_2$ to $C_{20}$ straight chain or branched chain alkoxy, which is optionally substituted with one or more groups selected from the group consisting of oxo, halo, hydroxy and alkoxy groups;

(d) —NH—$C_{2-20}$ straight chain or branched chain alkyl, wherein the alkyl group is optionally substituted with one or more groups selected from the group consisting of oxo, halo, hydroxy and alkoxy groups;

(e) —C(O)—$C_{2-20}$ straight chain or branched chain alkyl or alkenyl, wherein the alkyl or alkenyl is optionally substituted with one or more groups selected from the group consisting of oxo, halo, hydroxy and alkoxy groups;

(f)

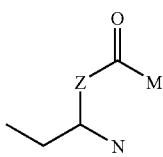

Z is O or NH; and M and N are each independently $C_2$ to $C_{20}$ straight chain or branched chain alkyl, alkenyl, alkoxy, acyloxy, alkylamino, or acylamino; or (g)

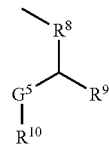

$R^8$ is $C_{1-6}$ straight or branched chain alkyl or $C_{2-6}$ straight or branched chain alkenyl or alkynyl;

$R^9$ and $R^{10}$ are independently selected from the group consisting of
(i) $C_1$ to $C_{20}$ straight chain or branched chain alkyl, which is optionally substituted with one or more groups selected from the group consisting of halo, oxo, hydroxy and alkoxy; and
(ii) $C_2$ to $C_{20}$ straight chain or branched chain alkenyl or alkynyl which is optionally substituted with one or more groups selected from the group consisting of halo, oxo, hydroxy and alkoxy;

$G^1$, $G^2$, $G^3$, $G^4$ and $G^5$ are each independently oxygen, methylene, —NH—, thiol, —N($C_{1-4}$ alkyl)-, —N[C(O)—$C_{1-4}$ alkyl]-, —NH—C(O)—, —NH—SO$_2$—, —C(O)—O—, —C(O)—NH—, —O—C(O)—, —O—C(O)NH—, —O—C(O)O—, —NH—C(O)—NH—, —C(O)NH—, —C(O)N($C_{1-4}$ alkyl), aryl, and —S(O)$_n$—,
wherein n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from the group consisting of —OP(O)(OH)$_2$, —P(O)(OH)$_2$, —OP(O)(OR$^8$)(OH), where $R^8$ is a $C_{1-4}$ alkyl, —OS(O)$_2$OH, —S(O)$_2$OH, —CO$_2$H, —OB(OH)$_2$, —OH, —CH$_3$, —NH$_2$, and —N($R^9$)$_2$, where $R^9$ is a $C_{1-4}$ alkyl;

$R^{12}$ is H or a $C_{1-4}$ straight or branched alkyl; and

M is independently selected from a hydrogen atom and a pharmaceutically acceptable cation;

or a pharmaceutically acceptable salt, hydrate, solvate, stereoisomer, amorphous solid thereof, or any combination thereof wherein the increased therapeutic efficacy of the one or more anti-cancer antibodies results in stabilizing a tumor by preventing or slowing the growth of an existing cancer, preventing the spread of a tumor or of metastases, reducing tumor size, preventing the recurrence of treated cancer, eliminating cancer cells not killed by earlier treatments, or preventing or delaying the development of cancer in said individual;

wherein the one or more anti-cancer antibodies is trastuzumab and the compound of formula (I) is ER 804057 and/or a pharmaceutically acceptable salt, hydrate, solvate, stereoisomer, or amorphous solid thereof.

11. The method of claim 10, wherein the one or more anti-cancer antibodies and the compound of formula (I) are administered at about the same time.

12. The method of claim 10, wherein the one or more anti-cancer antibodies and the compound of formula (I) are administered separately.

13. The method of claim 10, wherein the one or more anti-cancer antibodies and the compound of formula (I) are administered to a subject individual at risk for developing cancer, diagnosed with a cancer, in treatment for cancer, or in post-therapy recovery from cancer.

14. The method of claim 13, wherein the one or more anti-cancer antibodies and the compound of formula (I) are administered therapeutically in combination with a surgical procedure to remove or reduce the size of a cancer tumor, radiation therapy, chemotherapy, and/or ablation therapy.

15. The method of claim 13, wherein the one or more anti-cancer antibodies and the compound of formula (I) are administered therapeutically to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments.

16. The method of claim 10, wherein the one or more anti-cancer antibodies and the compound of formula (I) are administered prophylactically to the subject individual to prevent or delay the development of cancer.

17. The method of claim 10, wherein the compound of formula (I) is ER 804057 and/or a pharmaceutically acceptable salt thereof.

18. The method of claim 17, wherein the pharmaceutically acceptable salt of ER 804057 is E6020

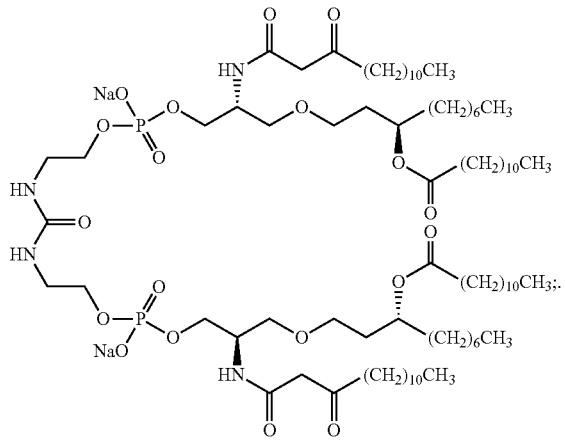

19. A method for treating or preventing cancer in a subject individual, the method comprising the steps of administering to the individual one or more anti-cancer antibodies and administering to the individual a compound of formula (I)

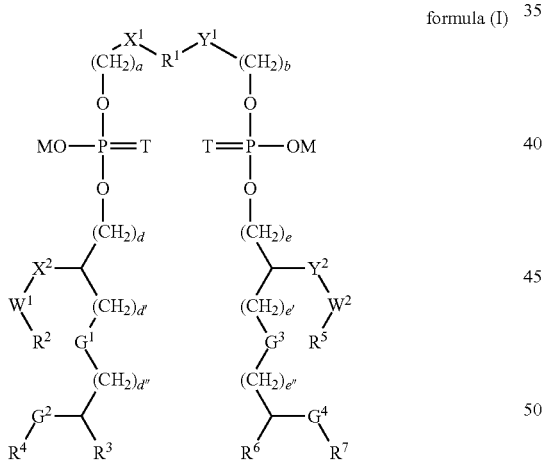

formula (I)

wherein:

$R^1$ is:
(a) —C(O)—;
(b) —C(O)—$C_{1-14}$ alkyl-C(O)— or —C(O)—$C_{1-14}$ alkenyl-C(O)—;
wherein the —$C_{1-14}$ alkyl- or —$C_{1-14}$ alkenyl- is optionally substituted with one or more substituents selected from the group consisting of hydroxy, $C_{1-6}$ alkyl, $C_{1-6}$ alkoxy, $C_{1-6}$ alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$ alkyl; and
wherein the aryl moiety of the (aryl)$C_{1-6}$ alkyl is optionally substituted with one or more substituents selected from the group consisting of $C_{1-6}$ alkyl, $C_{1-6}$ alkoxy, $C_{1-6}$ alkylamino, $C_{1-6}$ alkoxyamino, $C_{1-6}$ alkylamino-$C_{1-6}$ alkoxy, —O—$C_{1-6}$ alkylamino-$C_{1-6}$ alkoxy, —O—$C_{1-6}$ alkylamino-C(O)—$C_{1-6}$ alkyl-C(O)OH, —O—$C_{1-6}$ alkylamino-C(O)—$C_{1-6}$ alkyl-C(O)—$C_{1-6}$ alkyl, —O—$C_{1-6}$ alkyl-NH—$C_{1-6}$ alkyl-O—$C_{1-6}$ alkyl, —O—$C_{1-6}$ alkyl-NH—C(O)$C_{1-6}$ alkyl-C(O)OH, and/or —O—$C_{1-6}$ alkyl-NH—C(O)$C_{1-6}$ alkyl-C(O)—$C_{1-6}$ alkyl;

(c) a $C_2$ to $C_{15}$ straight or branched chain alkyl group optionally substituted with one or more hydroxyl or alkoxy groups; or (d) —C(O)—$C_{6-12}$ aryl-C(O)— wherein the aryl is optionally substituted with one or more group selected from the group consisting of hydroxy, halo, nitro, amino, $C_{1-6}$ alkyl and $C_{1-6}$ alkoxy groups;

a and b are each independently 0, 1, 2, 3 or 4;

a' and b' are independently 2, 3, 4, 5, 6, 7 or 8;

d and e are each independently 1, 2, 3, 4, 5 or 6;

d' and e' are each independently 0, 1, 2, 3 or 4;

d" and e" are each independently 0, 1, 2, 3 or 4;

T is oxygen or sulfur;

$X^1$, $X^2$, $Y^1$ and $Y^2$ are each independently null, oxygen, NH, —N(C(O)$C_{1-4}$ alkyl)-, or —N($C_{1-4}$ alkyl)-;

$W^1$ and $W^2$ are each independently selected from the group consisting of carbonyl, methylene, sulfone and sulfoxide;

$R^2$, $R^3$, $R^4$, $R^5$, $R^6$ and $R^7$ are each independently:

(a) $C_2$ to $C_{20}$ straight chain or branched chain alkyl, which is optionally substituted with one or more groups selected from the group consisting of oxo, halo, hydroxy and alkoxy groups;

(b) $C_2$ to $C_{20}$ straight chain or branched chain alkenyl, which is optionally substituted with one or more groups selected from the group consisting of oxo, halo, hydroxy and alkoxy groups;

(c) $C_2$ to $C_{20}$ straight chain or branched chain alkoxy, which is optionally substituted with one or more groups selected from the group consisting of oxo, halo, hydroxy and alkoxy groups;

(d) —NH—$C_{2-20}$ straight chain or branched chain alkyl, wherein the alkyl group is optionally substituted with one or more groups selected from the group consisting of oxo, halo, hydroxy and alkoxy groups;

(e) —C(O)—$C_{2-20}$ straight chain or branched chain alkyl or alkenyl, wherein the alkyl or alkenyl is optionally substituted with one or more groups selected from the group consisting of oxo, halo, hydroxy and alkoxy groups;

(f)

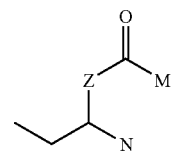

Z is O or NH; and M and N are each independently $C_2$ to $C_{20}$ straight chain or branched chain alkyl, alkenyl, alkoxy, acyloxy, alkylamino, or acylamino; or (g)

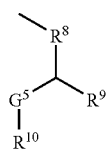

$R^8$ is $C_{1-6}$ straight or branched chain alkyl or $C_{2-6}$ straight or branched chain alkenyl or alkynyl;

$R^9$ and $R^{10}$ are independently selected from the group consisting of
 (i) $C_1$ to $C_{20}$ straight chain or branched chain alkyl, which is optionally substituted with one or more groups selected from the group consisting of halo, oxo, hydroxy and alkoxy; and
 (ii) $C_2$ to $C_{20}$ straight chain or branched chain alkenyl or alkynyl which is optionally substituted with one or more groups selected from the group consisting of halo, oxo, hydroxy and alkoxy;

$G^1$, $G^2$, $G^3$, $G^4$ and $G^5$ are each independently oxygen, methylene, —NH—, thiol, —N($C_{1-4}$ alkyl)-, —N[C(O)—$C_{1-4}$ alkyl]-, —NH—C(O)—, —NH—SO$_2$—, —C(O)—O—, —C(O)—NH—, —O—C(O)—, —O—C(O)NH—, —O—C(O)O—, —NH—C(O)—NH—, —C(O)NH—, —C(O)N($C_{1-4}$ alkyl), aryl, and —S(O)$_n$—, wherein n is 0, 1, or 2;
or $G^1R^2$, $G^2R^4$, $G^3R^5$ and/or $G^4R^7$ may together be a hydrogen atom or hydroxyl;

$Z^1$ and $Z^2$ are each independently selected from the group consisting of —OP(O)(OH)$_2$, —P(O)(OH)$_2$, —OP(O)(OR$^8$)(OH), where $R^8$ is a $C_{1-4}$ alkyl, —OS(O)$_2$OH, —S(O)$_2$OH—, —CO$_2$H, —OB(OH)$_2$, —OH, —CH$_3$, —NH$_2$, and —N(R$^9$)$_2$, where $R^9$ is a $C_{1-4}$ alkyl;

$R^{12}$ is H or a $C_{1-4}$ straight or branched alkyl; and

M is independently selected from a hydrogen atom and a pharmaceutically acceptable cation;

or a pharmaceutically acceptable salt, hydrate, solvate, stereoisomer, amorphous solid thereof, or any combination thereof;

wherein said administering results in stabilizing a tumor by preventing or slowing the growth of an existing cancer, preventing the spread of a tumor or of metastases, reducing tumor size, preventing the recurrence of treated cancer, eliminating cancer cells not killed by earlier treatments, or preventing or delaying the development of cancer in said individual;

wherein the one or more anti-cancer antibodies is trastuzumab and the compound of formula (I) is ER 804057 and/or a pharmaceutically acceptable salt, hydrate, solvate, stereoisomer, or amorphous solid thereof.

20. The method of claim 19, wherein the one or more anti-cancer antibodies and the compound of formula (I) are administered at about the same time.

21. The method of claim 19, wherein the one or more anti-cancer antibodies and the compound of formula (I) are administered separately.

22. The method of claim 19, wherein the one or more anti-cancer antibodies and the compound of formula (I) are administered to a subject individual at risk for developing cancer, diagnosed with a cancer, in treatment for cancer, or in post-therapy recovery from cancer.

23. The method of claim 22, wherein the one or more anti-cancer antibodies and the compound of formula (I) are administered therapeutically in combination with a surgical procedure to remove or reduce the size of a cancer tumor, radiation therapy, chemotherapy, and/or ablation therapy.

24. The method of claim 22, wherein the one or more anti-cancer antibodies and the compound of formula (I) are administered therapeutically to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments.

25. The method of claim 19, wherein the one or more anti-cancer antibodies and the compound of formula (I) are administered prophylactically to the subject individual to prevent or delay the development of cancer.

26. The method of claim 19, wherein the compound of formula (I) is ER 804057 and/or a pharmaceutically acceptable salt thereof.

27. The method of claim 26, wherein the pharmaceutically acceptable salt of ER 804057 is E6020

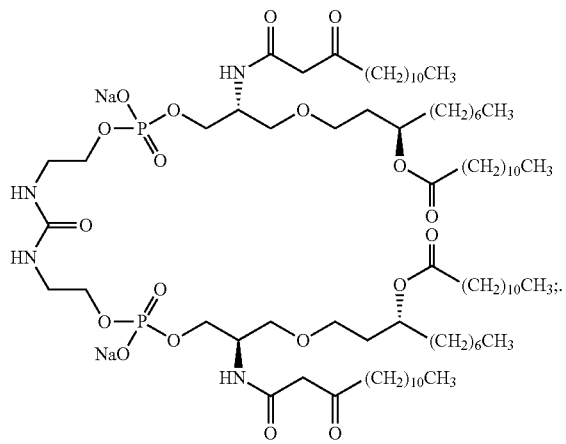

* * * * *

UNITED STATES PATENT AND TRADEMARK OFFICE
CERTIFICATE OF CORRECTION

PATENT NO. : 7,976,852 B2  Page 1 of 1
APPLICATION NO. : 11/411332
DATED : July 12, 2011
INVENTOR(S) : Rossignol et al.

It is certified that error appears in the above-identified patent and that said Letters Patent is hereby corrected as shown below:

Column 101, Claim 1, Line 31: Please correct "–C(O) –$C_{1-4}$ alkyl-C(O)–"
to read -- –C(O) –$C_{1-14}$ alkyl-C(O)– --
and correct "–C(O) –$C_{1-4}$ alk-"
to read -- –C(O) –$C_{1-14}$ alk- --

Signed and Sealed this
Twenty-second Day of November, 2011

David J. Kappos
*Director of the United States Patent and Trademark Office*

```
                          SEQUENCE LISTING

<160> NUMBER OF SEQ ID NOS: 2

<210> SEQ ID NO 1
<211> LENGTH: 100
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

His Gly Val Thr Ser Ala Pro Asp Thr Arg Pro Ala Pro Gly Ser Thr
 1               5                  10                  15

Ala Pro Pro Ala His Gly Val Thr Ser Ala Pro Asp Thr Arg Pro Ala
            20                  25                  30

Pro Gly Ser Thr Ala Pro Pro Ala His Gly Val Thr Ser Ala Pro Asp
        35                  40                  45

Thr Arg Pro Ala Pro Gly Ser Thr Ala Pro Pro Ala His Gly Val Thr
50                  55                  60

Ser Ala Pro Asp Thr Arg Pro Ala Pro Gly Ser Thr Ala Pro Pro Ala
65                  70                  75                  80

His Gly Val Thr Ser Ala Pro Asp Thr Arg Pro Ala Pro Gly Ser Thr
                85                  90                  95

Ala Pro Pro Ala
            100

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Leu Glu Glu Lys Lys Gly Asn Tyr Val Val Thr Asp His Cys
 1               5                  10
```